XXXXX# United States Patent
Schmidt

(10) Patent No.: US 7,431,701 B2
(45) Date of Patent: Oct. 7, 2008

(54) METHOD AND SYSTEM FOR DIAGNOSIS OF LOWER URINARY TRACT DYSREGULATION AND RELATED CONDITIONS

(76) Inventor: Richard A. Schmidt, 12136 W. 75th La., Arvada, CO (US) 80005

( * ) Notice: Subject to any disclaimer, the term of this patent is extended or adjusted under 35 U.S.C. 154(b) by 881 days.

(21) Appl. No.: 10/363,892

(22) PCT Filed: Sep. 13, 2001

(86) PCT No.: PCT/US01/28509

§ 371 (c)(1),
(2), (4) Date: Mar. 7, 2003

(87) PCT Pub. No.: WO02/22008

PCT Pub. Date: Mar. 21, 2002

(65) Prior Publication Data

US 2004/0015100 A1    Jan. 22, 2004

Related U.S. Application Data

(60) Provisional application No. 60/232,280, filed on Sep. 13, 2000.

(51) Int. Cl.
*A61B 5/103* (2006.01)
*A61B 5/117* (2006.01)
*A61B 5/00* (2006.01)

(52) U.S. Cl. .................. 600/587; 600/561; 128/923

(58) Field of Classification Search ............ 600/29–32, 600/300, 587; 128/920, 923–925
See application file for complete search history.

(56) References Cited

U.S. PATENT DOCUMENTS 4,771,792 A    9/1988 Seale (Continued)

FOREIGN PATENT DOCUMENTS

RU    2154824    *    8/2000

(Continued)

OTHER PUBLICATIONS de Jonge, M.C., Kornelis, J. A., and van den, Berg, J., Abstract, "The Static Urethral Closure Pressure Profile in Female Incontinence. A Comparison Between Sphincter and Detrusor Incontinence,", National Library of Medicine, http://www.pubmed.com, (month unknown 1981).

(Continued)

*Primary Examiner*—Max F. Hindenburg
*Assistant Examiner*—Michael Apanius
(74) *Attorney, Agent, or Firm*—Hensley Kim & Holzer, LLC

(57) ABSTRACT

The invention disclosed herein provides a system and method for diagnosing lower urinary system conditions by receiving urodynamic data and subjective symptomatic impressions concerning a patient. The system and method then assigns weighted point values to the urodynamic data, for example, urethal pressure profiles due to sphincter contraction conditions such as urgency (2) and stress incontinence (4), and the subjective symptomatic impressions, quantifies norms for lower urinary system function, as a whole or in part, and quantifies recognized pathologies of lower urinary system conditions as degrees of departure from the norms. The system and method then determines a lower urinary system condition diagnosis of the patient, as a function of the degrees of departure from the norms, by invoking a set of rules to compare the weighted point values assigned and the quantified norms. The invention then reports the lower urinary system condition diagnosis, treatment recommendation, or further diagnostic suggestions.

47 Claims, 34 Drawing Sheets

U.S. PATENT DOCUMENTS

| | | | |
|---|---|---|---|
| 5,058,591 A | | 10/1991 | Companion et al. |
| 5,331,548 A | * | 7/1994 | Rollema et al. .............. 600/561 |
| 5,433,216 A | | 7/1995 | Sugrue et al. ................ 128/778 |
| 5,437,278 A | * | 8/1995 | Wilk ........................... 600/425 |
| 5,551,436 A | * | 9/1996 | Yago ........................... 600/483 |
| 5,617,876 A | | 4/1997 | van Duyl ..................... 128/780 |
| 5,746,204 A | | 5/1998 | Schauss ....................... 128/630 |
| 5,993,386 A | * | 11/1999 | Ericsson ...................... 600/300 |
| 6,056,690 A | | 5/2000 | Roberts ....................... 600/300 |
| 6,056,699 A | | 5/2000 | Sohn et al. ................... 600/561 |
| 6,063,026 A | * | 5/2000 | Schauss et al. .............. 600/300 |
| 6,110,109 A | * | 8/2000 | Hu et al. ...................... 600/300 |

FOREIGN PATENT DOCUMENTS

| | | |
|---|---|---|
| WO | WO 98/02836 | 1/1998 |
| WO | WO 00/79466 A2 | 12/2000 |

OTHER PUBLICATIONS

Versi, E, Abstract, "Discriminant Analysis of Urethral Pressure Profilometry Data For the Diagnosis of Genuine Stress Incontinence.", National Library of Medicine, http://www.pubmed.com, (month unknown 1990).

Meyer, S., De Grandi, P., Schmidt, N., Sanzeni, W., Spinosa, J.P., Abstract, "Urodynamic Parameters in Patients With Slight and Severe Genuine Stress Incontinence: Is the Stress Profile Useful?", National Library of Medicine, http://www.pubmed.com, month unknown 1994).

Methfessel, Wolters M., Abstract, "Computer-Assisted Analysis of Urethral Pressure Profiles in the Woman",National Library of Medicine, http://www.pubmed.com, (month unknown 1996).

Lose, G., Abstract, "Urethral Pressure Measurement.", National Library of Medicine, http://www.pubmed.com, (month unknown 1997).

Dantec Medical (now Medtronic), brochure for Duet MultiP, "Complete System for Pelvic Floor Functional Diagnostics", (date unknown).

* cited by examiner

STORAGE REGULATION FAILURE

- FAILURE OF SPHINCTER TONE DURING FILLING
    - SYMPTOMS
        - URGENCY/FREQUENCY
        - PELVIC PAIN
        - "STRESS INCONTINENCE"
        - "PRECIPITOUS" URGE

SCORING CMG VOID

VOID TRIGGERS
- SOMATIC
- FILL
- VOLUNTARY
- ABSENT

FIG.31

SCORING CMG SENSATION

SCORE
- 0 • NORMAL
- 1 • INCREASED
- 2 • DECREASED

FIG.32

SCORING CMG COMPLIANCE

BLADDER VOLUMES
- AT 1ST PRESSURE CHANGE
- AT PEAK PRESSURE CHANGE

BLADDER PRESSURE
- AT MAX FILL

FIG.33

FLOW SCORING GOAL

SCORE BOOTH
A) TRADITIONAL PARAMETERS
B) PATTERNS

BETTER SEPARATES
NEUROLOGICAL FROM
ANATOMICAL COMPONENTS

FIG.34

N'URO-DYNAMIC EVALUATION

| | | |
|---|---|---|
| NAME | TODAYS DATE 8/3/98 | HOSP |
| | | NEURO DX |
| FIRST MI | REFERRING MD | |
| BIRTH DATE AGE | PRESENTING SX URINARY RETENTION 2°) | US SIZE |
| | STATUS EVALUATION | US TRS ZN |
| SEX UNIT # | TYPE OF PROCEDURE | TUPR GMS RESECTED |

URETHRAL PRESSURE PROFILE

1) URETHRAL PROFILE PEAK PRESSURES

A) BLADDER <50% CAPACITY

| | BL VOL | % CAP | SCORE |
|---|---|---|---|
| REST SPH PREA 51 | 105 | 30 | |
| 51 | | | 1 |
| AVER PRESS | 51 | | |

B) BLADDER ≥50% CAPACITY  1

| | BL VOL | % CAP |
|---|---|---|
| STRESS PK PRESS 1  59 | 345 | 100 |
| STRESS PK PRESS 2  49 | | |
| AVER PRESS | 54 | |

2) REACTIVITY   NO SPIKING          0
3) SENSITIVITY  NO PAIN             0

4) PROFILE LENGTH                         SCORE

TRUE SPH LENGTH SCORE                1
A) UPP LENGTH EMPTY      3
B) UPP LENGTH FULL       3
C) LENGTH OBSTRUCTIVE ZN 0        0
D) PEAK PRESSURE OBSTRUCTIVE ZN 0  0

5) FEMALES ONLY                   SCORE

A) BL NECK MOBILITY
B) STRESS LEAKAGE
C) LEAK POSITION

4) SPHINCTER BEHAVIOR - CLINICAL IMPRESSIONS

A) PROFILE PATTERN   NORMAL (BELL SHAPE)   0
   A) DYSFUNCTIONAL NATURE
     NOT RELEVANT            0
     IF WEAK NOT RELEVANT
   B) OBSTRUCTIVE COMPONENT  NONE
     BN OR BPH NOT RELEVANT        0
     STRICTURE   NONE              ?

B) SPHINCTER EXCITABILITY
  REACTIVE                              1

| PROFILE TOTAL SCORE 4 | DEGREE ABNORMAL | 10% |
|---|---|---|
| SPASTIC DYSFUNCTION | 4% | |
| OBSTRUCTIVE SCORE | 0% | STRESS RISK 16% |

CYSTOMETRICS                              N=0 MAX=2

CONTRACTILITY

UNINHIBITED CONTRACTIONS <350 CC SCORE
  A) BL VOL       CC
  B) BL PRESS     CM/H2O
  C) DURATION     SEC

VOLUNTARY VOID ATTEMPT                SCORE
  A) BLADDER VOLUME    345       2
  B) BLADDER PRESSURE   9        2
  C) DURATION OF CONTR'N  0   SEC 4

COMPLIANCE CALC                        1
  MAXIMUM BLADDER PRESSURE             6
  A) BL VOL AT 1ST FILL PRESSURE CHANGE  270   0
  B) MAX BL VOL AT MAX PRESSURE  345         0
    COMPLIANCE  .08

CLINICAL IMPRESSIONS

VOID REFLEX ACTIVITY

A) VOID ONSET ABSENT
  REASON FOR ABSENT DETRUSOR  CHRONIC SPHINCTER INHIBITION
  SCORE 2
B) TYPE OF VOID TRIGGER VOLUNTARY INITIATION   SCORE 0
  IF SPASTIC NOT APPLICABLE          IF ABSENT
C) MONITORED VOID    NO-RESULTS IMPLIED FROM FLOW

SENSATION             AWARENESS URGE ONLY
  VOL. FIRST SENSATION    270   2
  BLADDER PRESS 1ST SENS'N       2
  INCREASED  MINIMAL DISCOMFORT
  DECREASED
    SCORE BLADDER SENS'N 0

FIG.40A

N'URO-DYNAMIC EVALUATION

| | | |
|---|---|---|
| NAME | TODAYS DATE 8/3/98 | HOSP |
| FIRST MI | REFERRING MD | NEURO DX |
| BIRTH DATE AGE | PRESENTING SX URINARY RETENTION 2°) | US SIZE |
| SEX UNIT # | STATUS EVALUATION | US TRS ZN |
| | TYPE OF PROCEDURE | TUPR GMS RESECTED |

COMPLIANCE DEVIATION FROM NORMAL 11 %  DETRUSOR MOTOR FUNCTION    NORMAL   (DURING CYSTOMETRY)
COMPLIANCE SIGNIFICANCE NORMAL OR         DETRUSOR REFLEX RATING      0 % OF MAX SPASTICITY
                                          CLASS OF HYPERREFLEXIA  AREFLEXIC

LEVATOR EMG  1) DURING FILLING  NOT APPLICABLE
             2) DURING VOID

SPHINCTER DYNAMICS

FILL PHASE                              SCORE
  A) BASELINE PRESSURE
         51                               2
                                                        C) BEHAVIOUR                SCORE
  B) FUNCTIONAL RANGE                                      STABLE ≤5CM                0
         SUSTAINED                        0

PRE VOID PHASE (1 MIN BEFORE DETRUSOR CONTRACTION)
  A) RELAXATION SCORE      SCORE
         SUSTAINED HIGH PRESS    2                                                   SCORE
  B) INSTABILITY                                   C) SPH PRESS PREVOID 49             2
         SUBTLE E <5CM    1

VOID PHASE FROM START OF DETRUSOR                                                    SCORE
                                                   SOMATIC TRIGGER NONE
                                         SCORE    SPH PRESS DURING VOID               0    100% EFF.
SYNERGY WITH VOID        NONE              3             ATTEMPT
ATTEMPT
RELAX'N WITH VOID        NONE              2              TOTAL SCORE SPH DYN 10
ATTEMPT                                                   SCORE% ABN SPH DYN 44

STUDY DATE [   ]       TIMEFRAME [   ]

RETENTION NO              6) OBSTRUCTIVE CHARACTER OF FLOW CURVE
                              SCORE                                                SCORE
1) PK FLOW RATE     4 CC/S     4       FLOW CURVE  DRIBBLE OR                       4.0
2) TIME (SEC)                                      INSIGNIFICANT FLOW
3) AV FLOW RATE     2 CC/S     4             7) DYSFUNCTIONAL CHARACTER OF FLOW CURVE
   AVER/PEAK RATIO  55.26                               FLOW BEHAVIOR       SCORE
4) TOTAL FLOW TIME    11               A)  MAIN FLOW    CHOPPY               3.0
5) VOLUME VOIDED    24 CC      4           SIGNIFICANCE MORE THAN HALF OF    2.0
                                       B)  POST FLOW   POST VOID VOIDING     2.0

FIG.40B

N'URO-DYNAMIC EVALUATION           HOSP
NAME                               TODAYS DATE 8/3/98          NEURO DX
FIRST          MI                  REFERRING MD                              MD
                                   PRESENTING SX URINARY RETENTION    2°)         US SIZE
BIRTH DATE          AGE            STATUS   EVALUATION                            US TRS ZN
SEX        UNIT #                  TYPE OF PROCEDURE                              TUPR GMS RESECTED

6)   RESIDUAL        321 CC    4           7)   SIGNIFICANCE    EVENTS <10 SEC    0.5
     STORAGE VOLUME  345 CC    2                                                  7.5

TOTAL FLOW POINTS   DEGREE ABNORMAL    OBSTRUCTIVE COMPONENT 100%
     26                  102 %              NEUROGENIC COMPONENT 96%

COMPUTER DIAGNOSIS AND TREATMENT RECOMMENDATIONS
    COMPUTER DX   NOT AVAILABLE, USE ALL SPECIFIC DX CHOICE(S) - 1, 2, 3, OR 4

SPECIFIC DX CHOICES                        ACONTRACTILE BLADDER
 1) USE ONLY IF NO COMPUTER DX - ACONTRACTILE BLADDER AND
    USE AT ALL TIMES WHEN INDICATED     2   POOR PELVIC MUSCLE CONTROL      4
                                        3
           DIAGNOSIS
                                            A VOIDING CYSTOURETHROGRAM (VCUG) AND A CYSTOSCOPY SHOULD
           DX VOIDING DYSFUNCTION - RETENTION   BE PERFORMED TO COMPLETE THIS PATIENT'S EVALUATION.
           POSSIBLY NEUROLOGIC
    RECOMMENDED EVALUATIONS        STANDARD STUDIES

TREATMENT OPTIONS OTHER THAN COMPUTER SUGGESTIONS
                         APPROACH
                                          B) DRUG OPTIONS
      A) SURGICAL RX

FIG.40C

N'URO-DYNAMIC EVALUATION        HOSP
NAME                    TODAYS DATE 8/3/98              NEURO DX
FIRST           MI              REFERRING MD                            MD
                                                                                US SIZE
BIRTH DATE              AGE     PRESENTING SX URINARY RETENTION    2°)
                                STATUS  EVALUATION                              US TRS ZN
SEX             UNIT #          TYPE OF PROCEDURE                       TUPR GMS RESECTED

C) MODULATION RX •

MOD'N_APPROACHES
1
2

INTRO FOR REPORT
    PROGNOSIS
TREATMENT PLAN              RX GOALS
    STUDY PERFORMED BY
                NURSE SPECIALIST
TEL         BIOMEDICAL ENGINEERING AND COMPUTER DIAGNOSTIC SUPPORT PROVIDED BY

FIG.40D

NAME:  
STUDY DATE:    8/3/98  
HOSPITAL NO.:

URODYNAMIC EVALUATION  
REFERRAL:

DEAR BUZZ:

THIS IS A 31 F WITH A PRESENTING COMPLAINT OF URINARY RETENTION AND INCREASED BLOOD CREATININE LEVEL X 3 WEEKS (PER PT). HX: KIDNEY TRANSPLANT 1989. THE FOLLOWING IS A SUMMARY OF THE URODYNAMIC FINDINGS.  ALL VALUES ARE SCORED 1 THRU 4 BASED ON VARIANCE FROM NORMAL TO PROVIDE A SEVERITY INDEX. RECOMMENDATIONS ARE PROVIDED AS A GUIDE TO MANAGEMENT. PLEASE FEEL FREE TO CALL IF YOU WOULD LIKE TO DISCUSS THIS CASE FURTHER.

RESULTS OF STUDY

CYSTOMETRY

THE OVERALL EFFICIENCY OF BLADDER STORAGE/EVACUATION WAS RATED AS BEING MINIMALLY (40%) ABNORMAL.

- STORAGE - THE MAXIMUM TOLERATED CAPACITY WITH FILLING WAS 345CC'S (N=4-500).

- SENSATION - FIRST SENSATION OF FILLING OCCURRED AT 270 CC'S AND A BLADDER PRESSURE OF 2CMH20. THERE WAS URGE ONLY APPRECIATION OF BLADDER DISTENSION ON FILLING THE BLADDER.

- COMPLIANCE - THE BLADDER PRESSURE WAS 6 CMH20 (N=O), PRIOR TO THE VOID ATTEMPT.  
THE COMPLIANCE CALCULATION WAS 11% ABNORMAL . THE SIGNIFICANCE OF THIS VALUE IS THEREFORE—NORMAL OR ACCEPTABLE.

- CONTRACTILITY - A MAXIMUM PRESSURE OF 9 CMH20 (N=<25) WAS OBTAINED WITH THE CONTRACTION LASTING 0 SEC.

- REFLEX INTEGRITY - DETRUSOR REFLEX BEHAVIOUR WITH THE VOID ATTEMPT WAS ABSENT.  
DETRUSOR REFLEX EXCITABILITY WAS FOUND TO BE 0 % GREATER THAN ACCEPTED NORMAL.  
THIS DEGREE OF REFLEX EXCITABILITY WOULD BE CONSIDERED CLINICALLY TO BE AREFLEXIC.

URETHRAL PROFILOMETRY AND PELVIC FLOOR EMG

- OUTLET RESISTANCE - THE FULL PROFILE LENGTH MEASURED 3 CM'S. THE OBSTRUCTING ZONE WAS 0 CM'S. THE FUNCTIONAL SPHINCTER ZONE WAS THEREFORE - 3 CM. (N=3-3.5)

- AVERAGE PEAK SPHINCTER PRESSURE. THIS WAS MEASURED AT 54 CMH20 (N=60-80).

- THE SHAPE OF THE PROFILE WAS CONSISTENT WITH A NORMAL (BELL SHAPE) POSTERIOR URETHRA.

- THERE WAS NO PAIN DISCOMFORT EXPERIENCED BY THE PATIENT TO THE INSERTION AND MOVEMENT OF THE CATHETER WITHIN THE EXTERNAL URETHRAL SPHINCTER ZONE.

- LEVATOR EMG NOT APPLICABLE

THE FOLLOWING DIAGNOSTIC IMPRESSIONS WERE SUGGESTED BY THE PROFILE:

A) THERE WAS NO SIGNIFICANT (0%) OBSTRUCTIVE COMPONENT.  
B) THERE WAS NO SIGNIFICANT (4%) SPASTIC DYSFUNCTION OF THE EXTERNAL URETHRAL SPHINCTER.  
C) THERE WAS MINIMAL (16%) RISK OF STRESS URINARY INCONTINENCE.

FIG.40E

RESULTS OF UROFLOWMETRY

THE PATTERN OF UROFLOW OBTAINED WAS RATED AS BEING 102 % DEVIATION FROM NORMAL.

THE FLOW RATE DATA OBTAINED WAS AS FOLLOWS:

- PEAK FLOW - 3.8 CC/SEC (N=>25).
- AVERAGE FLOW - 2.1 CC/SEC (N=>12.5).
- POST VOID RESIDUAL - 321 CC (N=<15).
- THE VOLUME VOIDED WAS - 24 CC S (N=4-500).
- THE TOTAL STORAGE VOLUME OF THE BLADDER WAS THEREFORE 345CC (N=4-500).
- THE BASIC PATTERN OF THE VOID WAS THAT OF A - DRIBBLE OR INSIGNIFICANT FLOW.
- THE MAIN VOIDED STREAM WAS - CHOPPY.
- TERMINATION OF THE STREAM WAS ASSOCIATED WITH - POST VOID VOIDING.

A VOIDING CYSTOURETHROGRAM (VCUG) AND A CYSTOSCOPY SHOULD BE PERFORMED TO COMPLETE THIS PATIENTS EVALUATION.

DIAGNOSTIC IMPRESSIONS

THE FINDINGS ARE MOST CONSISTENT WITH A WORKING DIAGNOSIS OF ACONTRACTILE BLADDER AND SPHINCTER - RETENTION.
ADDITIONAL FACTORS TO BE CONSIDERED IN MANAGEMENT ARE:
POOR PELVIC MUSCLE CONTROL.
THE SYMPTOMS EXPERIENCED BY THE PATIENT WOULD BE BASED LARGELY ON FACTORS THAT ARE POSSIBLY NEUROLOGIC.

FIG.40F

RECOMMENDATIONS RE TREATMENT

THE STUDY WAS PERFORMED BY     NURSE SPECIALIST.

SUPERVISION AND STUDY ANALYSIS BY

DYSFUNCTIONAL PATTERNS
SCORE
1 • MATTERHORN
0 • BELL
2 • WIMP 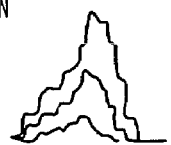

FLOW PATTERNS
0 • SMOOTH ⌒
1 • SAWTOOTHING ⌒⌒⌒
2 • CHOPPY/UNDULATING ⌒⌒ ⌒⌒
3 • BROKEN/INTERMITTENT ⌒⌒⌒
4 • NO FLOW ____

OBSTRUCTIVE PATTERNS
TERRACING

MOGUL VS CAMEL BACK
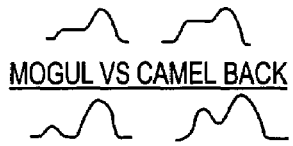

FLOW CURVE ARCHING
0 • BELL
1 • ROMAN
2 • BRIDGE
3 • PLATEAU
4 • NONE
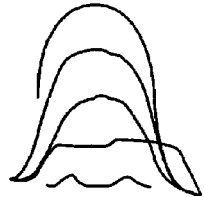

SPHINCTER EXCITABILITY
• SENSITIVITY
    DISCOMFORT=NONE, MILD, MARKED
• REFLEXIVITY

FIG.40G

METHOD AND SYSTEM FOR DIAGNOSIS OF LOWER URINARY TRACT DYSREGULATION AND RELATED CONDITIONS

CROSS REFERENCE TO RELATED APPLICATIONS

This application claims priority to U.S. provisional application No. 60/232,280 entitled "Method for Diagnosis of Lower Urinary Tract Dysregulation and Related Conditions," filed 13 Sep. 2000 (the '280 application). The '280 application is hereby incorporated by reference as though fully set forth herein. This application is a national stage filing pursuant to 35 U.S.C. § 371(c) of international application no. PCT/US2001/028509 filed 13 Sep. 2001 entitled "Diagnosis of lower urinary tract dysregulation."

BACKGROUND OF THE INVENTION

1. Field of the Invention

The present invention relates to a diagnostic system for lower urinary tract dysregulation and related conditions. The invention specifically concerns the provision of diagnoses and recommended treatments of lower urinary tract dysregulation and related disorders through the computerized comparison and interpretation of urethral pressure profiles and other lower urinary tract data.

2. Description of the Related Art

Over the past decade, the urethral pressure profile (UPP) has become less popular as a diagnostic tool for urinary incontinence. There are several publications that have noted very poor correlation between the diagnosis of incontinence and peak urethral pressures. Some of these papers are, for example, G. Lose, *Urethral Pressure Measurement*, 166 Acta. Obstet. Gynecol. Scand. Suppl. 39 (1997); S. Meyer, et al., *Urodynamic Parameters in Patients with Slight and Severe Genuine Stress Incontinence: Is the Stress Profile Useful?*, 13(1) Neurourol. Urodyn. 21 (1994); E. Versi, *Discriminant Analysis of Urethral Pressure Profilometry Data for the Diagnosis of Genuine Stress Incontinence*, 97(3) Br. J. Obstet. Gynaecol. 251 (1990); M. C. de Jong, et al., *The Static Urethral Pressure Profile in Female Incontinence: A Comparison Between Sphincter and Detrusor Incontinence*, 78 Prog. Clin. Biol. Res. 231 (1981). The conclusion of these authors has been that measurements obtained through a UPP add little value to the work-up of an incontinent patient. On the other hand, many published articles reference and document the phenomenon of urethral instability. The role of urethral instability, unlike detrusor instability, however, has remained undefined both in terms of its contribution to symptoms and defining an approach to treatment.

SUMMARY OF THE INVENTION

Contrary to the negative press on use of the UPP, the performance of a UPP in combination with further measurements of urethral instability provides a valuable tool for diagnosing and treating urinary incontinence. Further, quantifying the objective results of these tests along with subjective patient feedback allows for comparison of results with known norms or a known body of data to return a probable diagnosis and appropriate treatment. Base upon the known norms, or, in particular applications, once the collected data has reached the point at which a quantifiable scale can be developed, a processing means, such as a computer with an appropriate software program, may be used to reliably and consistently compare individual patient data with stored parameters and, by calculation, render a diagnostic opinion. This opinion may be weighted to provide a guide to the urgency of care and appropriate treatments. Further, if the system is used to collect data during and after treatment, the system can eventually provide prognosis information to clinicians.

Incontinence can result from anatomical failure of either the bladder (e.g., poor compliance) or the urethra (e.g., radiation or iatrogenic injury of the sphincter). Similarly, incontinence can result from behavioral dysfunction of either the bladder (instability) or the urethral sphincter (e.g., weakness, dynamic failure, spasticity, reflex relaxation, or triggered voids). It is important to design the urodynamic evaluation to identify and separate anatomical causes from behavioral at either or both the bladder and sphincter levels. It also makes sense to treat behavioral dysfunction prior to the anatomical failure for the simple reason that the former responds to less risky therapies, medication, and modulation principles. These therapies are also far less expensive than surgical solutions. Surgical options, given their risk for failure and cost, should preferably be explored only after behavioral approaches have successfully modulated the excitability within the sacral root reflexes. Only in this manner can treatment of incontinence address the full scope of the problem.

Traditionally, the causes of urinary incontinence are classified as either urge, stress, or a mixture of the two. However, there is no system in place to measure the relative proportions these causes play in particular circumstances of incontinence. On a simple level, these classifications refer to either detrusor instability or weakness of the urethral sphincter. Treatment based on this approach becomes a simple choice between an anticholinergic for the detrusor instability and bladder suspension for all other problems. This would indicate that, with the exception of detrusor instability, all other causes of incontinence are rooted in an anatomical deficiency rather than, for example, in neural dysregulation. Further, because there is no strong understanding of the proportional mixture of the causes of the problem, there is no clear direction as to what combination of treatment approaches to consider.

The problem with the weakness theory is that there is no correlation between peak urethral pressures and leakage. This is not surprising, as behavior rarely correlates in absolute terms with anatomical appearance. Hence, patients can be in retention with a urethral pressure of 20 cm-$H_2O$, or leaking with a urethral pressure of 90 cm-$H_2O$. Likewise, patients can be in retention with a secondary cystocele, or leaking in the absence of significant cystocele. The explanation for these seemingly incongruous situations may be found by studying and recording the behavior of the storage reflexes.

In contrast, the present system of incontinence classification as Type I, II, or III cannot account for these paradoxes. It is important that the stability, excitability, trigger threshold, relaxation, and other elements of storage reflexes be factored into the diagnosis and treatment of urinary incontinence. Recording the peak urethral pressures, i.e., a snapshot reading of urethral closure, provides no information regarding the behavior of the urethral sphincter; i.e., the stability of those pressures.

There are two types of information needed by the clinician: first, does the sphincter have competence or sufficient closure capability to maintain continence; and second, does the sphincter have the neurological competence to function in a predictable manner without pain or irritation. On one level the clinician requires information about anatomical resistance. On another level, however, information is needed as to the state of excitability within the sphincter.

The urethral sphincter is a dynamic muscle. Activity within the sphincter must adapt to different activity states: storage vs. evacuation; changing levels of bladder fullness; multiple postures; and a variety of states of physical activity, for example, sitting, standing, walking, and running. Sphincter activity is also connected with states of anxiety and stress. A sphincter that is reactive, behaviorally brittle, prone to precipitate relaxation, or unstable, is more likely than not to exhibit higher pressures on the standard UPP. An exaggerated response to moving a catheter through the urethra is to be expected if the urethral sphincter is hypersensitive or slightly spastic. Precipitous relaxation of the urethra may or may not be associated with disinhibition of the detrusor or facilitation of a detrusor contraction. Leakage episodes may be present in any of these circumstances. Evaluation of a single parameter, e.g., peak closure pressure, is therefore a very narrow snapshot of the urethral dynamic.

However, a UPP performed in the manner described herein, provides a more complete picture of the factors contributing to incontinence. Further, the various states and measurements recorded, when quantified, provide a valuable tool in the evaluation of the incontinent patient. The present invention employs a computer interface to implement a quantification scheme, calculate values associated with different diagnostic factors, and return a likely diagnosis and treatment program for urethral incontinence. The program may be implemented on a stand-alone desktop computer, personal digital assistants, over local or wide area networks, or a global computer network such as the Internet, including the World Wide Web portion of the Internet.

A combination of objective information from the UPP, physical evaluation, patient history, and subjective symptomatic information as described by the patient is entered by the clinician into the program. The program assigns numeric values or scores to the information. The numeric values are based upon known norms and/or databases of collected patient profiles of known pathology for which discrete signs and symptoms have been cataloged, classified, and accorded numeric valuation schemes. Through a comparison of the numeric values, assigned to a particular patient's presentation, to parameters established in the program based upon norms and collective patient data, a pathological profile is generated and cross referenced to the attendant diagnoses and treatments.

The proffered diagnosis and related treatment recommendations may be available to the clinician through the computer's graphic, textual, or other interface, or they may be downloaded to a file from a network or over the Internet, or printed to be included in the patient's paper record. The computer diagnostic program may likewise be stored on a server for network access by multiple clinicians or it may employ an HTML interface for access over the World Wide Web. In the disclosed embodiment, the computer program is created using a standard database software package employing Boolean logic. However, any programming language or software/hardware platforms may be substituted.

Use of a database software program for programming the computer diagnostic system allows for the retention of specific patient information for subsequent review or archiving. In addition, the database embodiment allows for categorized searching of patients in the database with similar profiles for researching conditional norms and for generating statistical summaries. Statistical reporting is highly valuable for tracking the effectiveness of treatment alternatives, such as surgical procedures or drug trials.

The invention disclosed herein provides a method for diagnosing lower urinary system conditions by receiving urodynamic data and subjective symptomatic impressions concerning a patient. The method then assigns weighted point values to the urodynamic data and the subjective symptomatic impressions, quantifies norms for lower urinary system function, as a whole or in part, and quantifies recognized pathologies of lower urinary system conditions as degrees of departure from the norms. The method then determines a lower urinary system condition diagnosis of the patient, as a function of the degrees of departure from the norms by invoking a set of rules to compare the weighted point values assigned and the quantified norms. The method then reports the lower urinary system condition diagnosis, treatment recommendation, or further diagnostic suggestions. The method may add additional types of diagnostic data to the calculations, for example, ultrasound data showing prostate size, or other data that may be related to lower urinary tract dysregulation. Such other data may be related to, for example, reproductive systems, gastro-intestinal systems, or conditions such as TMJ, carpal tunnel syndrome, fibromyalgia, or other syndromes with established neurological linkages to the lower urinary system. The method may base its norms on averages of a plurality of patient data collected over time.

The method may also provide a treatment ladder in step with the severity level. Such a treatment ladder can be established once a significant base of both pre- and post-treatment data is available. By comparison of patient conditions before and after treatment, the efficacy of treatments for particular severities of conditions can be offered as a ladder of treatments with an appropriate efficacy-to-risk ratio as related to the particular condition. One particular treatment ladder might include control of the condition by medication on one end, to electrical stimulation, to neurotoxins, to insertable devices, and to reconstructive surgery on the other end. The method may further provide for determining the efficacy of treatment trials, or merely the efficacy of the treatment of a particular patient.

Once a significant database is developed, the program will be able to select an appropriate battery of tests or treatments narrowly focused to the condition of the patient. The program will help prevent unnecessarily invasive tests or treatments. Further, additional types of testing beyond, for example, the urethral pressure profile, may be tracked alongside the diagnostic tools discussed herein to determine whether these tests offer any efficacy in diagnosis with less invasiveness. For example, perhaps functional MRI or pelvic floor x-ray data may one day be used with as much accuracy to diagnose prostate problems. By tracking the results of such testing along with the known results provided by the instant program, quantification of any additional diagnostic capabilities of these tests can be determined.

In another aspect of the invention, a system for diagnosing lower urinary system conditions is provided that combines a system input, a memory, a processor, and a system output. The system input receives urodynamic data and subjective symptomatic impressions concerning a patient. The memory stores norms of lower urinary system function, as a whole or in part quantified as numeric scores; degrees of departure from the norms, which quantify recognized pathologies of lower urinary system conditions; and a set of rules for processing the urodynamic data, the subjective symptomatic impressions, the norms, and the degrees of departure. The processor, using the set of rules, determines a urinary system condition diagnosis of the patient by assigning the weighted point values to the urodynamic data and the subjective symptomatic impressions and, as a function of the degrees of departure from the norms, compares the weighted point values to the numeric scores. Finally, the system output reports the lower urinary system condition diagnosis determined.

In yet another aspect of the invention, a computer program product, for example, computer software with program code, is provided that accepts input of urodynamic data and subjective symptomatic impressions concerning a patient. This input can be local to the computer or over a communication network from a client machine. The program code may effect an assignment of weighted point values to the urodynamic data and the subjective symptomatic impressions, a quantification of at least norms for lower urinary system function, as a whole or in part, and quantification of recognized pathologies of lower urinary system conditions, as degrees of departure from norms. The program code may also cause the computer to effect a determination of a lower urinary system condition diagnosis of the patient, as a function of the degrees of departure from the norms by invoking a set of rules to compare the weighted point values assigned to the norms. The program code may direct the results to be output by the computer locally or over the network to be received by the client machine.

In a further aspect of the invention, a communicative grading system for lower urinary system conditions is provided. The grading system is classified in terms of urethra characteristics and bladder characteristics, wherein the urethra characteristics and the bladder characteristics are measured in levels of the qualities of tone, reflex excitability, and sensation.

BRIEF DESCRIPTION OF THE DRAWINGS

FIG. 31 is a representation of elements considered in scoring the cystometrogram characteristics of void triggers.

FIG. 32 is a representation of elements considered in scoring cystometrogram characteristics of sensation.

FIG. 33 is a representation of elements considered in scoring cystometrogram characteristics of compliance.

FIG. 34 is a representation of general categories considered in scoring flow related data.

FIGS. 40A-G together comprise an automatically generated diagnostic report and recommendation letter output by the invention.

DETAILED DESCRIPTION OF THE INVENTION

Figure 41:
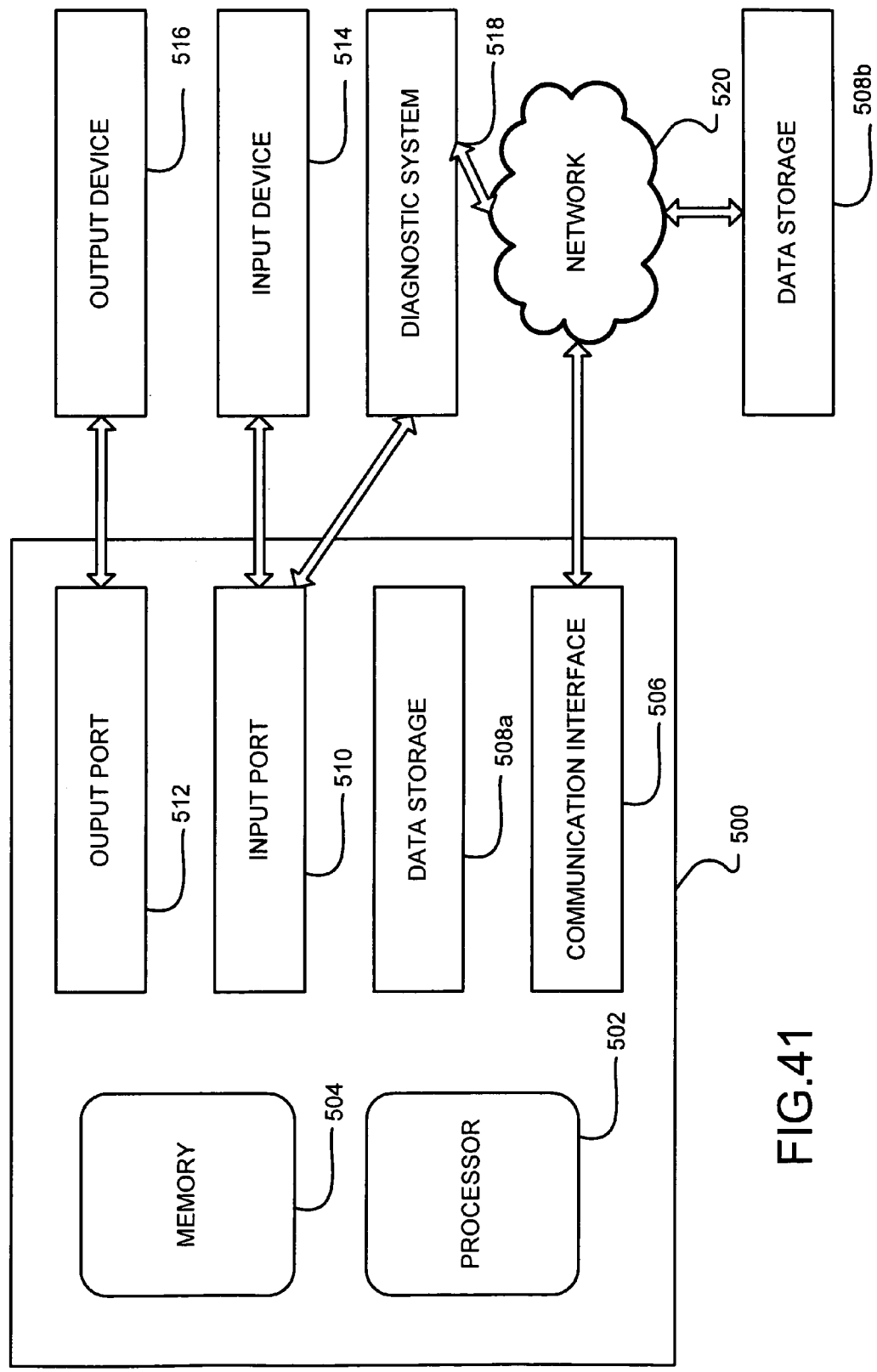
FIG. 41 is a schematic diagram of an exemplary computer system for implementing a diagnostic program of the present invention.

The UPP diagnostic program of the present invention may be performed by software executed on a computer system 500 as shown in FIG. 41, for example, a personal computer, including, for example in an environment requiring greater mobility, on a personal digital assistant (PDA). The computer system 500 has a processor 502 and memory 504 that together execute the diagnostic program. The program may be used in combination with urodynamic diagnostic systems 518, for example, a Duet MultiP by Medtronic of Skovlunde, Denmark, porting data directly as it is measured, or the data may be entered into the program manually during or after a clinical examination. The computer 500 may be stand-alone or a workstation connected via a communication interface 506 within a communication network 520. The diagnostic program requests both objective and subjective symptomatic and diagnostic input, for example, via graphical, textual, audial, or other input devices 514 via an input interface 510, in order to assign values under a quantification scheme, determine indicators based upon rules, and render appropriate differential diagnoses and treatment programs for detrusor and urethral related conditions. Data storage 508*a*, 508*b* may be local to the computer or accessed via the communication interface 506 from one or more repositories connected to the computer 500 via a communication network 520.

The program may also be implemented on the computer system 500 within an application service provider (ASP) platform for access by users over the communication network 520. Use of an ASP platform may provide, for example, an HTML user interface with the program stored on a server via World-Wide-Web pages over the Internet, thereby allowing simultaneous use by multiple clinicians. Multiple simultaneous access may also be provided by other types of known client-server networks. Examples of the communication network 520 include local area networks and wide area networks, both public and private, telephone and cable networks, intranets, and the Internet. The software may be stand-alone or may be a logic program created within a hierarchical, relational, or other database application. The proffered diagnoses and related treatment recommendations are available to the clinician through the computer's graphical, textual, audial, or other output devices 516 via an output interface 512, or they may be downloaded to a file from the network 520 or over the Internet, or printed to be included in the patient's paper record.

In one embodiment, as disclosed herein, the computer program is created using a standard database software package executed from the memory 504 of the computer system 500 employing data entry fields and Boolean logic. However, any programming language or software/hardware platforms may be substituted to implement the rules upon which the diagnostic program operates. Please note that the database logic flow chart depicted in FIGS. 1-16 includes 1 and 2 digit encircled numbers. These encircled numbers represent outputs from the diagnostic system 518 to the input port 510 of the computer system 500 and jump markers for the input of that data into a future function. All reference numbers used in this specification to refer to elements in FIGS. 1-16 are 3 digit numbers and are not encircled.

Figure 1:
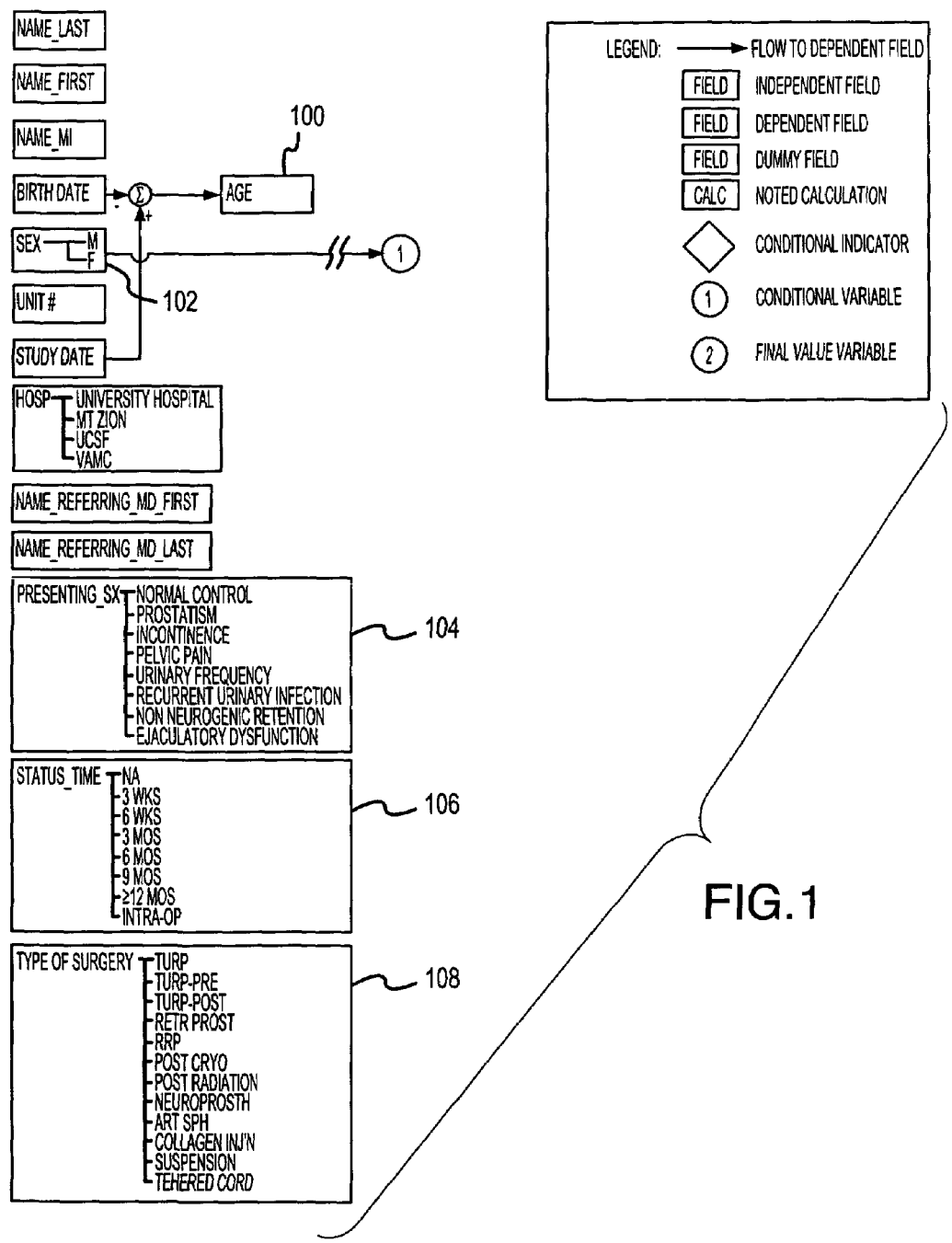
FIG. 1 is a portion of a database field chart depicting fields related to patient background information.

As with typical examinations, general background information regarding the patient, such as name, record number, date of examination, and referring physician, is entered as shown in FIG. 1. The age, field 100, and sex, field 102, of the patient are specifically recorded as they dictate differential values to be recorded during the examination, which ultimately impact the appropriate differential diagnosis. Additional information for patient identification, report generation, and other tracking purposes may also be recorded in appropriate fields at this time.

Next, patient history information is recorded in the UPP diagnostic program. Appropriate history information may include the following: associated diagnoses, presenting symptoms, field 104, including the neurogenic status (i.e., whether or not the presenting symptoms, field 104, are neurologically based), related procedures or surgical treatment, field 108, whether the patient's status is pre- or post-operative, and time pre- or post-performance of a procedure, field 106. The UPP diagnostic program preferably allows a primary and secondary choice among the presenting symptoms, field 104, and should at a minimum offer choices of incontinence, pain, frequency, and retention. Associated diagnoses may reflect, for example, multiple sclerosis, Parkinson's disease, cerebral vascular accident, post cerebral vascular accident, partial spinal injury, spinal trauma, tumor, cerebral vascular accident, Alzheimer's disease, diabetes, peripheral neuropathy, head injury, hydrocephalus, and spina bifida. Similarly, treatment procedures may include, for example, the following: boot, capsaicin bladder, electrode implant, peripheral nerve evolution, collagen, artificial sphincter, pre transurethral prostatectomy, post transurethral prostatectomy, prostate resection, radical prostate resection, urinary diversion, post cryosurgery, post radiation, neuroprosthesis, bladder suspension, and tethered cord release.

Such patient history information, including presenting symptoms, field 104, and procedures or surgical treatment, field 106, is highly relevant to discerning between differential diagnoses and treatments when processing the examination results. These history fields also allow for categorized searching of patients in the database with similar profiles and for generating statistical summaries. Statistical reporting is highly valuable for tracking the effectiveness of treatment alternatives, such as surgical procedures or drug trials. Additionally, a further field for textual entry of a narrative history may be provided, for example, for inclusion in a computer-generated letter to the referring physician summarizing the diagnostic findings of the UPP diagnostic program.

Figure 18:
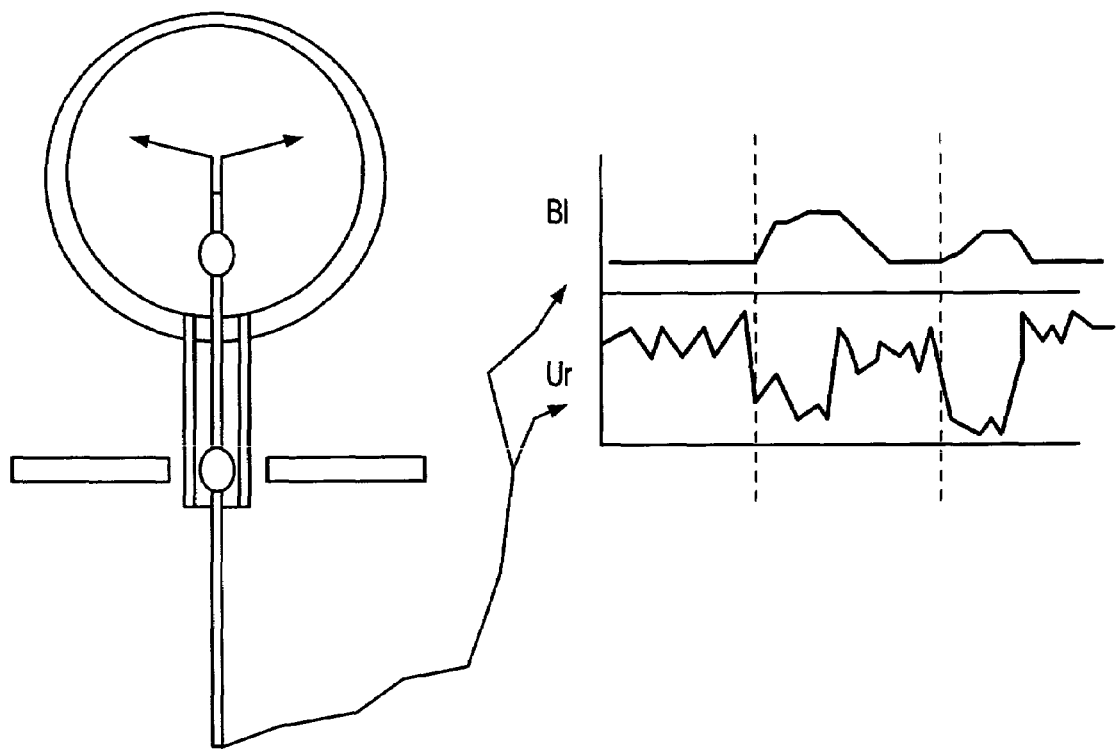
FIG. 18 is a representation of the recordings taken using an urodynamic methodology.

In the clinical setting, the primary urodynamic study is performed with the patient supine. A rectal catheter is used to monitor rectal pressures and the rectal electro-myography (EMG). A microtip catheter is then inserted into the urethra. The bladder is filled to 50 cc to imitate a substantially empty bladder condition and the microtip catheter is withdrawn in short steps while multiple recordings of urethral pressure are taken. Standard parameters of peak pressure and functional length are recorded. A representation of the UPP is shown in FIG. 18. Sensation and reactivity of the sphincter along the functional length are then quantified using both subjective and objective scales. UPP readings are again taken in a similar fashion with the bladder filled to a volume of approximately 200 cc, or slightly greater than fifty percent (50%) of capacity. The intent is to obtain recordings of outlet activity at various fill volumes to reflect different neurological states.

It is noted that in addition to, or in substitution for, microtip catheterization, which is typically used to record the UPP, EMG recordings associated with the urinary tract could be undertaken. In this instance, instead of measuring pressure fluctuations, microvolt excursions resulting from the neuromuscular activity of the various fill and void states may be recorded. These electrical readings can imply the pressure and reflexivity measurements of the UPP and can similarly be categorized and weighted according to the methodologies of the program disclosed herein to provide diagnosis and treatment recommendations for urinary tract dysfunction. Other data recording methods such as radiology, ultrasound, motor sensory evoked response activity, electromyographic recordings, magnetic resonance tomography, computed tomography, nuclear, and other imaging techniques could likewise be used to make appropriate pressure and reflexivity measurements.

The data collected in and processed by the UPP diagnostic program can be generally divided into three different assessment phases. The first concerns observation and examination of urethra characteristics; the second concerns similar diagnostics of the bladder; and the third involves data related to the flow rate of fluid in the system.

Urethral Assessment

With regard to the urethral analysis, the following information may be collected concerning the patient and entered into the UPP diagnostic program: sphincter tone, sphincter reflex excitability, sensitivity, urethral length (including obstruction vs. weakness), anatomical distortions, and subjective impressions.

a) Sphincter Tone

Figure 2A:
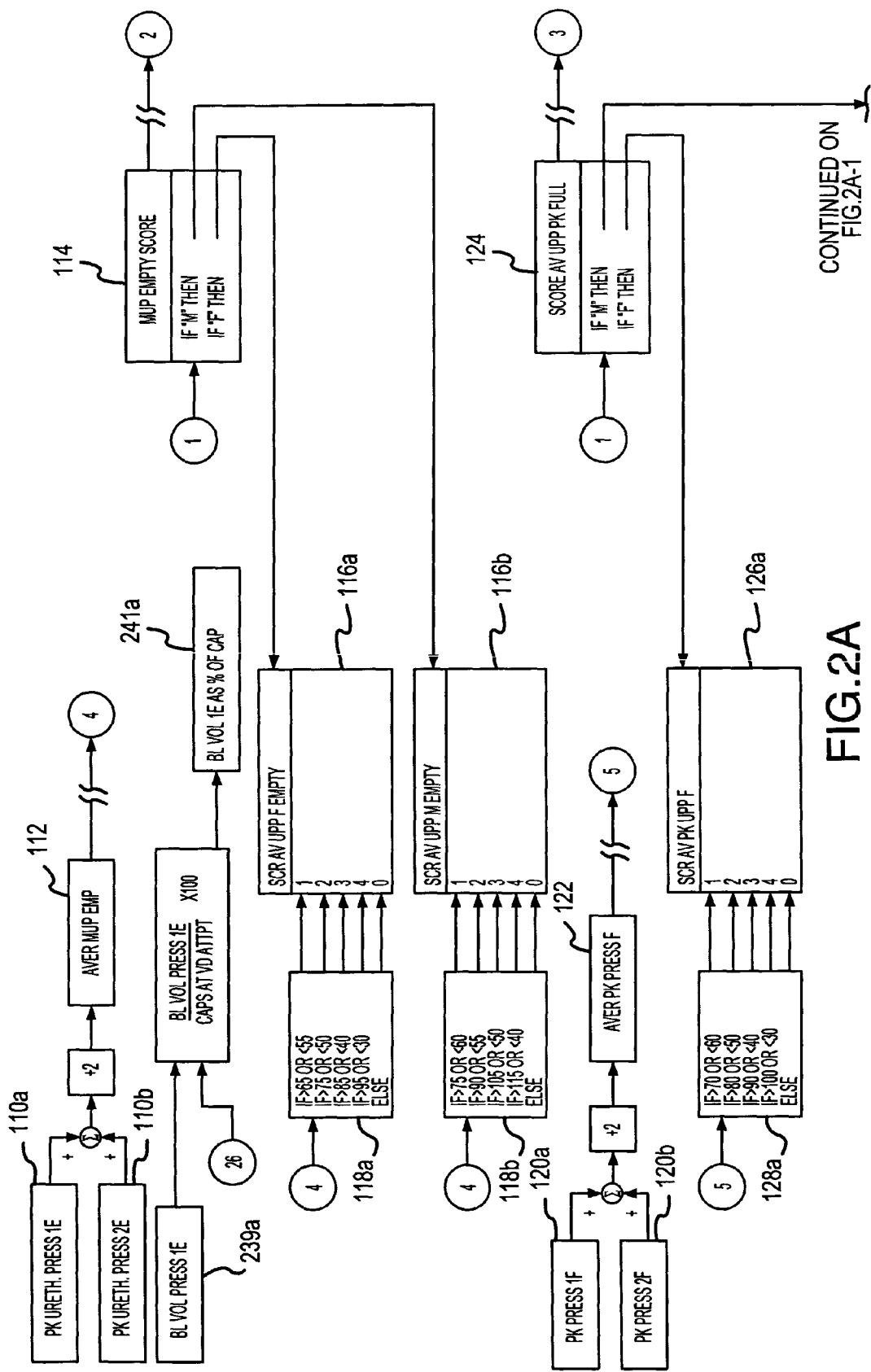
FIGS. 2A-2C comprise a portion of a database field chart depicting fields related to urethral dynamics and measurements.
Figures 1, 2A:
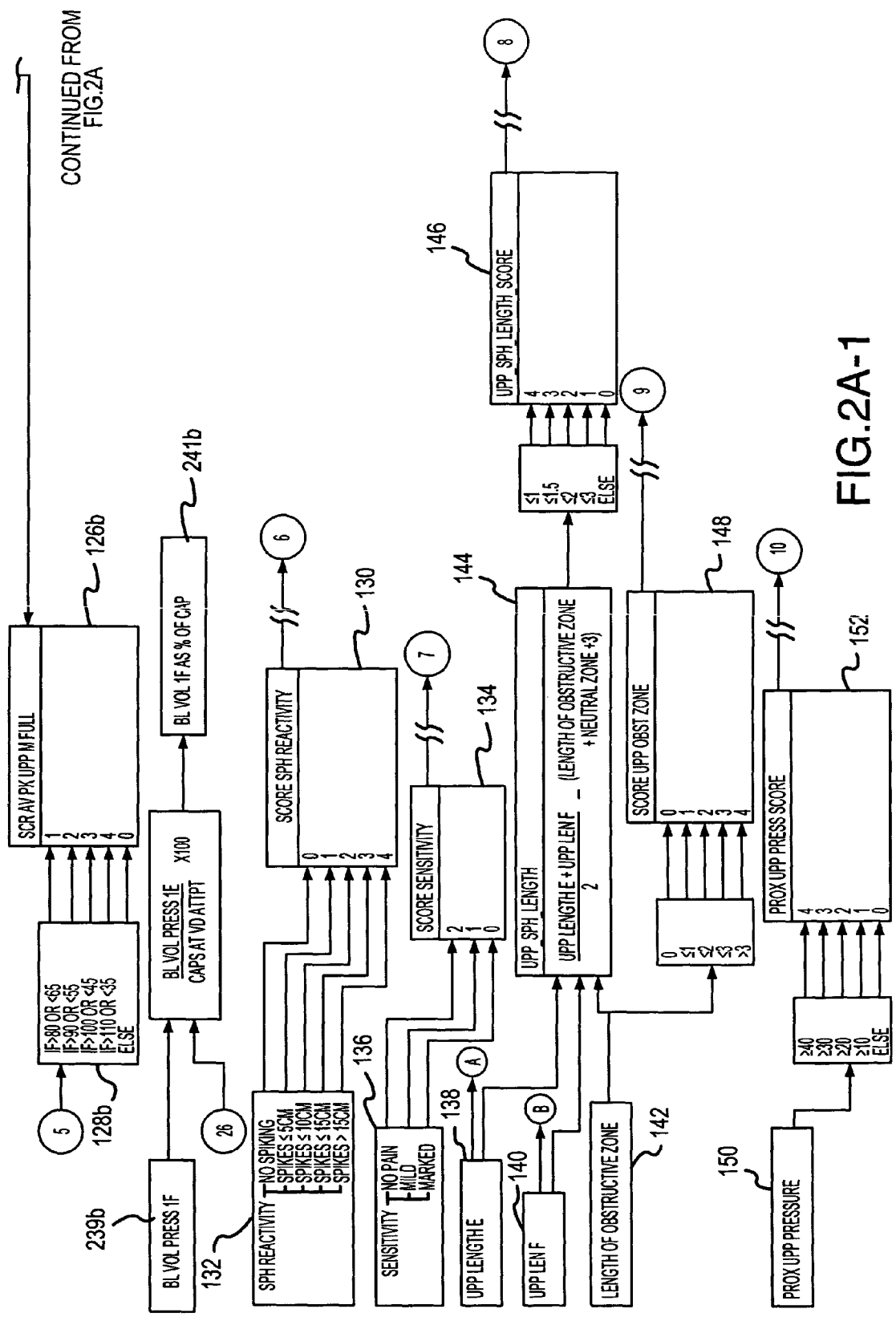
Figure 2B:
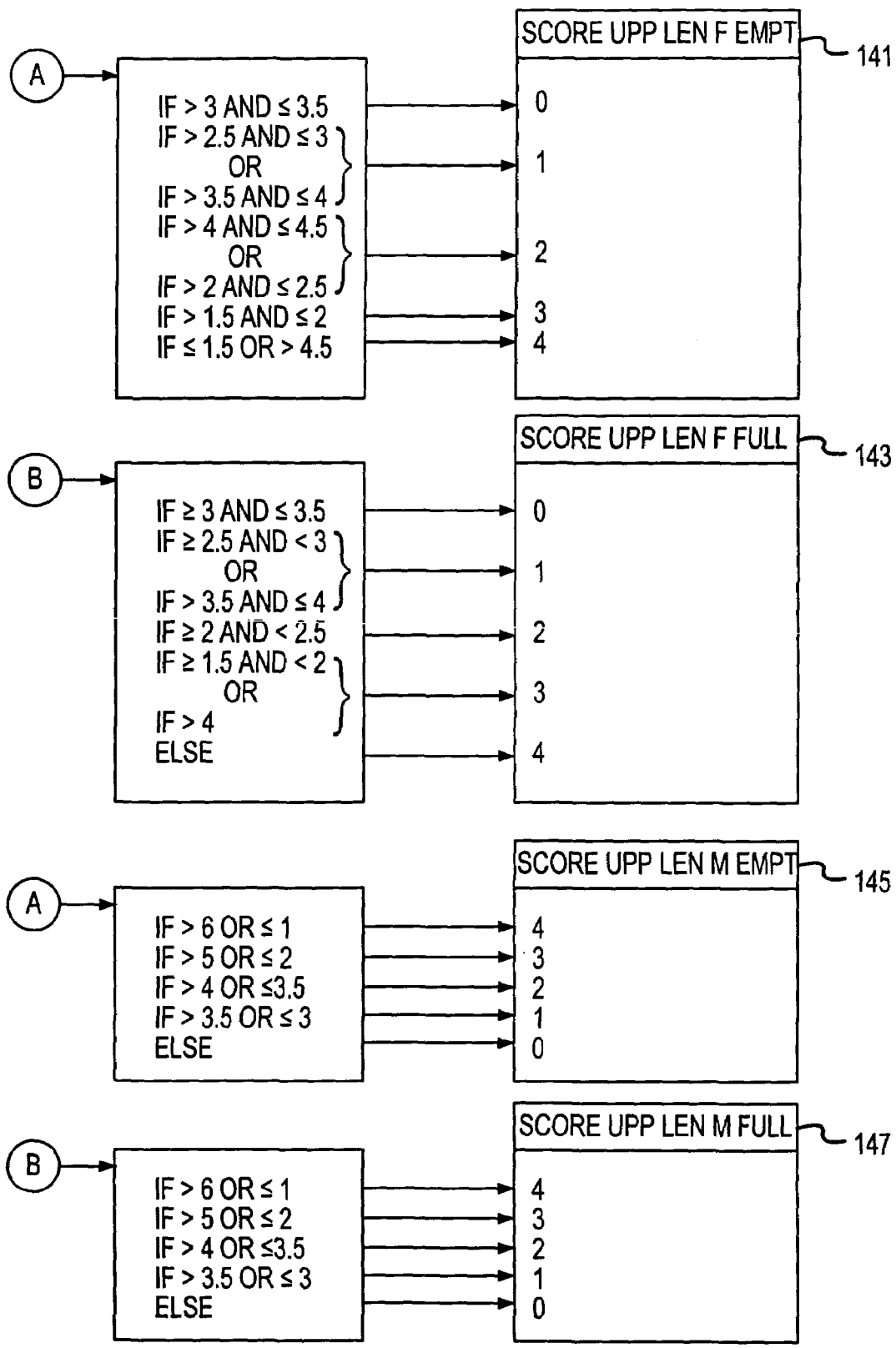

Peak sphincter closure tone may be assessed with the bladder both empty and full for both static and dynamic characteristics. Dynamic impressions, which are the subject of the following readings, can be further characterized as either reflexive, as during filling or void, or spontaneous. As seen in FIG. 2A, multiple readings of peak urethral pressure are taken in an empty bladder condition, fields 110a and 110b. An empty bladder is considered a bladder that is less than half full. These readings are averaged together to arrive at an average peak urethral pressure for the empty bladder, field 112. The average peak urethral pressure is then compared to known diagnostic ranges, fields 118a and 118b, and allocated a corresponding numeric score based upon the range into which it falls, field 114. There is diagnostic significance in the ranges of peak pressure between males and females, so the allocation of numeric scores must be separated between the sexes. The score held in field 114 is taken from either field 116a or 116b, based upon the ranges defined in fields 118a and 118b, respectively, which are dependent upon whether the patient is female or male.

Similarly, peak sphincter closure tone may be measured with the bladder greater than half full in fields 120a and 120b. These readings are likewise averaged in field 122 and translated into a score in field 124. The score in field 124 is taken from either field 126a or 126b in consideration of the sex of the patient as the ranges are set forth in fields 128a and 128b. The scoring methodology assesses 1 point for every 10 cm-$H_2O$ change above or below baseline. A score of 0 reflects ranges encompassing accepted normal baselines of 55-70 cm-$H_2O$ for females and 65-80 cm-$H_2O$ for males. The female baseline is set 10 cm-$H_2O$ below that for men because of a lower muscle mass. Scores above baseline indicate a measure of sensory motor-neural upregulation (spasticity), while scores below baseline reflect a measure of sphincter weakness, either muscular or neural-muscular compromise. The data collected regarding peak urethral pressures is later used by the UPP diagnostic program for determination and diagnosis of urge incontinence, stress incontinence, urinary retention, and various pain syndromes.

Figure 19:
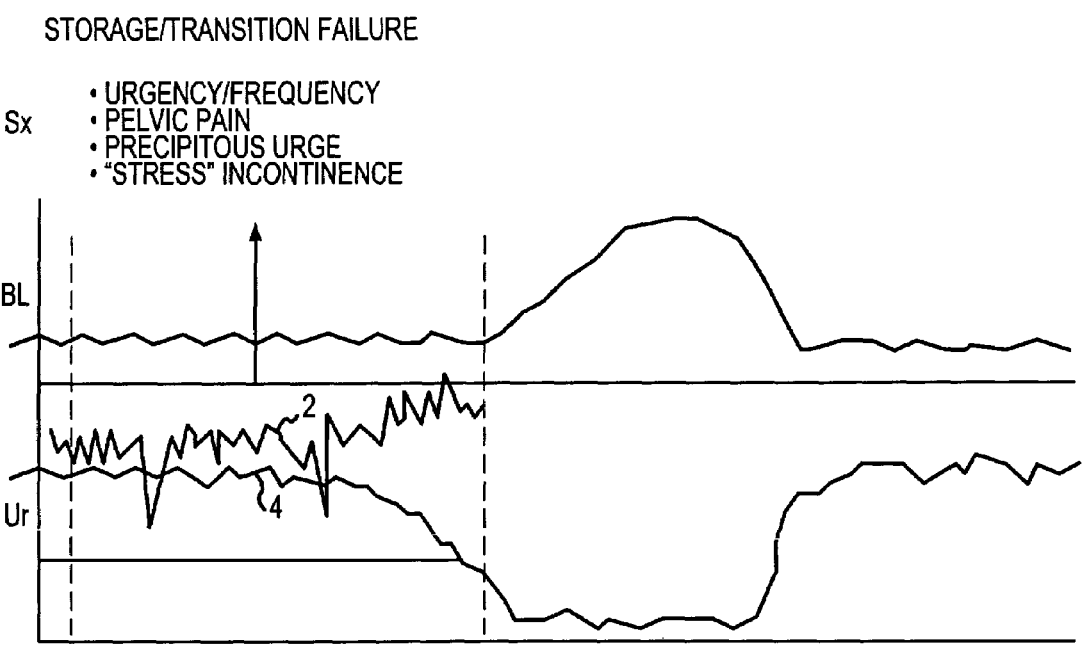
FIG. 19 is a urethral pressure profile graph depicting indicators of storage and transition failures.

The UPP graph in FIG. 19 shows several conditions that lead to storage regulation failure or problems with transition to the void phase (if void is possible at all). These states are shown with reference to the transition phase, but can exist in the storage phase as well. (See FIG. 20 for a representation of all the void phases.) The jagged line 2 represents the urethral pressure due to sphincter contraction conditions such as urgency, precipitous urge, and pain. The relatively smooth line 4 represents a condition of stress incontinence. These pressure profiles are more clearly presented in FIG. 21.

Figure 21:
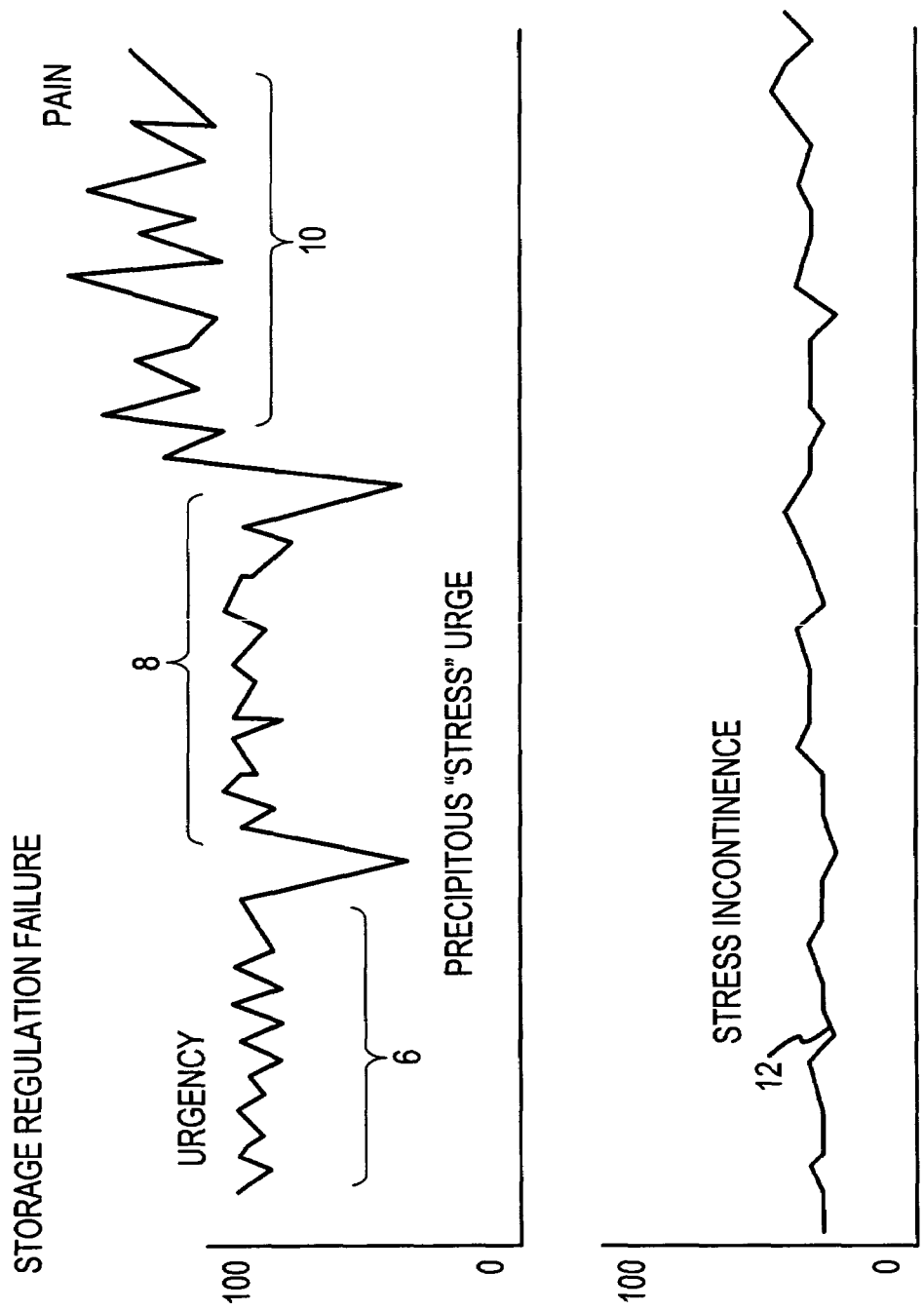
FIG. 21 is a urethral pressure profile graph depicting indicators of storage regulation failure.
Figure 22:
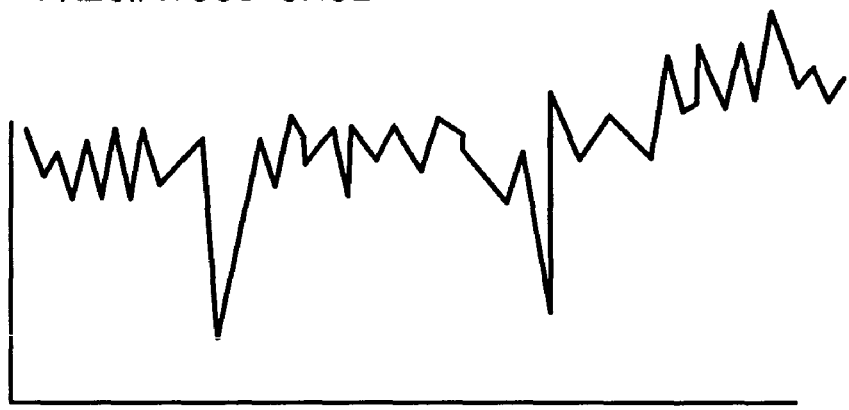
FIG. 22 is a representation of multiple symptoms of storage regulation failure.

Continued sphincter contraction creates high pressure 6, as shown in FIG. 21, in the urethra preventing the ability to void even though the urgency to void is present. A second condition, precipitous stress, is characterized by sharp, spastic releases 8 in sphincter contraction and thereby lower urethral pressure resulting in instances of incontinence. However, the sphincter quickly contracts again and the urge without void returns. A third condition is characterized by extremely high urethral pressure 10 that prevents void and is accompanied by pelvic pain. Stress incontinence, on the other hand, is characterized by constant weak sphincter contraction 12 and thereby constant leakage and the inability to regulate storage. As depicted in FIG. 22, these regulation failure conditions can be present during bladder filling as well.

b) Sphincter Reflex Excitability

Figure 23:
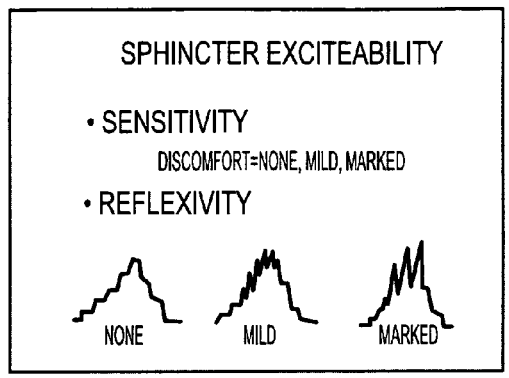
FIG. 23 is a representation of multiple methods of measuring of sphincter excitability and degrees thereof.

To determine whether the sphincter is hyperactive, the reflex contraction force, above baseline, of the sphincter to movement of the recording catheter in the urethra is measured and scored. The UPP diagnostic program compares the reflex excitability of the urethra to defined ranges, field 132 (FIG. 2A), and calculates a score. FIG. 23 shows a graphic representation of reflexivity patterns that translate to the defined ranges. The score is 1 point for each 5 cm-$H_2O$ change above baseline with bladder less than half full. Measurements are taken in the empty bladder state because damping of the reflex may occur with the full bladder. Score values for sphincter reflex excitability, field 130, range from 0-4. The data collected in this measurement is later used by the UPP diagnostic program for calculation and diagnosis of urge frequency, urinary retention, and various pain syndromes.

c) Sensitivity

The degree of discomfort experienced by the patient during the recording of urethral pressures is subjectively assessed by the clinician, entered into the UPP diagnostic program, and scored from 0-2, field 134 (FIG. 2A). The hypersensitivity score is based on no pain, mild pain (admission when asked), and severe pain (withdrawal by the patient), field 136. A more accurate scoring scale could be used if sensory thresholds were to be quantifiably gauged (e.g., by use of a neurometer). The UPP diagnostic program later uses the data collected regarding sensitivity for diagnosis of all related pain syndromes.

d) Urethral Length (Obstruction vs. Weakness)

Measurements of the length of the urethral sphincter section are made by the clinician with the bladder empty, field 138 (FIG. 2A), and greater than half filled, field 140, to reflect the opening of the bladder neck with the stretching of the bladder sidewalls as the bladder is filled. Any obstruction in the urethra between the bladder neck and external sphincter and scarring which impacts the sphincter closure are also measured, field 142. Deviations from normal urethral lengths in both the empty and full bladder states are scored separately in FIG. 2B for women in fields 141 and 143, and men, fields 145 and 147, respectively.

Recorded measurements should be representational. Therefore the clinician may need to confirm the reading before entering a measurement into the database. The UPP diagnostic program later uses the data collected regarding urethral sphincter length for calculating obstruction, spastic dysfunction, and stress incontinence diagnoses.

e) Anatomical Distortions

Measurements in fields 138 and 140 that indicate a reduced sphincter length reflect anatomical abnormality that is separately scored. Abnormality in sphincter length is determined in field 144 (FIG. 2A) by first adding the lengths of any obstructive zones in the urethra to the lengths of the neutral zones, plus a normal sphincter length of 3 cm. This sum is then subtracted from the average of the urethral lengths measured at empty and full bladder conditions, fields 138 and 140. Abnormalities in sphincter length are then scored from 0-4 by adding 1 point for each 0.5 to 1 cm increment under 3 cm, field 146.

The length of the obstructive zone is similarly translated to an obstructive zone score on a scale of 0-4 corresponding to 1 cm increments of obstruction, field 148. The degree of obstruction is also reflected in occlusion pressure of the obstructive area, field 150. The occlusion pressure is scored as 1 point for each 10 cm-$H_2O$ occlusion force above zero, field 152 (FIG. 2A). Further, the type of obstruction is also recordable, field 180, for aid in the diagnostic calculations by the UPP diagnostic program.

f) Subjective Impressions

The UPP diagnostic program also receives data comprising the subjective impressions of the examining clinician to aid in rendering a diagnostic conclusion. Such impressions are mental interpretations of the patterns of abnormalities seen in the patient to reflect the anatomical or functional bias in the study. This bias cannot be accurately recorded by the UPP measurements in all cases. The clinician records answers to simple questions in the UPP diagnostic program that impact the program's interpretation of the data recorded in urethral assessments a-e above. Many of the answers are translated into numeric scores for calculation by the UPP diagnostic program. Other answers do not enter into calculations and are therefore not scored; however, the particular response recorded will impact the diagnosis returned by the UPP diagnostic program.

Figure 2C:
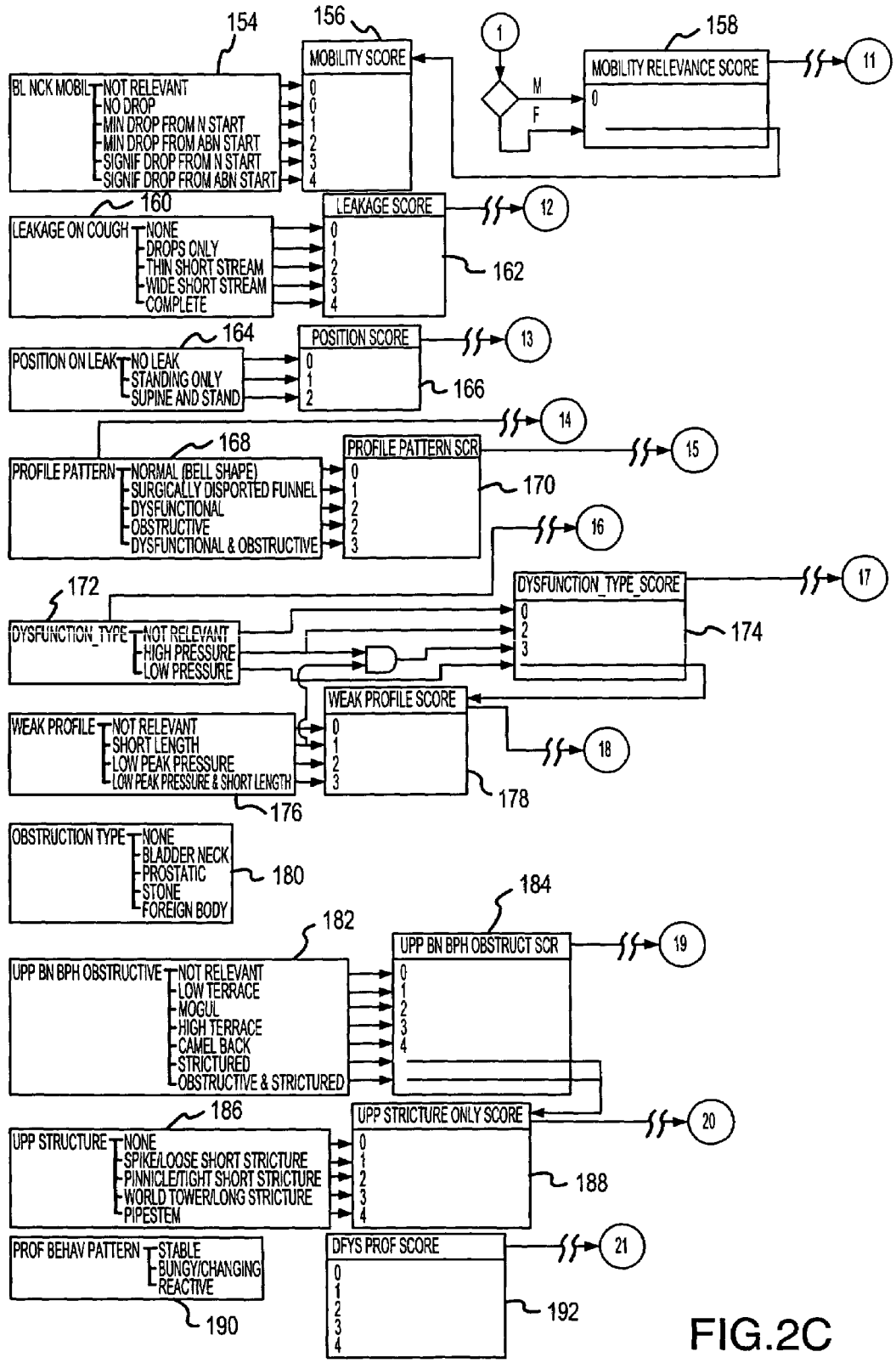

A first area of impression is bladder neck mobility, which is an issue limited to female patients. A list of alternative selections corresponding to clinical observations is provided, field 154 (FIG. 2C). A point score is allocated based upon the clinician's selection, field 156, and is designated as a mobility relevance score, field 158. A male patient is assigned a score of 0 indicating irrelevance, field 158.

A second field of impression is whether the patient exhibits any urethral leakage upon coughing, field 160 (FIG. 2C). This observation is scored between 0 and 4 depending upon the severity of the leakage. Related to this leakage inquiry is the position of the patient when the leakage occurs, i.e., supine or standing, field 164. A positional score is allocated, field 166, with 0 indicating no leakage, 1—leakage when standing, and 2—leakage when laying and standing.

Figure 24:
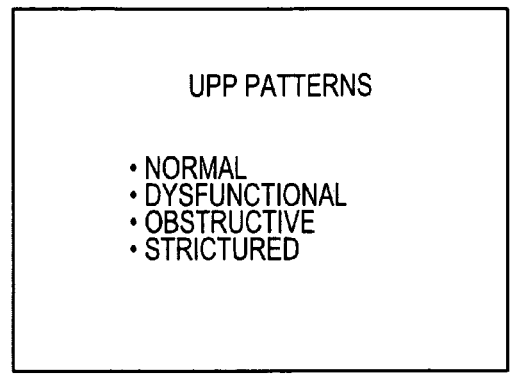
FIG. 24 is a representation of multiple types of urethral pressure profile patterns.
Figure 25:
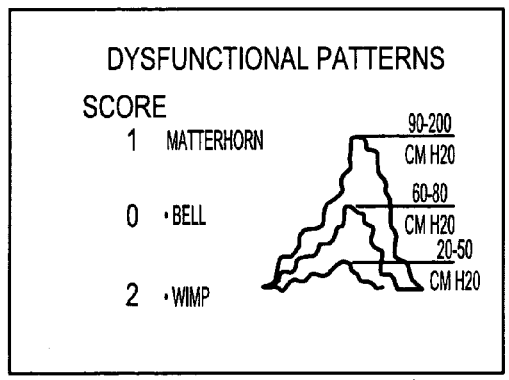
FIG. 25 is a depiction of possible dysfunctional urethral pressure profile patterns.

Another observational inquiry concerns whether the UPP study was normal or abnormal. A UPP is generally analyzed through review of a graph of the pressure profile pattern. See FIGS. 24 & 25. Depending upon the pattern indicated by the pressure graph, a clinician can determine whether there is an abnormality, and if so, whether the abnormality fits with one of obstruction, dysfunction, or both. The UPP diagnostic program accepts entry of the particular indication of the graph, field 168 (FIG. 2C), and provides a corresponding profile pattern score, field 170. Pattern recognition software, for example, Ngram TRANSFORM software by Triada, Ltd. of Ann Arbor, Mich., may be coupled with the UPP diagnostic program to accept direct input of the UPP study to automate the analysis of the pressure profile graphs. In such a case the program may translate the shapes of the profile curves rather than take incremental and discrete pressure measurements obtained during the study.

Observation of dysfunction, either high or low pressure related, is recordable in the UPP diagnostic program, field 172 (FIG. 2C). Translating dysfunction into a score, field 174, also involves combination with weak profile observations, field 176. A UPP pattern is considered weak if it exhibits short length, low peak pressure, or both. A weak field profile pattern is shown labeled as "Wimp" in FIG. 25. Weak profile observations are themselves allocated scores, field 178. High pressure alone receives a dysfunction score of 2; high pressure with a short length is scored as 3; and low pressure is allocated the appropriate weak profile score from field 178. High pressure dysfunction is also observable based upon the profile pattern, field 190 (FIG. 2C), which is further scored, field 192. An example of a high pressure profile is the graph labeled "Matterhorn" in FIG. 25.

Figure 26:
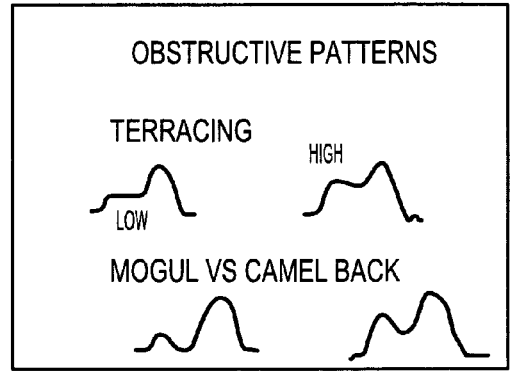
FIG. 26 is a depiction of possible obstructive urethral pressure profile patterns.

If there is obstruction rather than, or in addition to, dysfunction, additional clinical observations may be recorded in the UPP diagnostic program. Obstruction may be classified as bladder neck hypertrophy or enlarged prostate hypertrophy. Either of these conditions, and variations thereof, is reflected in the UPP study and conclusions based upon observations thereof may be entered in field 182 (FIG. 2C). For example, if the prostate is enlarged, the profile may be small (mogul shaped), medium (low terrace), or large (high terrace or camel back shaped), see FIG. 26, each of which is indicative of different diagnostic outcomes. Bladder neck hypertrophy and enlarged prostate hypertrophy observations are scored in field 184.

Figure 27:
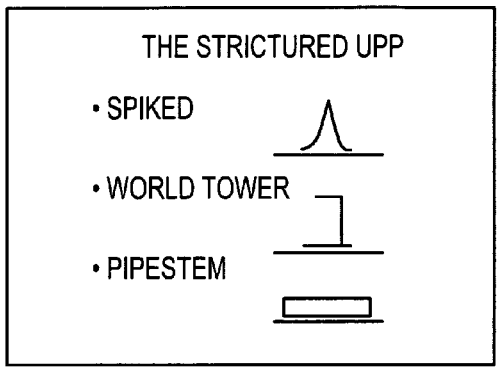
FIG. 27 is a depiction of possible strictured urethral pressure profile patterns.

Stricture profiles from UPP readings in the sphincter are also part of the subjective impression data. See FIG. 27. Typical profiles show patterns that are spiked, towering, or lengthier as a pipe stem. These profiles can be gauged from a UPP graph and recorded, field 186 (FIG. 2C). These stricture observations are further scored by the UPP diagnostic program, field 188. The UPP diagnostic program uses the subjective impression in the diagnosis of urge frequency, functional urinary retention, pain syndromes, stress incontinence, and types of obstruction syndromes (bladder neck hypertrophy, benign prostatic hyperplasia, and stricture).

g) Urethral Assessment Summary

Figure 3:
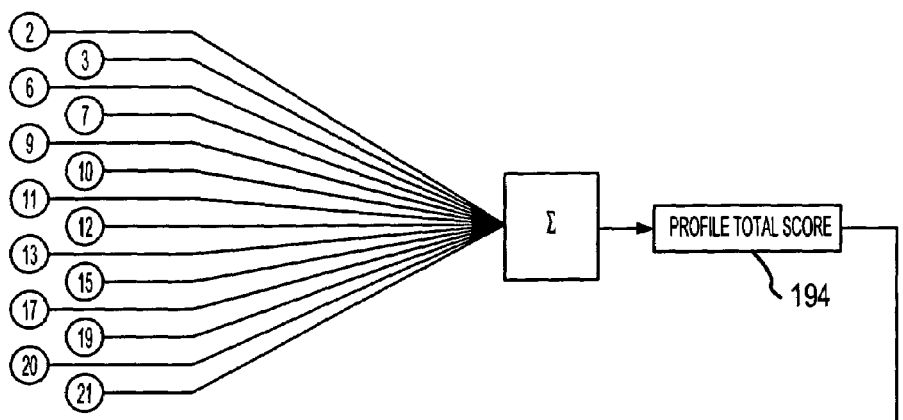
FIG. 3 is a portion of a database field chart depicting fields related to a summary score for a urethral profile.

All scores collected in the urethral assessment phase are summed to give an abnormality score as shown in FIG. 3. These scores include fields 104, 124, 130, 134, 148, 152, 158, 162, 166, 170, 174, 184, 188, and 192. The raw value is presented, field 194, as well as a percentage of the total points available, field 196.

Figure 4:
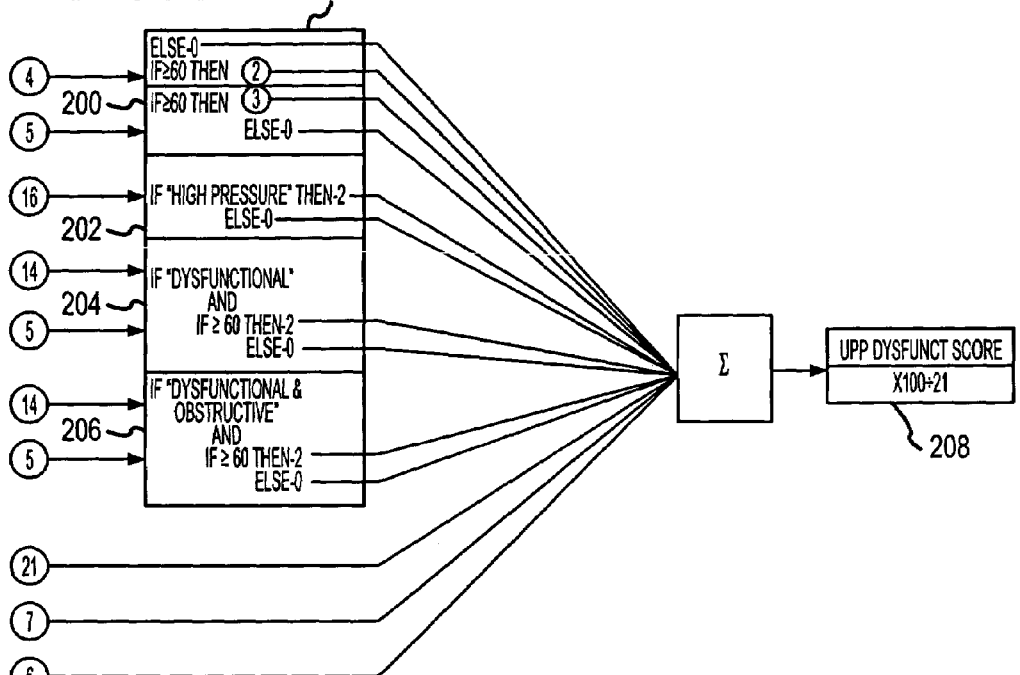
FIG. 4 is a portion of a database field chart depicting fields related to a summary score for urethral dysfunction.

Similarly, scores specific to subgroups of the urethral assessment process are summed and given a percentage of total points score. Both objective and subjective assessment scores are combined for these summations. In the case of spasticity and hypersensitivity, collectively referred to as dysfunction, scores that reflect such upregulation in sphincter activity are summed as shown in FIG. 4. Raw scores summed include fields 130, 134, and 192. Scores from fields 112, 122, 168, and 172, are conditionally summed as part of the total dysfunctional score. Whether the score is chosen for summation is based upon the particular field value, or by comparison of values across multiple fields indicating different patient conditions, as shown in fields 198, 200, 202, 204, and 206 (FIG. 4). If the conditions are not met, a 0 value is used as the score for summation, and the total score is converted to a percentage of total points possible, field 208.

Figure 5:
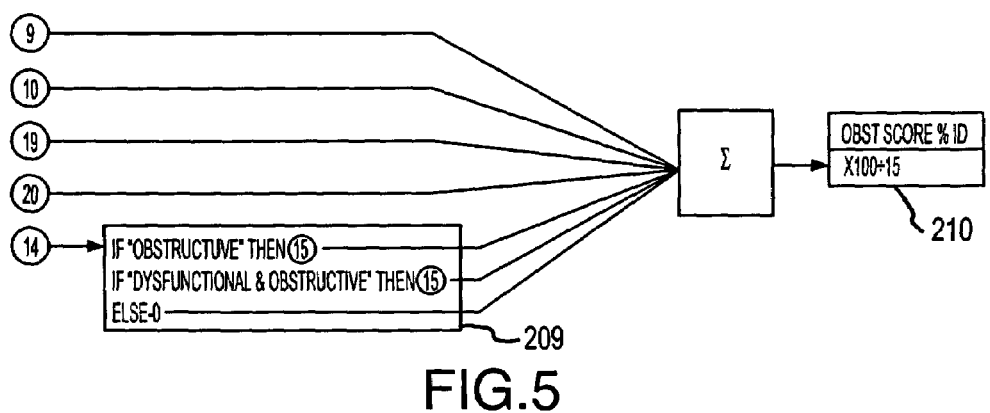
FIG. 5 is a portion of a database field chart depicting fields related to a summary score for urethral obstruction.

Scores that reflect obstruction are summed in field 210 of FIG. 5 as an indication of the severity of obstruction. Fields 148, 152, 184 and 188 representing scores for obstruction length, pressure, bladder neck or benign prostatic hyperplasia profile, and stricture pattern are summed directly. In addition, if the abnormality of the UPP pattern suggests either obstruction or dysfunction and obstruction, the UPP pattern score is included in the sum, field 209 (FIG. 5). If neither of these patterns is present, a score of 0 is attributed for summation. The total score is again converted to a percentage of total points available, field 210.

Figure 6:
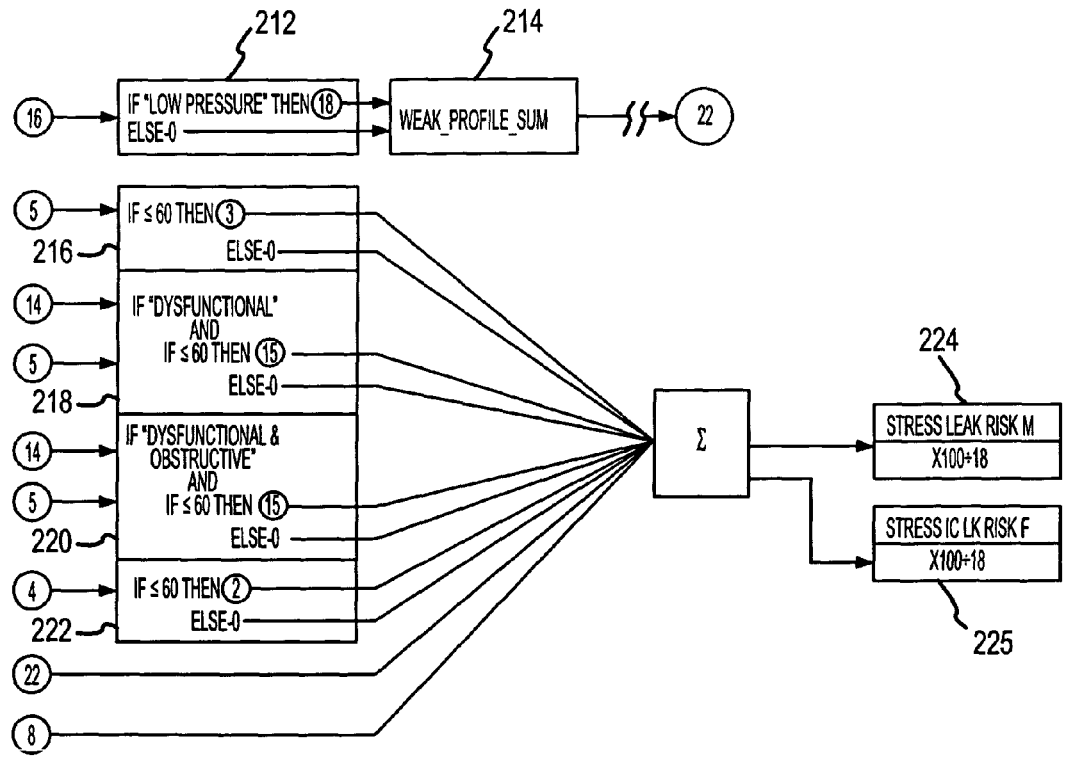
FIG. 6 is a portion of a database field chart depicting fields related to a summary score for urethral stress leak risk.

Scores that reflect sphincter weakness are summed as a risk for incontinence as seen in FIG. 6. This incontinence sum is converted into a percentage number to indicate a degree of risk for leakage for males and females, fields 224 and 225. Factors contributing to the sum include an antecedent determination of whether the dysfunction exhibits low pressure characteristics. If so, the weak profile score of field 178 (FIG. 2C) is added to the summation figure of field 224 FIG. 6) via an intermediary field 214; if not, a 0 value is placed in field 214. Similar to the obstruction summation, if the abnormality of the UPP pattern suggests either obstruction or dysfunction and obstruction, the UPP pattern score is included in the sum, fields 218 and 220. If neither of these patterns is present, a score of 0 is attributed for summation. Further, if the average peak pressures either full or empty are less than or equal to 60 cm-$H_2O$, the average peak scores stored in fields 114 and 124 are included in the summation, fields 216 and 222. If they are greater than 60 cm-$H_2O$, 0 is attributed to the sum. The norm value of 60 cm-$H_2O$ used in this embodiment may be adjusted to reflect differences in norms between different population groups.

Each of these various summation values is used in the computer analysis performed by the UPP diagnostic program to render an automated diagnosis. They are also figures that may be presented in a summary report, for example, to the referring physician, as foundation for the diagnosis. The scores may be adjusted for specific biases in a particular patient study, but generally weightings should change no more than 5-10 percent. Diagnoses related to spasticity problems include void dysfunction, urge incontinence, and pain syndromes such as interstitial cystitis, prostatodynia, and prostatitis. Obstruction diagnoses include benign prostatic hyperplasia, bladder neck hypertrophy, and strictures, incontinence/weakness diagnoses may reflect stress incontinence or post prostatectomy incontinence.

Bladder

Figure 28:
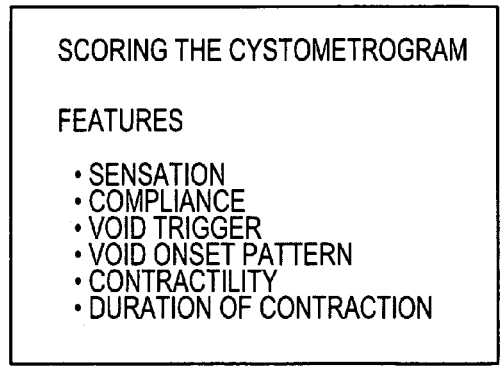
FIG. 28 is a representation of elements to be measured, observed, and scored in a cystometrogram.

In the bladder assessment phase, three variables are assessed by a cystometrogram: reflex excitability, sensation, and tone (compliance). Features represented in the cystometrographic data are listed in FIG. 28. Assumptions of normalcy for the bladder, variance from which indicates a pathology, are as follows: normal capacity without excitability is 350-500 cc; sensations associated with filling the bladder are never painful; and compliance should be less than 5 cm-$H_2O$ at all times until the stretch limit of the bladder is reached.

a) Reflex Excitability

Indications of reflex excitability are measured through bladder capacity, which is assessed three ways: spontaneous activity, volitional void effort, and subjective assessment.

1) Spontaneous Activity

Figure 7:
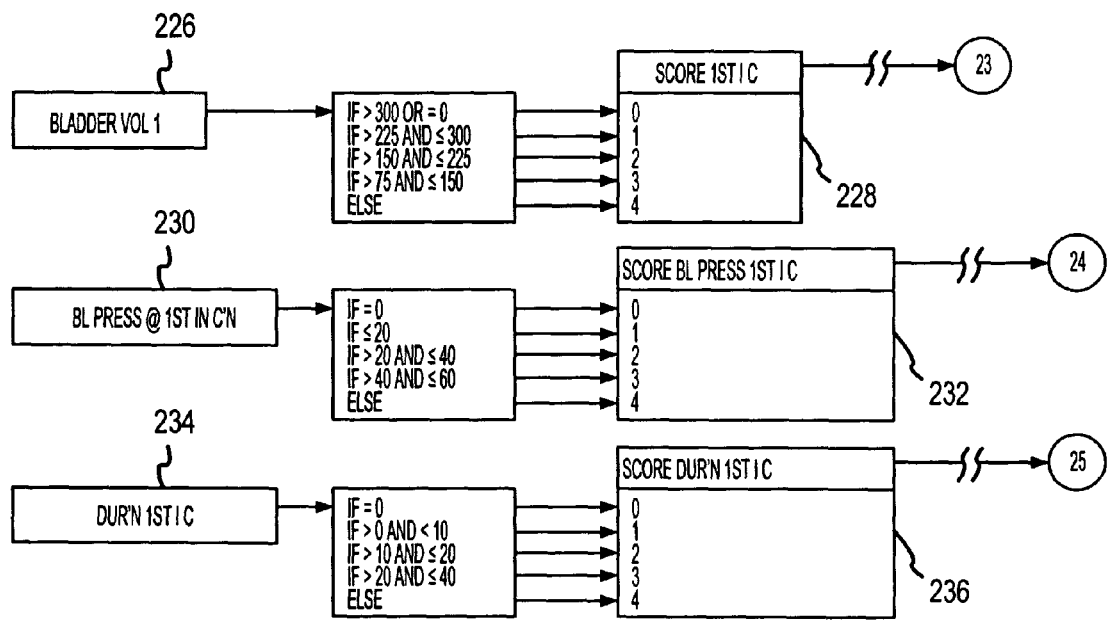
FIG. 7 is a portion of a database field chart depicting fields related to bladder capacity measurements, specifically spontaneous reflex excitability.
Figure 20:
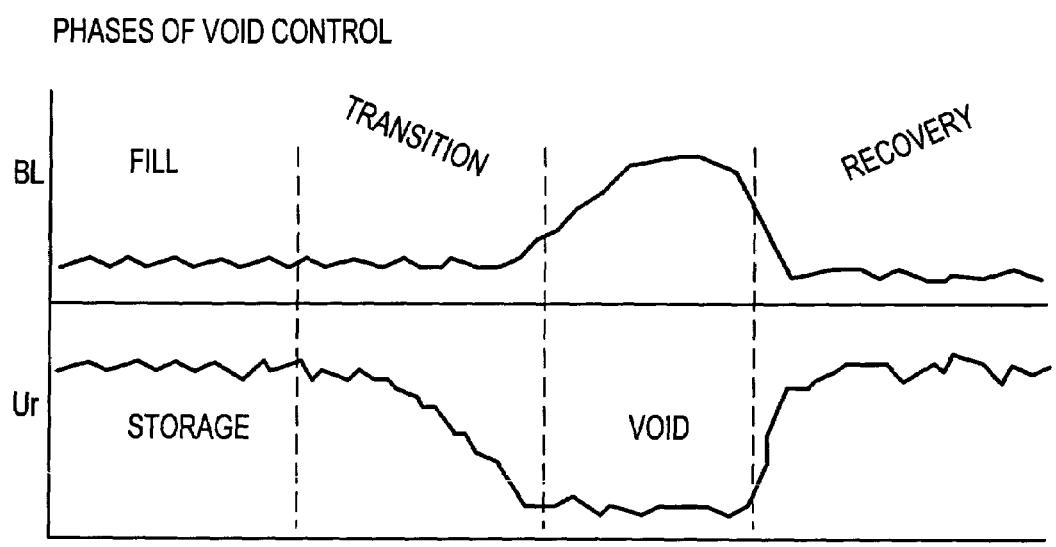
FIG. 20 is a urethral pressure profile graph depicting the phases of void control.
Figure 29:
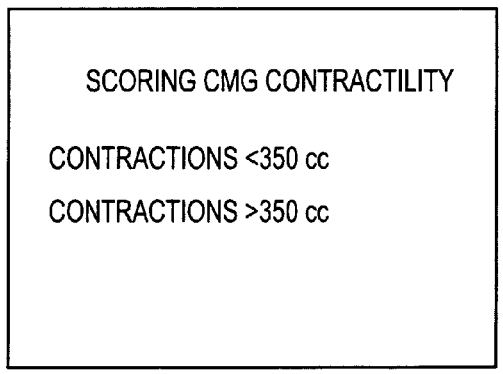
FIG. 29 is a representation of elements considered in scoring cystometrogram characteristics of contractility.

Spontaneous activity refers to a non-volitional contraction in an attempt to void the bladder as it is filled. A general representation of a UPP graph of void control phases is shown in FIG. 20. The top half of the graph represents the phases of detrusor contraction in the bladder, while the bottom half represents the phases of sphincter contraction in the urethra. The UPP diagnostic provides for entry of several measurable components of such spontaneous activity that is triggered by a fill rate of 50 cc/min. In FIG. 7 the bladder volume at the point of contraction is recorded in field 226 and scored between 0 and 4 points at decrements of 75 cc below 300 cc, field 228. This threshold point is also represented in FIG. 29. The peak pressure in the bladder at the time of contraction is similarly recorded, field 230 (FIG. 7), and scored between 0 and 4 corresponding to increments of 20 cm-$H_2O$ from a baseline pressure of 0 cm-$H_2O$, field 232. Finally, the duration of the contraction is recorded, field 234, and scored between 0 and 4 reflecting 10-second increments of continued contraction, field 236. The UPP diagnostic program will later sum these point scores to quantify the degree of neural over-facilitation as well as the muscular integrity of the detrusor.

2) Volitional Void Effort

Figure 8:
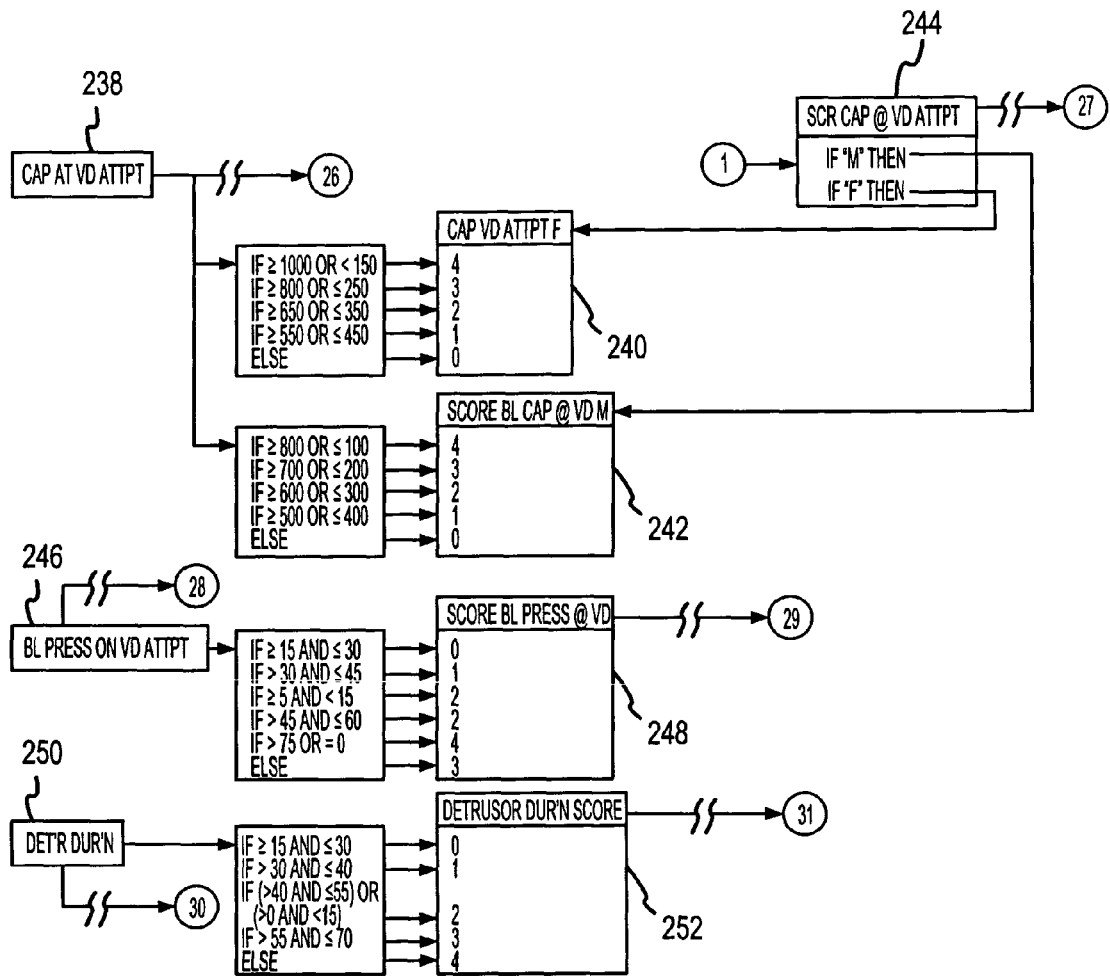
FIG. 8 is a portion of a database field chart depicting fields related to bladder capacity measurements, specifically volitional reflex excitability.

To measure volitional void effort, the patient is instructed to initiate the void of the bladder when a strong sense of fullness is reached. As above with the non-volitional void, bladder volume, peak pressure, and duration measurements are each recorded and stored. In FIG. 8, bladder capacity at the initiation of void is recorded, field 238, and scored between 0-4 points at increments or decrements of 100 cc above or below 400-500 cc for males, field 242 (e.g., $\geq 800$ or $\leq 100=4$; $\geq 700$ or $\leq 200=3$; $\geq 600$ or $\leq 300=2$; $\geq 500$ or $\leq 400=1$; and $\geq 400$ and $\leq 500=0$). A slight bias is allowed for the female patient, field 240, wherein the normal bladder capacity value is increased by 50 cc. Abnormal ranges are broadened to some extent as well. The scored value is recorded in field 244.

In addition to capacity, bladder pressure is measured both when the bladder is in an empty state, field 239a, and when the bladder is full, field 239b (see FIG. 2A). A calculation can be made to relate these bladder pressures to the bladder capacity at the void attempt of field 238. The ratios of pressures to capacity are transformed into percentage figures in fields 241a and 241b, for pressures of empty and full bladders, respectively.

The peak bladder pressure at the contraction is stored in field 246. Normal is defined as 15-30 cm-$H_2O$. Scoring is translated as follows: $\geq 15$ and $\leq 30=0$; $\geq 30$ and $\leq 45=1$; $>45$ and $\leq 60$ or $\geq 5$ and $<15=2$; $>60$ and $\leq 75$ or $<5=3$; and $>75$ or $0=4$; all in cm-$H_2O$. The measured duration of contraction is stored in field 250, and the score is stored in field 252 as follows: 15-30 sec (normal)=0; 0-14 sec or 31-45 sec=1; 46-60 sec=2; 61-75 sec=3; and >75 sec=4.

3) Subjective Assessment

Figure 9:
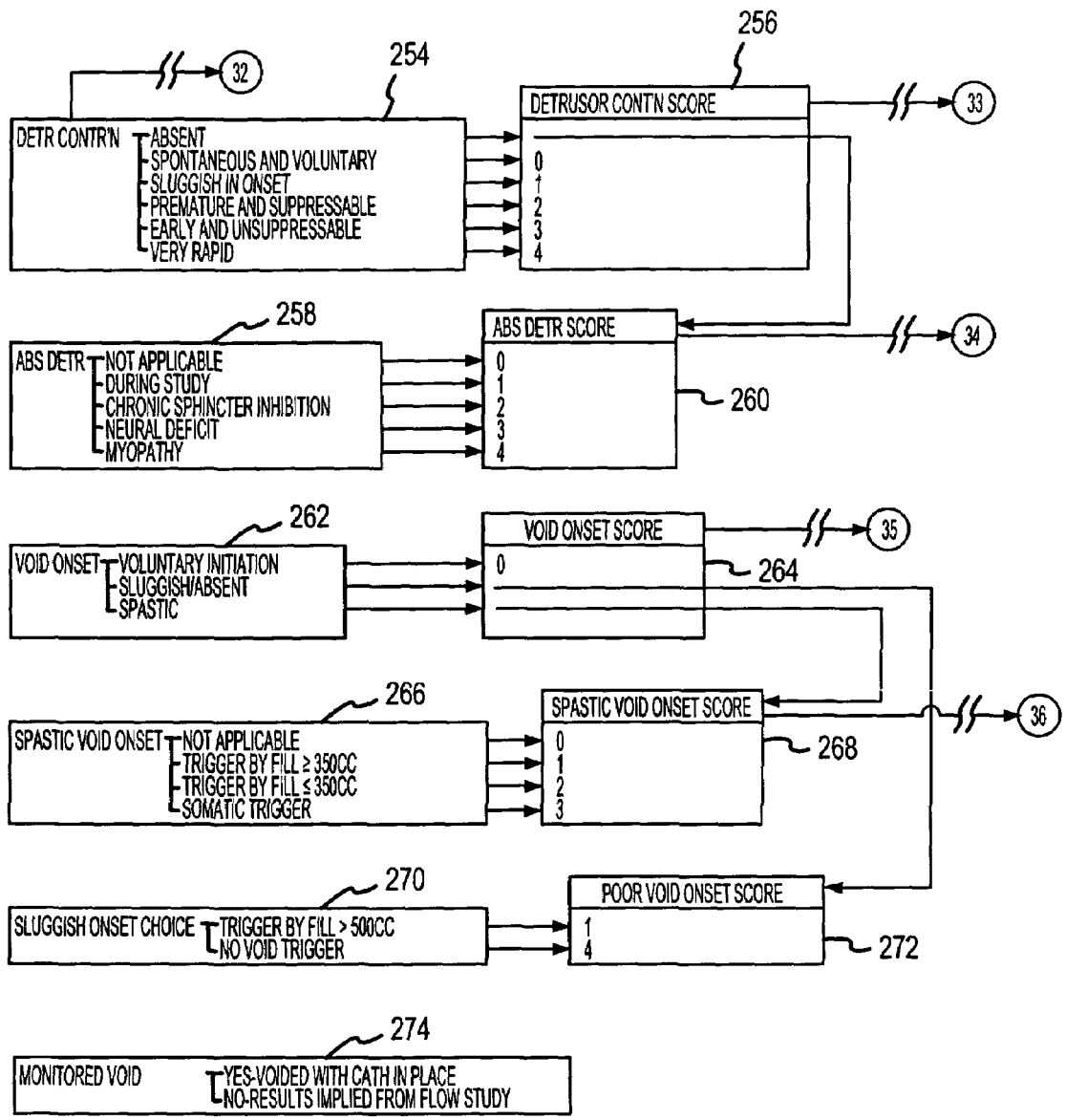
FIG. 9 is a portion of a database field chart depicting fields related to bladder capacity measurements, specifically subjective assessments of reflex excitability.
Figure 30:
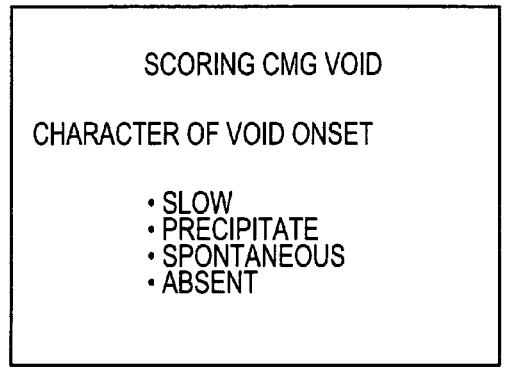
FIG. 30 is a representation of elements considered in scoring the cystometrogram characteristics of void onset.

In addition to the objective UPP measurements performed, subjective considerations are input into the UPP diagnostic program and attributed point scores as shown in FIG. 9. A spontaneous detrusor contraction event is observed and matched to the appropriate description in field 254. If the contraction was voluntary, a score of 0 is assigned in field 256. The character of other detrusor contraction states, as represented generally in FIG. 30, are scored between 1 and 4, field 256. If there is no involuntary contraction, additional inquiries are available for input in field 258. For example, if it is known that the patient's detrusor will contract, but it did not during the study, a score of 1 is assigned in field 260. Other rationales for the absence of detrusor contraction are similarly scored between 0 and 4 in field 260.

Next, subjective considerations surrounding the patient's volitional void effort, see FIG. 31, are recorded in field 262 and scored in field 264. A score of 0 is allocated to a purely voluntary void. If the void is spastic, additional criteria are considered in field 266 such as the fill volume that triggered the void, or whether the trigger was somatic. Scores are attributed and stored in field 268 (FIG. 9). If the attempted voluntary void is sluggish or absent, field 270 queries whether the void occurred at a high fill volume or merely not at all, and the entry is scored as either 1 or 4 respectively in field 272.

The final subjective inquiry related to reflex excitability concerns whether the void recorded occurred while the UPP catheterization monitor was in place or whether the results were implied from the flow study discussed later. The clinician's entry is stored in field 274 (FIG. 9).

b) Sensation

Figure 10A:
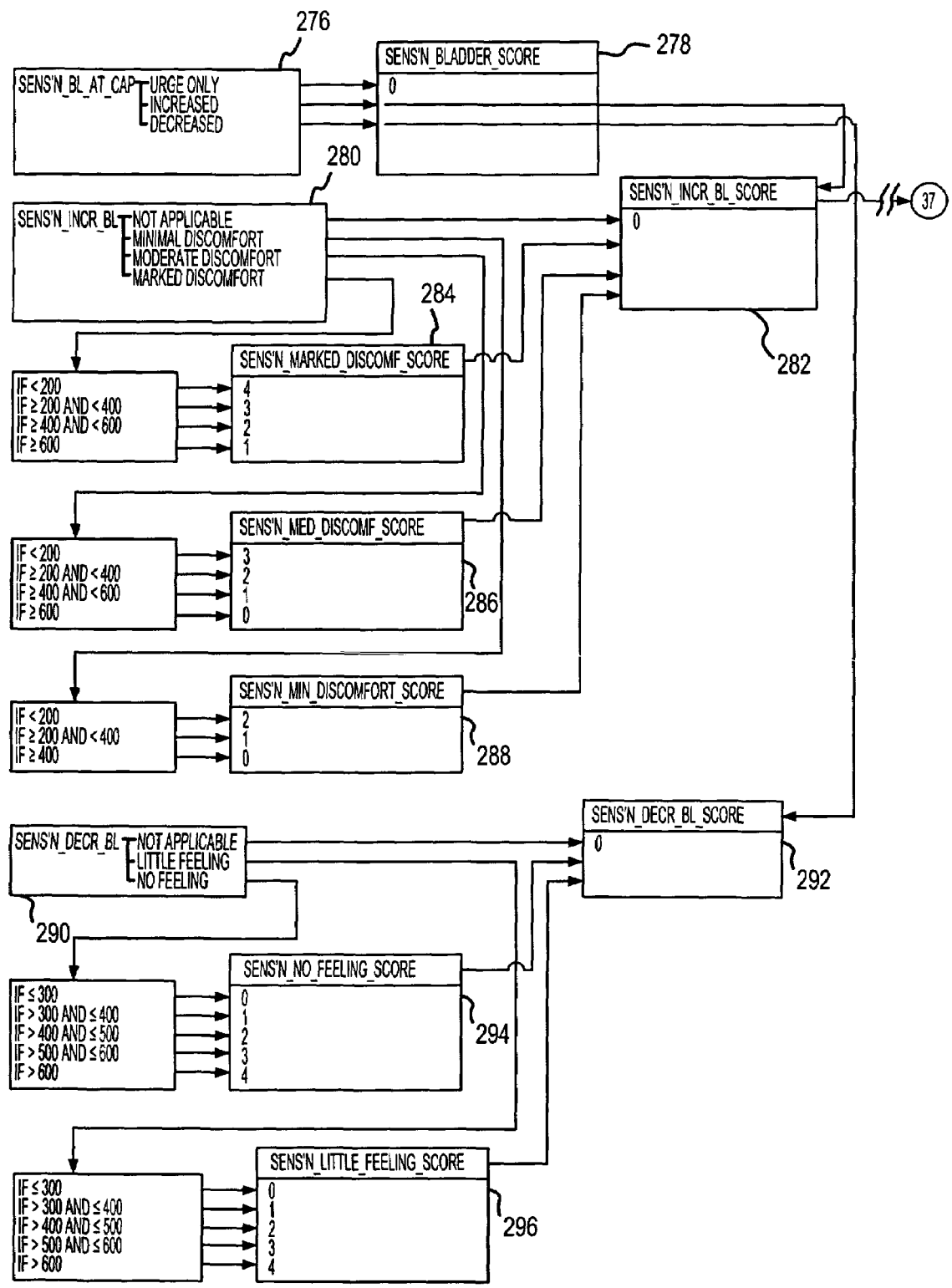
FIGS. 10A and 10B comprise a portion of a database field chart depicting fields related to bladder sensation measurements and dynamics.
Figure 10B:
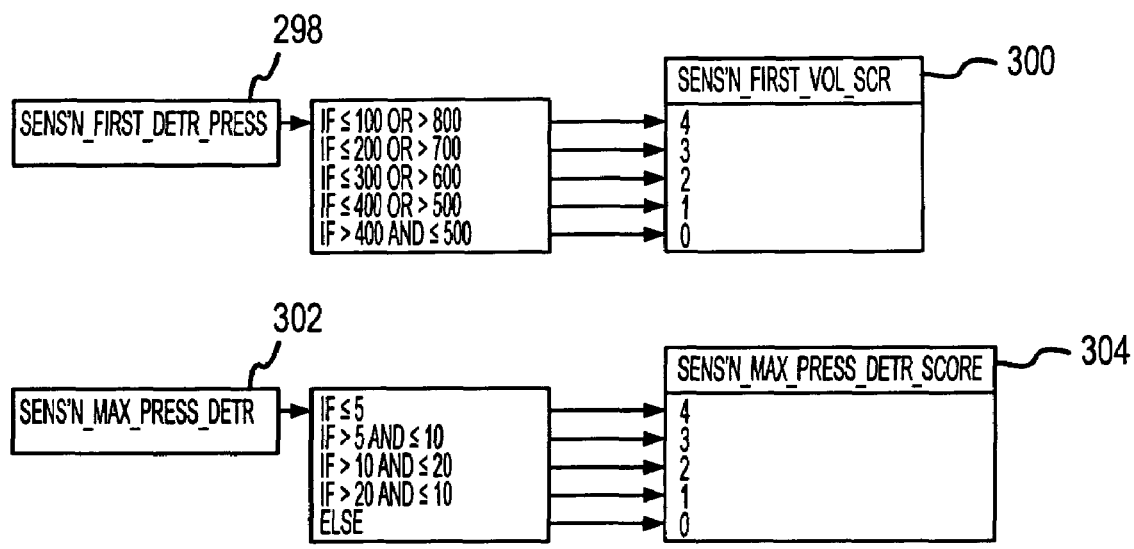

Sensation is scored in FIGS. 10A and 10B according to severity of urge, volume of fill, and pressure in the bladder. There is a skew to the severity score based on volume of fill tolerated.

1) Severity

Normal urge to void occurs when the bladder reaches capacity. Beyond this state, abnormal urge can be viewed as either increased urge to void or decreased awareness of the need to void. See FIG. 32. A choice between these states is provided in field 276 (FIG. 10A). Translating these states into scores for field 278, other than 0 points for normal urge, requires a much more detailed inquiry.

Increased awareness of filling is divided into three tiers as seen in field 280 (FIG. 10A): minimal discomfort, moderate discomfort, and marked discomfort. Each of these levels of discomfort is scored separately based upon the associated fill volume at the point such discomfort is registered. Minimal discomfort is scored and recorded in field 288 as follows: <200 cc=2; ≧200 cc and <400 cc=1; and ≧400 cc=0. Moderate discomfort is scored and recorded in field 286 (FIG. 10A) as follows: <200 cc=3; ≧200 cc and <400 cc=2; ≧400 cc and <600 cc=1; and ≦600 cc=0. Finally, for increased awareness scoring, marked discomfort is awarded points and recorded in field 284 as follows: <200 cc=4; ≧200 and <400 cc=3; ≧400 cc and <600 cc=2; and ≧600 cc=1. Dependent upon the particular discomfort level of the patient and corresponding fill volume, the appropriate score for increased bladder sensation is recorded in field 282, which is further recorded in field 278 for the overall filling awareness score.

Decreased awareness of filling is divided into two tiers that can be described as little feeling and no feeling as seen in field 290 (FIG. 10A). In the case of the patient feeling little sensation on filling, the score is allocated in field 296 based upon bladder volume at the time of sensation as follows: ≦300 cc=0; >300 cc and <400 cc=1; ≧400 cc and ≦500 cc=2; and >500 cc and <600 cc=3. For a patient with no feeling during fill, field 294 holds scores as follows: ≦300 cc=0; >300 cc and ≦400 cc=2; >400 cc and ≦500 cc=3; and >500 cc=4. Dependent upon whether the patient had no feeling or merely little, and the corresponding fill volume, the appropriate score for decreased bladder sensation is recorded in field 292, which is further recorded in field 278 for the overall filling awareness score.

2) Sensation of Volume in Bladder

In addition to being aware of the sensation of filling, the patient should similarly be able to indicate the point at which a volume in the bladder is actually felt. This may be at the same point or different from first sensation of filling. This volume sensation is recorded in field 298 (FIG. 10B) and the related point score is stored in field 300. The volume feeling is scored as follows: ≦100 cc or >800 cc=4; ≦200 cc or >700 cc=3; ≦300 cc or >600 cc=2; ≦400 cc or >500 cc=1; and >400 cc and ≦500 cc=0.

3) Bladder Pressure at Maximum Unpleasantness

The final sensation criterion reflects the detrusor pressure when the bladder is filled to a capacity of maximum unpleasantness to the patient. The detrusor pressure is recorded in field 302 (FIG. 10B) and the score in field 304. Scores are allocated based upon detrusor pressure as follows: <5 cm-$H_2O$=4; 5-10 cm-$H_2O$=3; 11-20 cm-$H_2O$=2; >20 cm-$H_2O$=1; and No Discomfort=0. One may note that these maximum unpleasantness scores are the inverse of the penalty values applied for compliance below.

c) Compliance (Tone)

Figure 11:
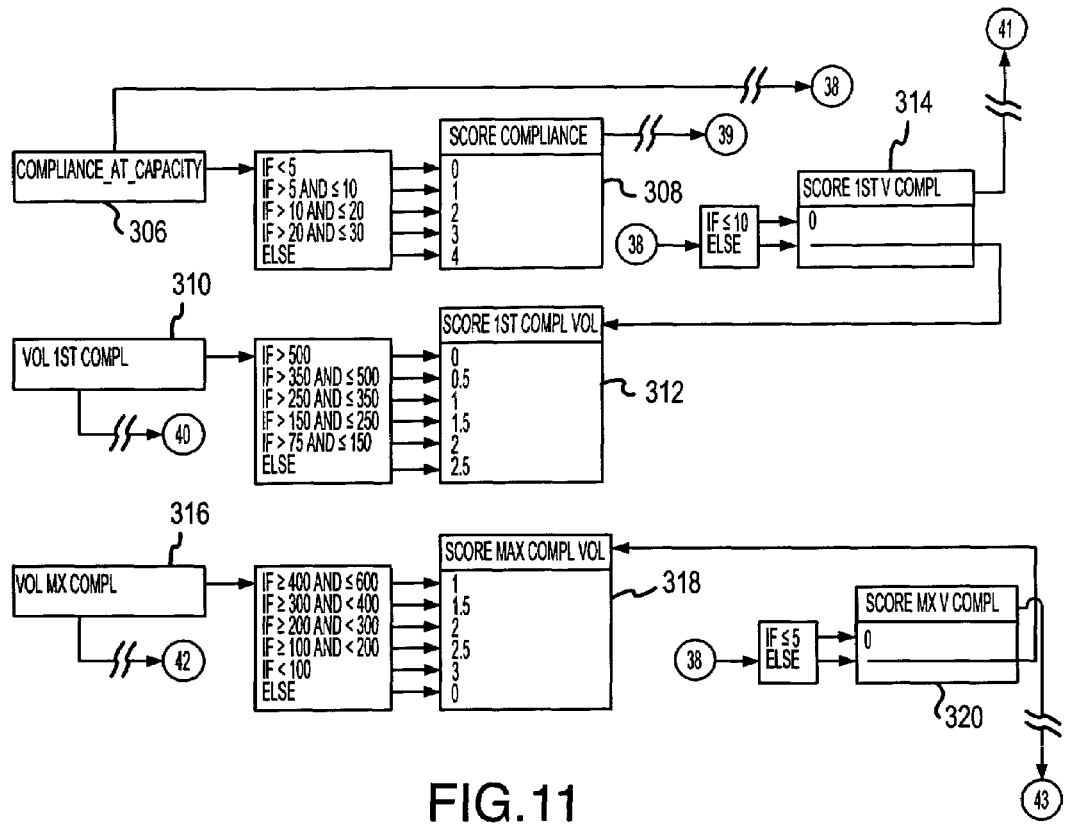
FIG. 11 is a portion of a database field chart depicting fields related to bladder compliance measurements and dynamics.

Compliance or tone analysis of the detrusor considers the pressure exerted on the detrusor at capacity fill volume in the bladder as opposed to merely the sensory point of maximum unpleasantness as above. Compliance refers to the ability of the bladder to expand and thereby moderate its internal pressure as resulting from the fill of fluid. The three different datum collected corresponding to compliance, as seen in FIG. 11, are maximum bladder pressure at capacity, fill volume at the first noted pressure rise, and volume at maximum bladder pressure.

1) Maximum Bladder Pressure at Capacity

For the first measurement of compliance, the maximum bladder pressure is recorded at capacity. The maximum pressure reading is held in field 306 (FIG. 11) and the related score is calculated and stored in field 308. Scoring for the maximum pressure is as follows: <5 cm-$H_2O$=0; 5-10 cm-$H_2O$=1; 11-20 cm-$H_2O$=2; 21-30 cm-$H_2O$=3; and >30 cm-$H_2O$=4.

2) Fill Volume at Pressure Rise

Another measure of compliance, represented in FIG. 33, looks at the volume of the bladder at first noticeable pressure rise. The raw measurement is recorded in field 310 (FIG. 11) while the score is allocated in field 312 as follows: >500 cc=0; >350 cc and ≦500 cc=0.5;>250 cc and ≦350 cc=1; >150 cc and ≦250 cc=1.5; >75 cc and ≦150 cc=2; and <75 cc=2.5. This second compliance measurement is only significant if the pressure rise is above 5 cm-$H_2O$, which is checked in field 314 (FIG. 11). An adjustment of any score allocated in field 312 is made in the event that the pressure rise is not above 5 cm-$H_2O$, and a score of 0 is substituted.

3) Volume at Maximum Bladder Pressure

The final compliance measurement, also represented in FIG. 33, records the volume of the bladder fill capacity when maximum pressure is reached, field 316. Scoring in field 318 for various volumes is as follows: >600 cc=0; ≧400 cc and ≦600 cc=1; ≧300 cc and <400 cc=1.5; ≧200 cc and <300 cc=2; ≧100 cc and <200 cc=2.5; and <100 cc3. Similar to the volume measurement at pressure rise above, this compliance measurement is only significant if the pressure rise is above 10 cm-$H_2O$, which is checked in field 320 (FIG. 11). An adjustment of any score allocated in field 318 is made in the event that the pressure rise is not above 10 cm-$H_2O$, and a score of 0 is substituted.

d) Bladder Assessment Summary

Figure 12:
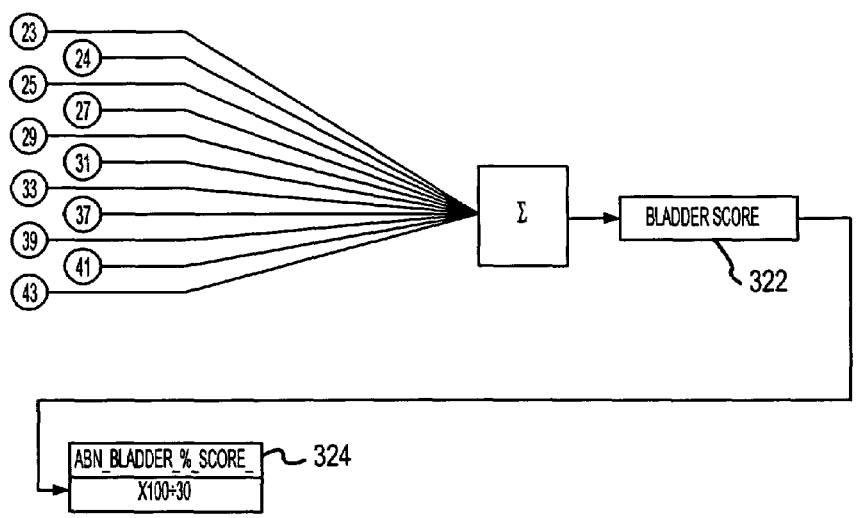
FIG. 12 is a portion of a database field chart depicting fields related to a summary score for bladder abnormality.

As shown in FIG. 12, all bladder-related scores are summed to give a total abnormality score and a percentage abnormality score, field 322. Included in the bladder abnormality score are fields 228, 232, 236, 244, 248, 252, 256, 308, 314, and 320. As with earlier summary figures, this total score is transformed into a percentage of the possible total in field 324 (FIG. 12) to indicate a degree of abnormality. Additional score subtotals are tallied with respect to reflex excitability and compliance assessments.

Figure 13:
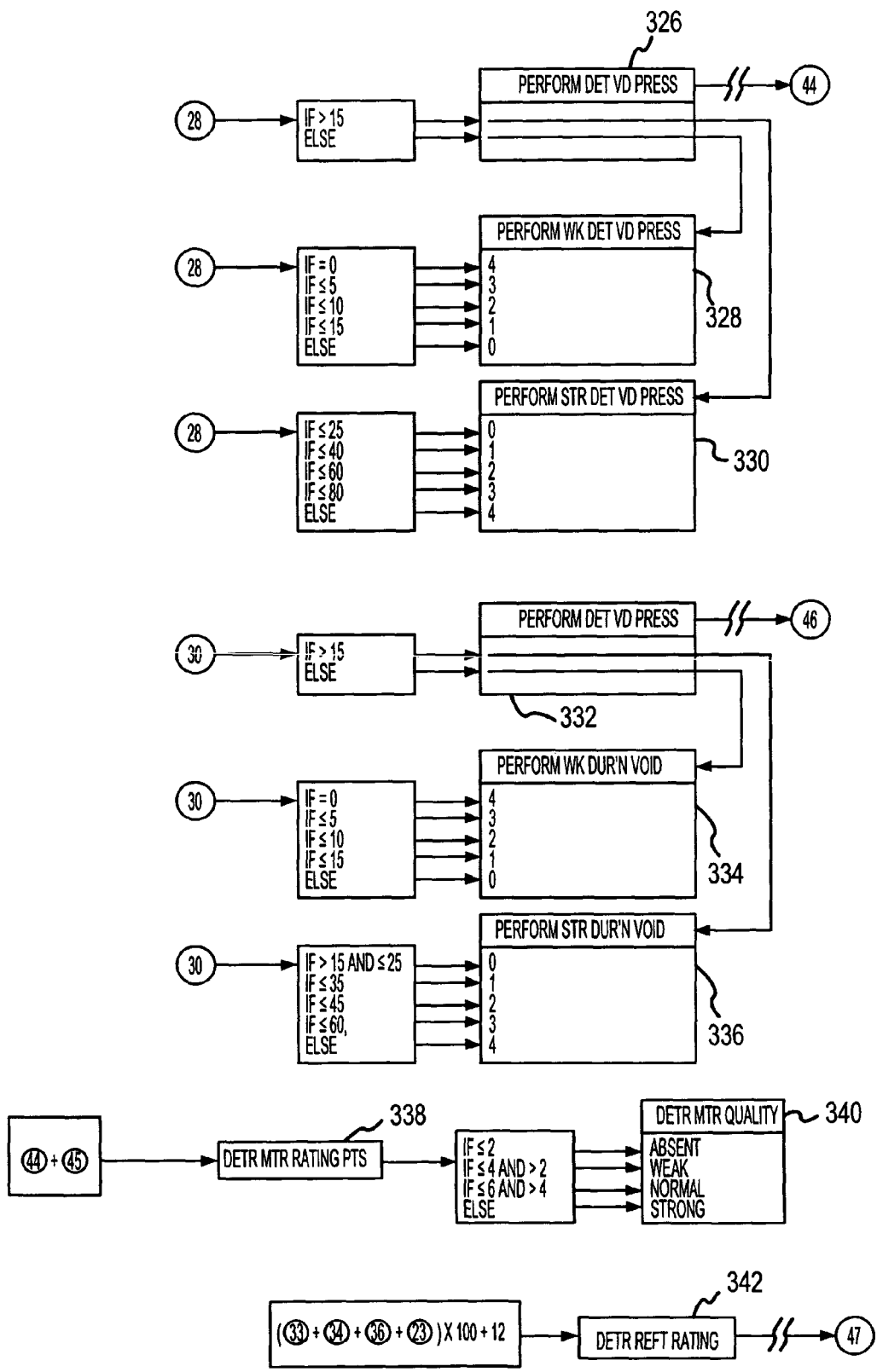
FIG. 13 is a portion of a database field chart depicting fields related to summary scoring for bladder reflex excitability.

Reflex excitability totals are shown computed in FIG. 13. These calculations center on the detrusor reflex rating and whether it is of significant spasticity. Fields 328 and 330 provide more discrete breakdown scores for the peak bladder pressure at detrusor contraction. Pressures between 0 cm-$H_2O$ and 15 cm-$H_2O$ are scored in field 328 as follows: 0=4; ≦5 cm-$H_2O$=3; ≦10 cm-$H_2O$=2; and ≦15 cm-$H_2O$=1. Likewise, pressures above 15 cm-$H_2O$ are scored in field 330 as follows: ≦25 cm-$H_2O$=0; ≦40 cm-$H_2O$=1; ≦60 cm-$H_2O$=2; ≦80 cm-$H_2O$=3; and >80=4. The appropriate score from either field 328 or 330, depending on the patient's pressure reading, is then recorded in field 326 (FIG. 13).

Similarly, fields 334 and 336 (FIG. 13) are employed to provide more discrete breakdown scores for the duration of detrusor contraction. Time between 0 and 15 seconds, indicative of a weak performance, is scored in field 334 as follows: 0 sec=4; ≦5 sec=3; ≦10 sec=2; and ≦15 sec=1. Contraction time greater than 15 seconds, indicative of a strong detrusor performance, is scored in field 336 as follows: >15 sec and ≦25 sec=0; >25 sec and ≦35 sec=1; >35 sec and ≦45 sec=2; >45 sec and ≦60 sec=3; and >60 sec=4. The appropriate score from either field 334 or 336, depending on the patient's contraction time, is then recorded in field 332 (FIG. 13).

These new, more discrete scores rating the detrusor performance are added together in field 338. A further analysis is performed based upon this total to provide and indication of the functional quality of detrusor performance. Field 340 (FIG. 13) rates a total score of less than or equal to 2 as Absent of function; over 2 up to and including 4 as Weak in function; over 4 up to and including 6 as Normal; and over 6 as Strong.

Figure 14:
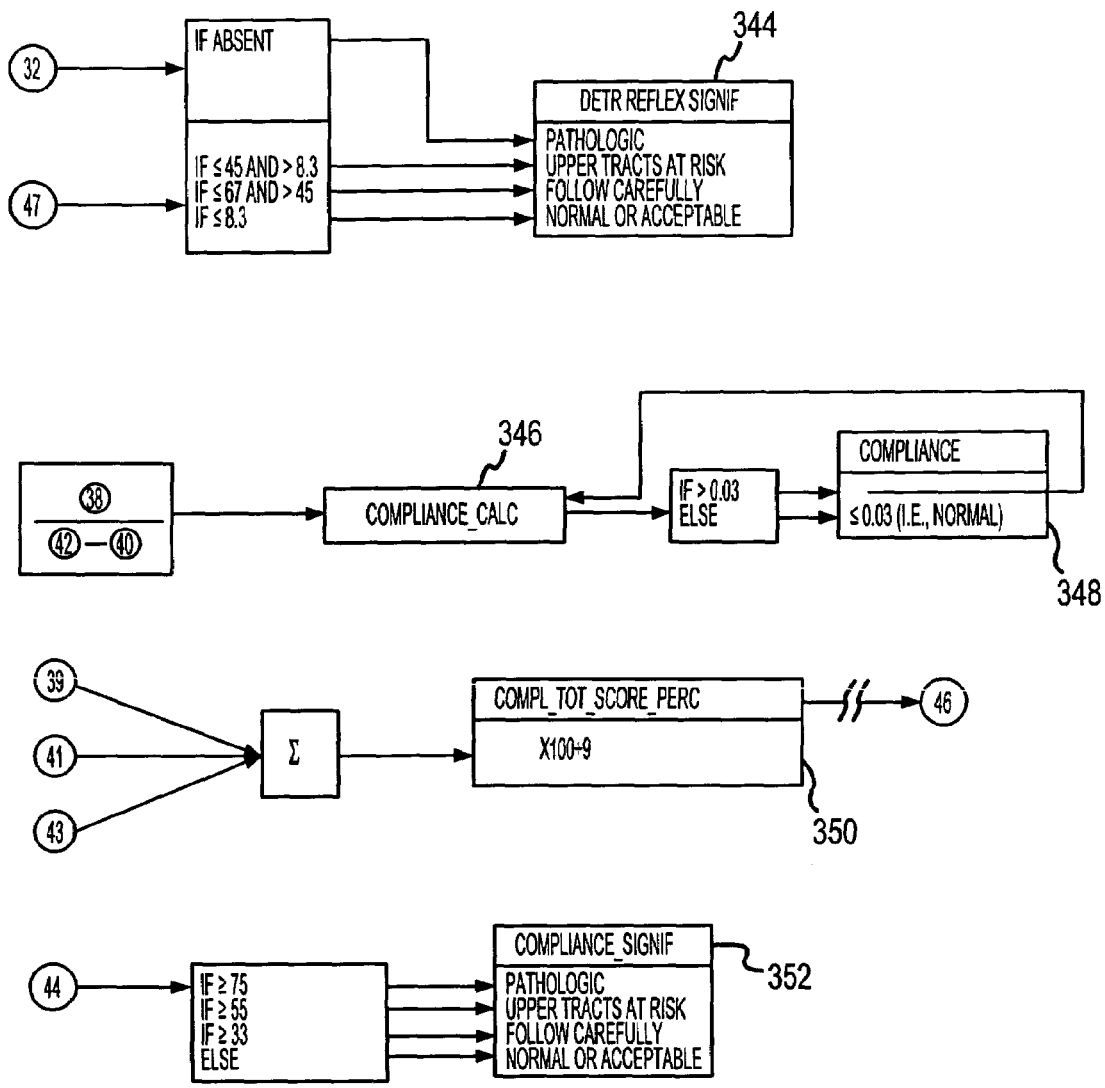
FIG. 14 is a portion of a database field chart depicting fields related to summary scoring for bladder compliance.

A second summary rating describes the significance of the reflex excitability of the detrusor. A preliminary calculation to this rating sums the detrusor contraction score of field 256 (FIG. 9), the volitional void effort score of field 264 (FIG. 9), and the bladder volume at contraction score of field 228 (FIG. 7); subtracts the absent contraction score of field 260 (FIG. 9); and converts the result into a percentage of the total possible points recorded in field 342 (FIG. 13). The significance of any reflex excitability is then described in field 344 (FIG. 14). First, if it was noted in field 254 that detrusor contraction was absent, reflex excitability is described as areflexic. Then drawing on the percentage recorded in field 342 (FIG. 13), descriptions are returned as follows: ≦8.3=normoreflexic; >8.3 and ≦45=hypertonic; >45 and ≦67=spastic; and >67=very spastic.

The UPP diagnostic program also performs summary calculations related to compliance characteristics which are shown in FIG. 14. These calculations indicate the degree of deviation from normal compliance and whether this is of significance or not. In field 346, an indication of the relative normalcy of compliance is generated by dividing the maximum pressure reading at bladder capacity, field 306 (FIG. 11), by the difference between the volume at maximum pressure, field 316, and the volume at first significant pressure rise, field 310. If the compliance figure, when rounded to two digits is ≦0.03, the program stores a "normal" notation in field 348. If the compliance figure is >0.03, the actual figure is stored in field 348 (FIG. 14).

The second summary compliance measurement sums the maximum pressure score, field 308 (FIG. 11), the first noticeable pressure rise score, field 314, and the volume at maximum bladder pressure score, field 320, and converts this sum into a percentage figure of the total possible points which is stored in field 350 (FIG. 14). The program then allocates significance ratings based upon the percentage score in field 352. A percent number of <33 is considered normal or acceptable; ≧33 and <55 indicates the patient's condition should be followed carefully; ≧55 and <75 indicates that upper tracts are at risk; and ≧75 suggests a pathologic condition.

Flow Rate

The third assessment phase performed by the UPP diagnostic program involves the measurements and observation records of patient flow rate data. The program allocates scores to traditional parameters such as average and peak flow rates, as wells as to patterns of flow recorded over the void period. See FIG. 34. This combination better separates the neurological from the anatomical components of the patient's pathology. Both objective and subjective criteria are therefore considered and scored to aid in the final diagnosis and treatment recommendation calculations.

a) Objective Scoring

Figure 15A:
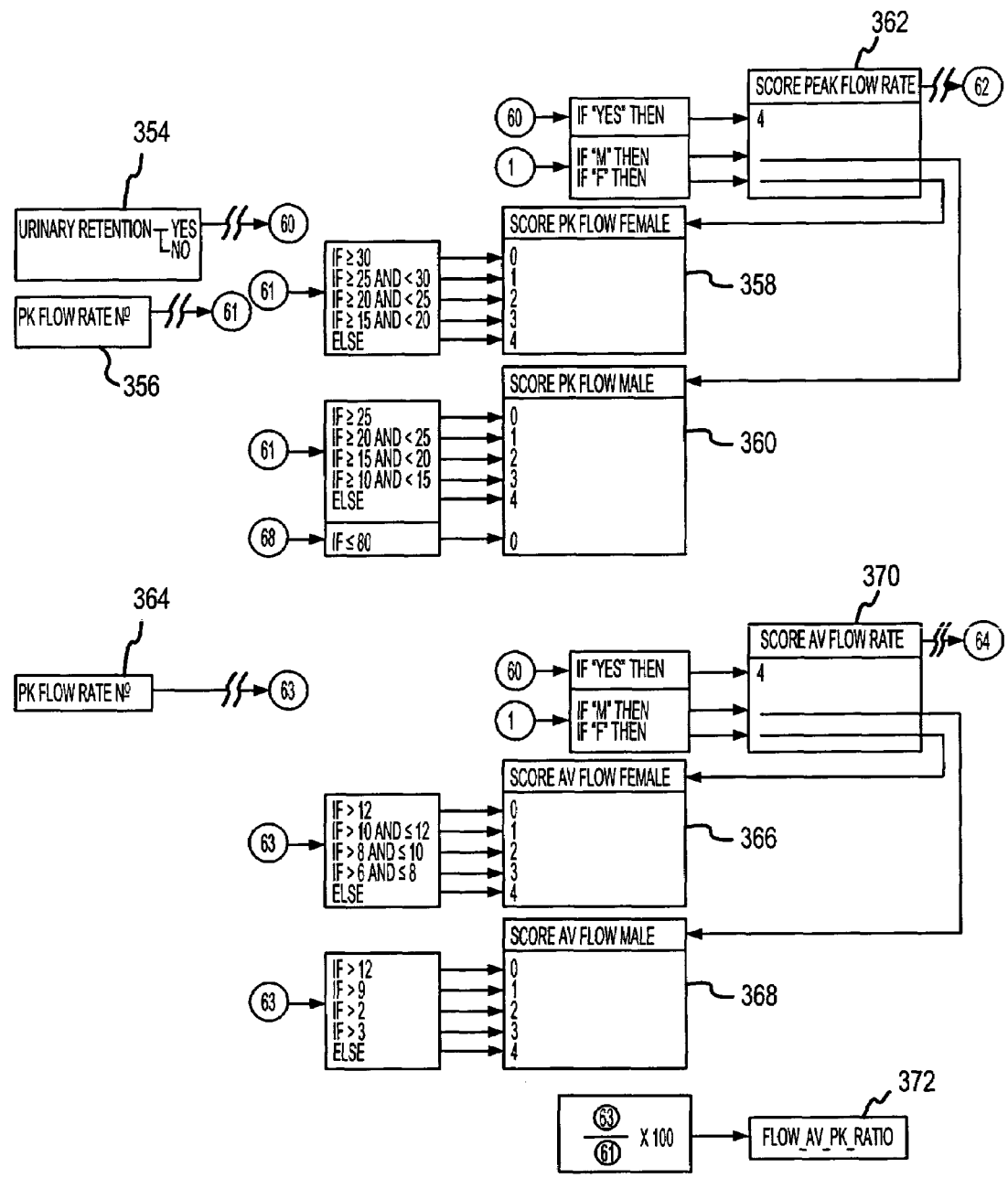
FIGS. 15A and 15B comprise a portion of a database field chart depicting fields related to objective flow rate measurements and scores.
Figure 15B:
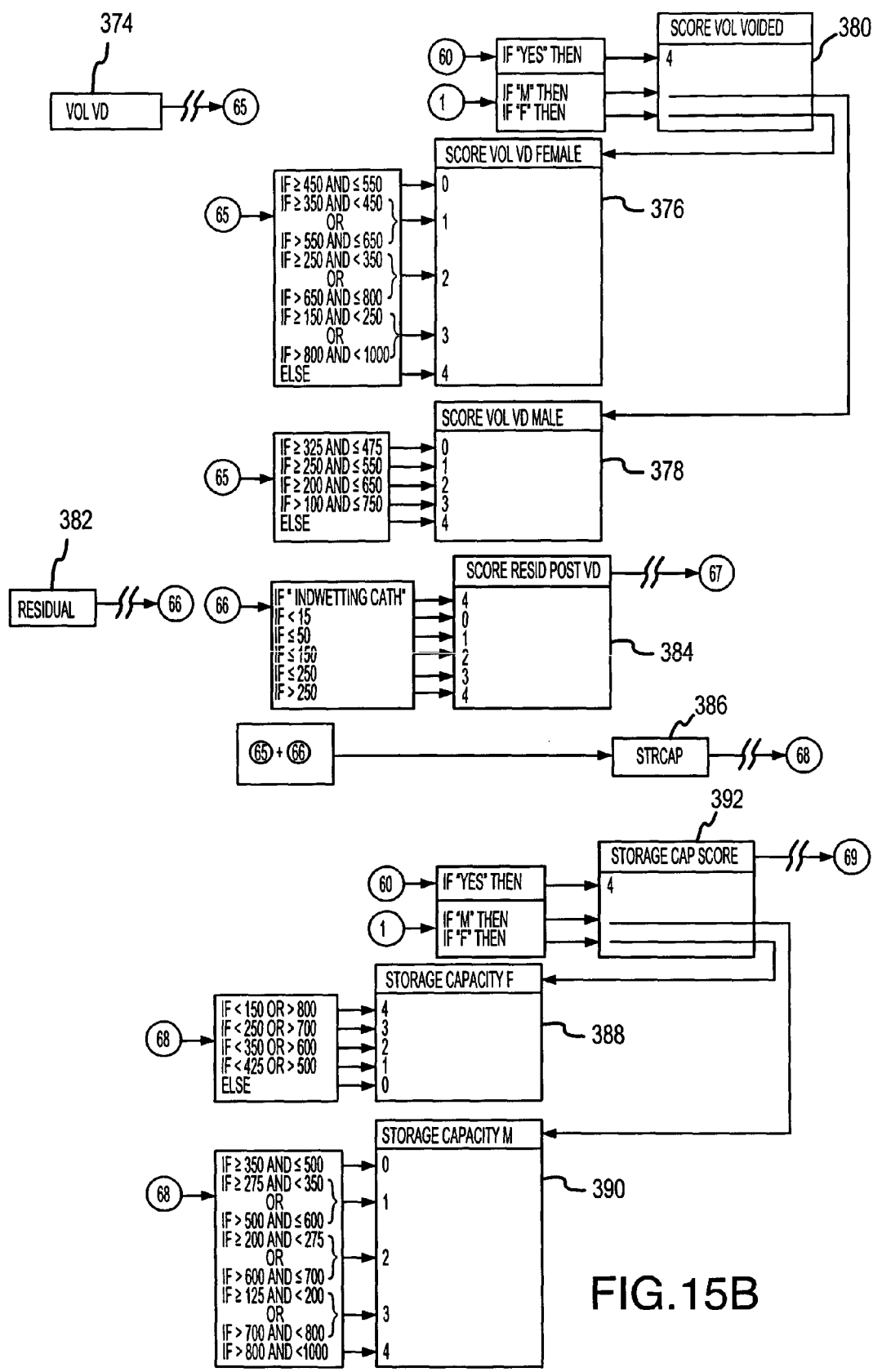
Figure 35:
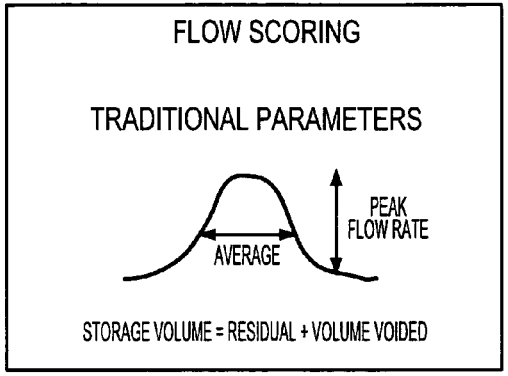
FIG. 35 is a representation of the traditional parameters considered in scoring flow related data.

Referring to FIGS. 15A, 15B, and 35, the first measurement scored is the peak flow rate in field 362 (FIG. 15A). This score is based upon multiple criteria, including whether the patient is male or female or presents with urinary retention. The actual measured flow rate is stored in field 356. Scores are distributed for a female flow rate in field 358 in decrements of 5 cc/sec from 30 cc/sec (i.e., ≧30 cc/sec=0; ≧25 cc/sec and <30 cc/sec=1; ≧20 cc/sec and <25 cc/sec=2; ≧15 cc/sec and <20 cc/sec=3; and <15 cc/sec=4) and transferred to field 362. For males, the high-end flow rate is 25 cc/sec and the scoring is altered as follows: ≧25 cc/sec=0; ≧20 cc/sec and <25 cc/sec=1; ≧15 cc/sec and <20 cc/sec=2; ≧10 cc/sec and <15 cc/sec=3; and <10 cc/sec=4. However, for males if the storage capacity calculated in field 386 (FIG. 15B) is ≦80 cc, a score of 0 is entered in field 360 (FIG. 15A) regardless of the flow rate. The male peak flow rate score in field 360 is similarly transferred to the general peak flow rate score field 362. This general score may additionally be overridden and replaced with a score of 4 if a "Yes" value is entered in field 354 noting that the patient presents with urinary retention.

In addition to the peak flow rate, the average flow rate is recorded in field 364 and scored. Scoring for the average flow rate is similarly differential between males and females. The average female flow is scored in field 366 based on decrements of 2 cc/sec as follows: >12 cc/sec=0; >10 cc/sec and ≦12 cc/sec=1; >8 cc/sec and ≦10 cc/sec=2; >6 cc/sec and ≦8 cc/sec=3; and ≦6 cc/sec=4. The scoring for males is performed in field 368 in decrements of 3 cc/sec in recognition of the slower rate of male flow. The male scores are allocated as follows: >12 cc/sec=0; >9 cc/sec and ≦12 cc/sec=1; >6 cc/sec and ≦9 cc/sec=2; >3 cc/sec and ≦6 cc/sec=3; and ≦3 cc/sec=4. The female or male average flow rate score from either field 366 or 368, respectively, is transferred to the general score field for average flow rate, field 370. However, as with the peak flow rate score, if the patient exhibits urinary retention, an overriding score of 4 is entered into field 370.

The final actual flow calculation computes the ratio between average flow rate, field 364, and the peak flow rate, field 356. This ratio is multiplied by 100 to convert to a percentage figure that is stored in field 372 (FIG. 15A).

Related to the flow rate of a void occurrence is the actual volume voided. The measurement of such volume is held in field 374 (FIG. 15B). Translating the volume measurement into a score is again subject to differentiation between male and female patients. Scoring for female patients is performed in field 376 as follows: ≧450 cc and ≦550 cc=0; ≧350 cc and <450 cc or >550 cc and ≦650 cc=1; ≧250 cc and <350 cc or >650 cc and ≦800 cc=2; ≧150 cc and <250 cc or >800 cc and <1000 cc=3; and <150 cc or >1000 cc=4. Male scoring in field 378 is similar: ≧325 cc and ≦475 cc=0; ≧250 cc and <325 cc or >475 cc and ≦550 cc=1; ≧200 cc and <250 cc or >550 cc and ≦650 cc=2; >100 cc and <200 cc or >650 cc and ≦750 cc=3; and ≦100 cc or >750 cc=4. Either the male or female void volume score is lodged in field 380, as appropriate, with the exception of an overriding score of 4 in the instance of urinary retention in the patient.

Once a patient has voided, there may be some residual volume in the bladder, which is measured via a catheter, field 382 (FIG. 15B). Residual volume is scored between 0 and 4 as follows: <15 cc=0; ≧15 and ≦50 cc=1; >50 cc and ≦150 cc=2; >150 cc and ≦250 cc=3; >250 cc=4. If the patient is equipped with an indwelling catheter, this is noted in field 382, and a score of 4 is automatically charged to field 384.

The actual storage capacity of the bladder, field 386 (FIG. 15B), is therefore the sum of the residual volume of field 382 and the voided volume of field 374. A total storage capacity score is then generated specifically for females and males in fields 388 and 390, respectively. Total storage capacity for a female is score as follows: ≧425 cc and ≦500 cc=0; ≧350 cc and <425 cc or >500 cc and ≦600 cc=1; ≧250 cc and <350 cc or >600 cc and ≦700 cc=2; ≧150 cc and <250 cc or >700 cc and ≦800 cc=3; and <150 cc or >800 cc=4. For a male, the scores change as follows: ≧350 cc and ≦500 cc=0; ≧275 cc and <350 cc or >500 cc and ≦600 cc=1; ≧200 cc and <275 cc or >600 cc and ≦700 cc=2; ≧125 cc and <200 cc or >700 cc and ≦800 cc=3; and <125 cc or >800 cc=4. Depending upon the sex of the patient, the appropriate score is stored in field 392 (FIG. 15B), with the proviso that an overriding score of 4 is entered if the patient exhibits urinary retention.

b) Subjective Scoring

Figure 16:
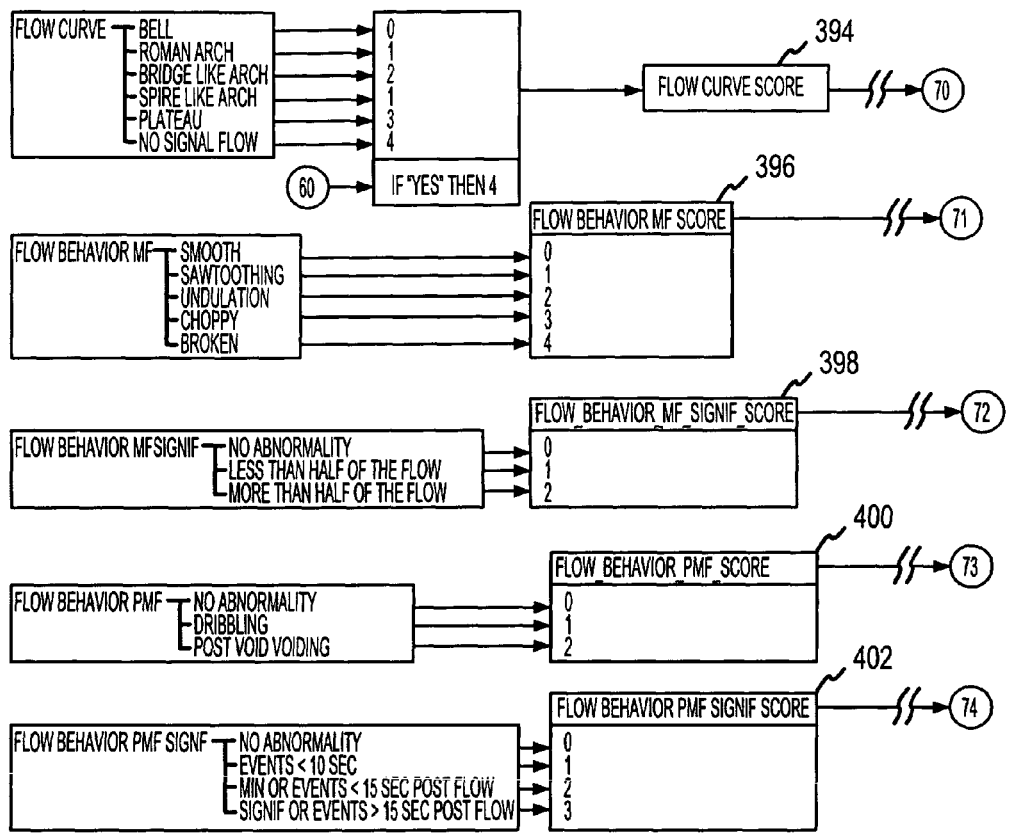
FIG. 16 is a portion of a database field chart depicting fields related to subjective flow rate measurements and scores.
Figure 36:
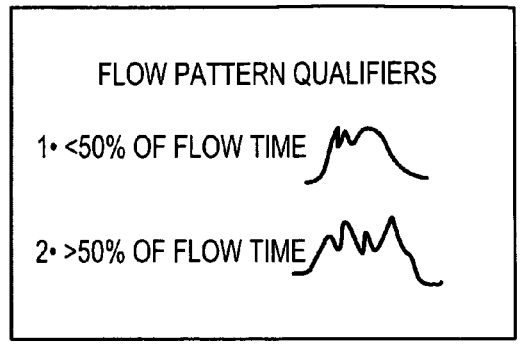
FIG. 36 is a depiction of qualifiers impacting the analysis of flow patterns.
Figure 37:
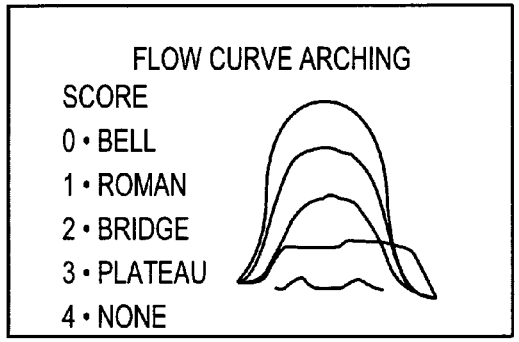
FIG. 37 is a representation of possible normal and dysfunctional flow curves.

Attendant with the flow and volume measurements related to flow rate are several subjective observations that add to the diagnostic value of the UPP diagnostic program. These subjective scoring factors are depicted in FIG. 16. First is an indication of the graphic curve of the flow rate as measured against time over the void period, field 394 and FIG. 36. A normal flow curve is bell-shaped, as shown in FIG. 37, and receives a score of zero. More pronounced curves typified by a Roman arch or spire arch shapes are awarded 1 point. A bridge-like arch is awarded 2 points. A plateau-shaped curve is scored at 3 points. If there is no significant flow, e.g., a dribble, 4 points are entered for the score. And again, if the patient exhibits urinary retention, a score of 4 supplants any other score for this field.

Figure 38:
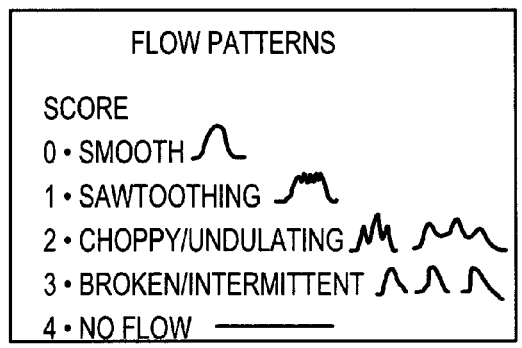
FIG. 38 is a representation of possible normal and dysfunctional flow patterns.

In addition to the overall shape of the flow curve, the line comprising the curve itself may not be smooth, but instead exhibit unsteady characteristics as shown in FIG. 38. This flow pattern or behavior is scored, based on its appearance, in field 396 (FIG. 16). Different possible flow patterns and related scores are as follows: smooth=0; saw-toothed=1; undulating=2; choppy=3; and broken=4. An unsteady flow pattern may be exhibited for merely a portion of the void period, or it may be present throughout. The relative duration of any exhibited flow pattern is captured in field 400 (FIG. 16). If there is no abnormality, i.e., a smooth flow pattern, a 0 score is recorded. If an abnormal pattern is present for less than half of the flow period, a score of 1 is attributed. If the unsteady flow pattern is present for greater than half the void time, a score of 2 is awarded. As noted before, with appropriate pattern recognition software used in conjunction with the UPP diagnostic program, these flow curves and patterns could be automatically recorded and scored without clinician input.

Figure 17:
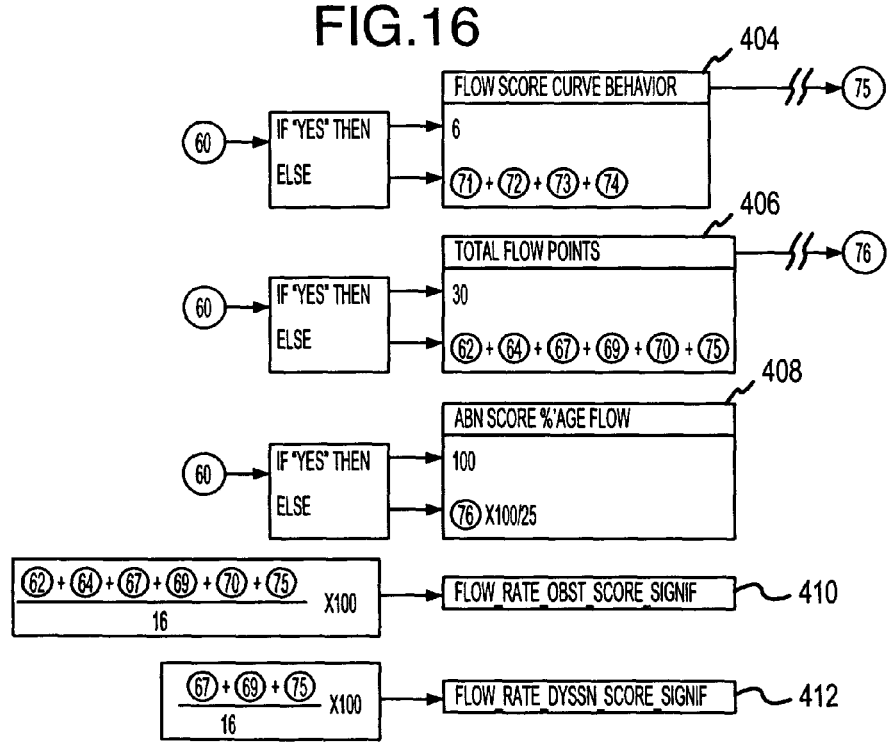
FIG. 17 is a portion of a database field chart depicting fields related to summary scoring for flow rate measurements.
Figure 39:
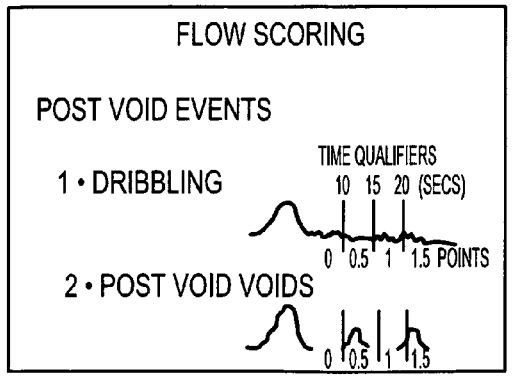
FIG. 39 is a representation of elements considered in scoring post void events.

In addition to the normal void period, the patient may exhibit a post main void flow event. (See FIG. 39.) Such an event is generally dribbling, or post main void flow voiding. The former, if present, is scored as 1 point in field 402 (FIG. 16), and the latter is scored as 2 points. If there is no abnormal post void event, the value of field 402 is null. The duration of any post void event is also characterized as to its significance and scored in field 404 (FIG. 17). No abnormality receives a score of 1. An event of less than 10 seconds rates 0.5 point. An event of between 10 and 15 seconds is minimal and scored as 1 point. If the post void event is significant or greater than 15 seconds in duration is allocated 2 points.

c) Flow Rate Assessment Summary

Once the flow rate information is recorded and the related scores are calculated, the UPP diagnostic program generates summary scores as seen in FIG. 17. A summary flow curve pattern or behavior score is calculated in field 404. The flow curve behavior score is the sum of the behavior score, field 396 (FIG. 16), the behavior significance score, field 398, the post main flow void score, field 400, and the post void significance score, field 402. If the patient exhibits urinary retention, the calculation is bypassed and a score of 6 is recorded.

A total flow rate point score is also generated in field 406 (FIG. 17). This adds the flow curve behavior score calculated in field 404 to the peak flow rate score, field 362 (FIG. 15A), the average flow rate score, field 370, the residual volume score, field 384 (FIG. 15B), the total capacity score, field 392, and the flow curve score, field 394 (FIG. 16). Again, if the patient exhibits urinary retention, the summed scored is discarded in favor of a set score of 30. This total flow rate score is converted to a percentage in field 408 (FIG. 17) to indicate the degree of abnormality noted by the UPP study. A patient with urinary retention is automatically labeled as 100 percent abnormal.

Two more calculations can be performed to indicate an obstruction significance related to the flow rate, and a dyssynergia significance related to flow rate. Obstruction significance is calculated in field 410 by summing the peak flow rate score, field 362 (FIG. 15A), the average flow rate score, field 370, the residual volume score, field 384 (FIG. 15B), and the flow curve score, field 394 (FIG. 16), and converting to a percentage of the total points possible from those fields. Dyssynergia significance is similarly calculated by adding the residual volume score, field 384 (FIG. 15B), the total capacity score, field 392, and the flow curve behavior score calculated, field 404 (FIG. 17), and converting to a percentage of the total points possible from those fields.

Diagnosis and Treatment

The scores from all three major categories of investigation—urethra, bladder, and flow—are used by the UPP diagnostic program to give a study abnormality weighting as a total score and as a percent of total abnormality possible. More importantly, various combinations and weightings from the three sections provide a computerized differential diagnosis and recommendation for investigation and therapy of a particular patient's condition. These recommendations are calculated based on long-term study and compilation of patient data to draw quantitative correlations between patient profiles, symptoms, and objective examination measurements, and by translation of this data into quantitative rules to classify and indicate discrete disease diagnoses and related treatments. The scores may be adjusted for biases in a particular patient study, or updated to reflect changes in norms or definitions of particular pathologies resulting from further clinical study, but typically the weightings should change no more than 5-10 percent. Even if the norms are changed, for example, to account for a specific group under study or to place a patient within norms for an age group, the scoring system of the invention does not change. If the computer does not offer a diagnosis, or in the case of need to supplement the choices given by the computer, the clinician may choose up to several diagnoses from a list of additional possibilities.

Further, specific summaries of data profiles can be assembled from the patient information collected in the database by the program. These summaries can profile urinary related conditions of various groups related by disease, gender, age, or therapeutic treatment. Examples of groupings could be as follows: 1) Multiple Sclerosis—presenting degree of spasticity of bladder and sphincter by age (decade); 2) Incontinent Females <50 years—determining sphincter closure pressures by age (decade); 3) Males with Prostate Obstruction—determination of degree of outlet blockage by age (decade); 4) Pelvic Pain Patients—efficacy of treatment regimes on spasticity and performance of bladder (pre and post treatment); and 5) Botox Patients—evaluation of efficacy of new therapies (pre and post treatment). This is just a short sample list of a myriad of groups the UPP diagnostic program could monitor.

In addition, sphincter dynamics, although not necessary for the diagnosis process herein, can be used to refine the results of a patient study. More importantly, sphincter dynamics data can be significant in the analysis of drug trials or other treatment trials for treatment of urinary tract dysfunctions wherein increased accuracy of all treatment effects is desired. Sphincter dynamics study considers sphincter stability, relaxation, and pressure during fill, during void, and post void, and the present program would similarly score the results of each facet of the study and incorporate the calculations into the diagnostic criteria.

The various diagnoses and treatment recommendations calculated by the program, as well as the non-automated supplemental choices, are catalogued below.

AUTOMATED DIAGNOSIS

I. Prostate Disorders

A. Benign Prostatic Hyperplasia (Prostate Obstruction Alone)

Diagnosis:

If(Sex="M", If(Age $\geq$45, If(UPP Dysfunct'l Score$\leq$15, If(Stress Leak Risk$\leq$10, If(Obstr_Score_%_M$\geq$5, If(Cap at Vd Attpt$\geq$350, If(Presenting_Sx$\neq$"Pelvic pain", If(Bladder Vol 1<5, If(Neurogenic Status_Sx="Non-Neurogenic", "¶Bladder Outlet Obstruction.", " "), " "), " "), " "), " "), " "), " "), " ")

If(C_Dx_BPH="¶Bladder Outlet Obstruction.", "¶The most likely diagnosis is that of an obstructive prostate, i.e., benign prostatic hyperplasia or BPH." & "It does not exclude the presence of prostatic cancer. Bladder neck hypertrophy may exist as part of the problem, but is unlikely to be present in the presence of a normal bladder capacity.", " ")

Recommended Treatment:

If(C_Dx_BPH="¶Bladder Outlet Obstruction.", "¶Given the age of the patient, enlargement of the prostate and/or hypertrophy of the bladder neck should be considered. TUPR or transurethral prostatectomy according to prostatic size or other risk factors may be indicated once conservative measures have been exhausted.", " ")

B. BPH with Sphincter/Pelvic Floor Dyssnergia

Diagnosis:

If(Sex="M", If(Age$\geq$45, If(Neurogenic_Status_Sx="Non-Neurogenic", If(Obstr_Score_%_M$\geq$10, If(UPP Dysfunct'l Score$\geq$10, If(Cap at Vd Attpt$\geq$200, If(Stress Leak Risk M$\leq$5, If(Compliance_at_Capacity<5, If(Bladder Vol 1<5, "¶Bladder Outlet Obstruction (BPH), with External Sphincter Over-Reactivity.", " "), " "), " "), " "), " "), " "), " "), " "), " ")

Recommended Treatment:

If(C_Dx_BPH_SphDys="¶Bladder Outlet Obstruction (BPH), with External Sphincter Over-Reactivity.", "¶An initial conservative approach should be tried to decrease outlet spasticity. An alpha blocker (e.g., Minipress)+/−a muscle relaxant (e.g., Valium) are often effective in combination. Minipress 1 mgm hs qd and Valium 5-10 mgm bid is one suggestion." & "¶" & "Once irritative symptoms are settled down, surgical approaches can be considered. Spinal or local block anesthesia is recommended, as due to pre-existing irritative symptoms, surgery can aggravate the underlying void dysfunction over the long term. This is due to CNS wind-up phenomena. Bladder capacity is functionally reduced because of increased tonicity and sensitivity of the bladder and sphincter.", " ")

C. BPH with Sphincter/Pelvic Floor Dyssnergia/Decreased Detrusor Compliance

Diagnosis:

If(Sex="M", If(Neurogenic_Status_Sx="Non-Neurogenic", If(Age$\geq$45, If(Obstr_Score_%_M$\geq$10, If(UPP Dysfunct'l Score$\geq$10, If(Cap at Vd Attpt$\leq$349, If(Compliance at Capacity$\geq$5, If(Bladder Vol 1<5, "¶Bladder Outlet Obstruction (BPH), with External Sphincter Spasticity and Poor Bladder Compliance.", " "), " "), " "), " "), " "), " "), " "), " ")

Recommended Treatment:

If(C_Dx_BPHSphDysCompl="¶Bladder Outlet Obstruction (BPH), with External Sphincter Spasticity and Poor Bladder Compliance.", "¶Surgical treatment of the outlet obstruction is recommended. However, the compliance limitation of the bladder may compromise the symptom relief. A period of medical management may be indicated. Hence an anticholinergic (e.g., Ditropan 5 mgm qd)+/−an alpha blocker (e.g., Minipress 1 mgm qd) should be tried prior to any surgical approaches.", " ")

D. Post Prostatectomy Incontinence

Diagnosis:

If(Sex "M", If(Presenting_Sx="Incontinence", If(Neurogenic_Status_Sx="Non -Neurogenic", If(Age$\geq$50, If(Stress Leak Risk$\geq$25, If(Compliance_Signif="Normal or Acceptable", If(Cap at Vd Attpt$\geq$350, If(Status="Post-Op", "¶Intrinsic Sphincter Weakness related to Prostate Surgery.", " "), " "), " "), " "), " "), " "), " ")

If(C_Dx_IncProst="¶Intrinsic Sphincter Weakness related to Prostate Surgery.", "¶This Dx implies that intrinsic external urethral sphincter damage is the primary cause of stress related urinary incontinence. Bladder compliance is normal.", " ")

Recommended Treatment:

If(C_Dx_IncProst="¶Intrinsic Sphincter Weakness related to Prostate Surgery.", "¶" & "An artificial sphincter remains the treatment of choice." & "¶" & "Collagen injected into the prostatic fossa can be tried in very mild cases, but success rates have been poor.", " ")

E. BPH with Sphincter/Pelvic Floor Dyssnergia/Detrusor Overactivity

Diagnosis:

If(Sex="M", If(Age$\geq$45, If(Neurogenic Status Sx="Non-Neurogenic", If(Obstr_Score_%_M$\geq$10, If(UPP Dysfunct'l Score$\geq$10, If(Cap at Vd Attpt$\leq$400, If(Bladder Vol 1$\geq$5 or Cap at Vd Attpt$\leq$200, If(Stress Leak Risk M$\leq$4, "¶Bladder Outlet Obstruction (BPH), with External Sphincter Spasticity and Detrusor Instability &/or Hypersensitivity.", " "), " "), " "), " "), " "), " "), " "), " ")

Recommended Treatment:

If(C_Dx_BPHSphDysBlInst.="¶Bladder Outlet Obstruction (BPH), with External Sphincter Spasticity and Detrusor Instability &/or Hypersensitivity.", "¶An initial conservative approach using an appropriate anticholinergic, an alpha blocker, and pelvic floor relaxation exercises, is recommended. Ditropan 5 mgm t.i.d and Minipress 1 mgm hs qd is suggested. Valium 5 mgm qd might also be used for anxious patients. Once irritative symptoms are settled down, surgical management via prostatectomy (TUPR, RRP, RPP) should be considered.", " ")

F. Post Prostatectomy Incontinence with Decreased Bladder Compliance

Diagnosis:

If(Sex="M", If(Age$\geq$45, If(Presenting_Sx="Incontinence", If(Stress Leak Risk$\geq$5, If(Compliance Signif$\neq$ "Normal or Acceptable", If(Neurogenic_Status_Sx="Non-Neurogenic"If(Status="Post-Op", "Post Prostatectomy Stress Incontinence with Reduced Bladder Compliance.", " "), " "), " "), " "), " "), " ")

Recommended Treatment:
If(C_Dx_Inc_Prost_Cap="¶Post Prostatectomy Stress Incontinence with Reduced Bladder Compliance.", "¶" & "While approaches to management of sphincter weakness can be tried, it is recommended that initial steps to be taken to minimize storage pressure within the bladder. Options include Ditropan, frequent voids, or augmentation cystoplasty. If successful, then an artificial sphincter would be the procedure of choice.", " ")

G. BPH and Stress Incontinence (Sphincter Weakness Prior to Surgery)

Diagnosis:
If(Stress Leak Risk≧10, If(Sex="M", If(Age≧45, If(Neurogenic_Status_Sx="Non-Neurogenic", If(Obstr_Score_%_M≧10, If(Compliance_at_Capacity≦5, If(UPP Dysfunct'l Score≦9, If(Cap at Vd Attpt≧200, If(Status≠"post-op", "¶Outlet Obstruction and a Weak External Urethral Sphincter Mechanism.", " "), " "), " "), " "), " "), " "), " "), " "), " ")

Recommended Treatment:
If(C_Dx_BPH_Stress="¶Outlet Obstruction and a Weak External Urethral Sphincter Mechanism.", "¶A cystoscopy and/or a VCUG (voiding cystourethrogram) should be performed to document SIGNIFICANT obstruction. As there is a significant weakness of the sphincter mechanism, an initial emphasis of therapy should be on conservation (i.e., alpha blockers and biofeedback) approaches." & "¶" & "The patient should be counseled regarding the risks of stress incontinence that might follow surgery (TURP, etc.). Surgery should be conservative. If, post-op, there is a clear stress component, an artificial sphincter may be necessary.", " ")

H. BPH with Detrusor Urge and Stress Incontinence (Sphincter Weakness)

Diagnosis:
If(Sex="M", If(Neurogenic_Status_Sx="Non-Neurogenic", If(Age≧45, If(Obstr_Score_%_M≧10, If(UPP Dysfunct'l Score≧10, If(Cap at Vd Attpt≦350, If(Stress Leak Risk M≧10, If(Bladder Vol 1≧5, "¶Bladder Outlet Obstruction (BPH), Bladder and External Sphincter Over-Reactivity and External Sphincter Weakness.", " "), " "), " "), " "), " "), " "), " "), " ")

Recommended Treatment:
If(C_Dx_BPH_DetrSphUrgeStress="¶Bladder Outlet Obstruction (BPH), Bladder and External Sphincter Over-Reactivity and External Sphincter Weakness.", "¶This patient should be treated with an anticholinergic (e.g., Oxybutynin 5-10 mgm b.i.d. or Detrol 1-2 mgm qd). Other medications may be added to help stabilize CNS regulation of void reflexes (e.g., Minipress 1 mgm hs and/or Valium 5 m mgm b.i.d.). Neurotoxin approaches (Capsaicin or Botox instillations) can be considered as well as sacral nerve stimulation to stabilize the bladder." & "¶" & "A cystoscopy and/or a VCUG (voiding cystourethrogram) should be performed to document any SIGNIFICANT obstruction." & "¶" & "As the primary problem lies with dysfunctional storage behavior, the emphasis of therapy should be on conservation approaches." & "Often the urge component is the predominant problem and efforts should be made to decrease the urge sensation before resorting to surgery." & "¶" & "Once irritative symptoms are settled down, surgical management can be considered." & "Spinal or local block anesthesia is recommended, as with pre-existing irritative symptoms, surgery can aggravate symptom over the long term. This is due to CNS wind-up phenomena. The patient should be counseled regarding the risks of stress incontinence and surgery should be conservative. If, post-op, there is a clear stress component, an artificial sphincter may be necessary." & "¶" & "However, there is significant risk of failure because of the overactive bladder. Modulation approaches are often required for the long term, alone or in combination. The patient should also understand the need to empty frequently.", " ")

I. BPH with Sphincter Urge/Stress Incontinence (Sphincter Weakness)

Diagnosis:
If(Sex="M", If(Age≧45, If(Neurogenic_Status_Sx="Non-Neurogenic", If(Obstr_Score_%_M≧10, If(UPP Dysfunct'l Score≧10, If(Cap at Vd Attpt≧200, If(Stress Leak Risk M≦5, If(Compliance_at_Capacity<5, If(Bladder Vol 1=<5, "¶Bladder Outlet Obstruction (BPH), with External Sphincter Over-Reactivity.", " "), " "), " "), " "), " "), " "), " ") " "), " ")

Recommended Treatment:
If(C_Dx_BPH_SphDys="¶Bladder Outlet Obstruction (BPH), with External Sphincter Over-Reactivity.", "¶An initial conservative approach should be tried to decrease outlet spasticity. An alpha blocker (e.g., Minipress)+/−a muscle relaxant (e.g., Valium) are often effective in combination. Minipress 1 mgm hs qd and Valium 5-10 mgm bid is one suggestion." & "¶" & "Once irritative symptoms are settled down, surgical approaches can be considered. Spinal or local block anesthesia is recommended, as due to pre-existing irritative symptoms, surgery can aggravate the underlying void dysfunction over the long term. This is due to CNS wind-up phenomena. Bladder capacity is functionally reduced because of increased tonicity and sensitivity of the bladder and sphincter.", " ")

J. BPH with Sphincter Urge/Stress Incontinence (Normal Bladder)

Diagnosis and Recommended Treatment:
If(Sex="M", If(Neurogenic_Status_Sx="Non-Neurogenic", If(Age≧45, If(Obstr_Score_%_M≧10, If(UPP Dysfunct'l Score≧10, If(Cap at Vd Attpt>250, If(Stress Leak Risk M≧10, If Bladder Vol 1=" ", "¶Bladder Outlet Obstruction (BPH), External Sphincter Sensory-Motor Overactivity, External Sphincter Weakness, but Bladder Activity Within Normal Limits." & "¶" & "An initial conservative approach should be tried to decrease outlet spasticity. An alpha blocker (e.g., Minipress)+/−a muscle relaxant (e.g., Valium) are often effective in combination. Minipress 1 mgm hs qd and Valium 5-10 mgm bid is one suggestion." & "¶" & "Once irritative symptoms are settled down, surgical approaches can be considered. Spinal or local block anesthesia is recommended, as due to pre-existing irritative symptoms, surgery can aggravate the underlying void dysfunction over the long term. This is due to CNS wind-up phenomena. Bladder capacity may be functionally reduced because of increased tonicity and sensitivity of the sphincter.", " "), " "), " "), " "), " "), " "), " "), " ")

K. BPH with Detrusor Overactivity

Diagnosis:
If(Sex="M", If(Age≧45, If(UPP Dysfunct'l Score≦15, If(Stress Leak Risk≦10, If(Obstr_Score_%_M≧5, If(Cap at Vd Attpt≦350, If(Presenting_Sx≠"Pelvic pain", If(Bladder Vol 1>5, If(Neurogenic_Status_Sx="Non-Neurogenic", "¶Bladder Outlet Obstruction with Detrusor Overactivity.", " "), " "), " "), " "), " "), " "), " "), " ")

Recommended Treatment:

If(C_Dx_BPH_DetrInst="¶Bladder Outlet Obstruction with Detrusor Overactivity.", "¶Given the age of the patient, enlargement of the prostate and/or hypertrophy of the bladder neck should be considered along with an overactive bladder. The Detrusor overactivity should be dampened with appropriate anticholinergic therapy. Ditropan, Ditropan XL, or Detrol are the most effective medications. Capsaicin or Resiniferitoxin (RTX) instillation may also be considered. Retention is a risk and therefore dosing should be undertaken in a ramped fashion. TUPR or retropubic prostatectomy according to prostatic size, or other risk factors, may be indicated once conservative measures have been exhausted.", " ")

L. BPH with Decreased Detrusor Compliance

Diagnosis:

If(Sex="M", If(Age≧45, If(Presenting_Sx="Incontinence", If(Stress Leak Risk≧5, If(Compliance_Signif≠"Normal or Acceptable", If(Neurogenic_Status_Sx="Non-Neurogenic", If(Status="Post-Op", "Post Prostatectomy Stress Incontinence with Reduced Bladder Compliance.", " "), " "), " "), " "), " "), " ")

Recommended Treatment:

If(C_Dx_BPH_Inc_Prost_Cap="¶Post Prostatectomy Stress Incontinence with Reduced Bladder Compliance.", "¶" & "While approaches to management of sphincter weakness can be tried, it is recommended that initial steps to be taken to minimize storage pressure within the bladder. Options include Ditropan, frequent voids, or augmentation cystoplasty. If unsuccessful, then an artificial sphincter would be the procedure of choice.", " ")

M. BPH with a Weak Detrusor and a Weak Sphincter

Diagnosis:

If(Cap at Vd Attpt>500 and B1 Press on Vd Attpt>10, If(Stress Leak Risk>10, If(Obstr_Score_%_M>10, If(UPP Dysfunct'l Score>10, "1) Present, but Attenuated Void Reflex, 2) Background of Dynamic Overactivity within Urethral Sphincter, and 3) Outlet Obstruction.", " "), " "), " "), " ")

Recommended Treatment:

If(C_Dx_BPH_DetrHypo_Sph InstWkness_OutletObstr'n="1) Present, but Attenuated Void Reflex, 2) Background of Dynamic Overactivity within Urethral Sphincter, and 3) Outlet Obstruction.", "¶Neuroreflex regulation, as evidenced by a flat CMG, weak volitional bladder contraction, and low basal urethral pressures, is significantly compromised. There is background unstable activity in the dynamic sphincter (EMG) recording. This combined with the weakened tonus suggests a chronic process, e.g., a long-standing and dyscoordinate void habit. Consistent with this is the obvious dyssenrgia in the void attempt. Finally, there is obvious prostatic obstruction that should be confirmed." & "¶" & "As some reflex void activity remains, there is a possibility of void recovery after relief of the obstruction. The patient should be cystoscoped and a decision as to surgery made. The dyssnergic, overactive sphincter should be managed with use of alpha blockers and biofeedback with e-stim. If a TURP is done, the degree of necessary resection can be gauged by performing periodic crede flow studies during the procedure. This approach can help protect against over-resection and adding to his predisposed risk of incontinence.", " ")

N. Non Specific Outlet Obstruction

Diagnosis:

If(Age≧45, If(Obstr_Score_%_M≧10, If(Neurogenic_Status_Sx="Non-Neurogenic", "¶Bladder Outlet Obstruction.", " "), " "), " ")

Recommended Treatment:

If(C_Dx_Obstr'n="¶Bladder Outlet Obstruction.", "¶Cystoscopy is recommended to assess what appears to be significant outlet obstruction on the urethral pressure profile.", " ")

II. Incontinence

A. Female Stress Incontinence

Diagnosis:

If(Sex="F", If(Stress Leak Risk≧20, If(Neurogenic_Status_Sx="Non-Neurogenic", If(Age≧15, If(Presenting_Sx="Incontinence" or Presenting Sx_2°="Incontinence", If(Presenting_Sx≠"Pelvic Pain", If(Presenting Sx_2°≠"Pelvic Pain", If(Compliance_Signif="Normal or Acceptable", If(Cap at Vd Attpt≧300, If(UPP Dysfunct'l Score≦10, "Urinary Stress Incontinence with Insignificant Urge.", " "), " "), " "), " "), " "), " ") " "), " "), " "), " ")

If(C_Dx_Inc_Stress_F="Urinary Stress Incontinence", "¶" & "This Dx implies a performance weakness of the external urethral sphincter, in the presence of good bladder storage and compliance.", " ")

Recommended Treatment:

If(C_Dx_Inc_Stress_F="Urinary Stress Incontinence with Insignificant Urge.", If(Pk_Ur_Press≦50, "¶" & "There is significant sphincter weakness evident on the urethral pressure profile. This may represent either intrinsic failure of muscle, or a failure of CNS sphincter memory, or both. Cystoscopy and a pelvic exam are recommended as surgery may be indicated for repair of weakened support." & "¶" & "If there is any element of urge, this should be treated prior to surgery as the urge symptom may be aggravated by surgery." & "¶" & "Intra-urethral (collagen/fat) injection therapy is recommended as management of pure intrinsic sphincter deficiency and normal bladder compliance.", " "), " "), B. Detrusor Urge Incontinence Diagnosis:

If(Presenting_Sx="Incontinence" or Presenting_Sx="Frequency", If(Bladder Vol 1≦350, If(Stress Leak Risk≦10, If(UPP Dysfunct'l Score≦20, "¶Incontinence Secondary to Overactive Bladder", " "), " "), " "), " ")

Recommended Treatment:

If(C_Dx_DetrUrgeInc="¶Incontinence Secondary to Overactive Bladder", "¶This patient should be treated with an anticholinergic (e.g., Oxybutynin 5-10 mgm b.i.d. or Detrol 1-2 mgm qd). Other medications may be added to help stabilize CNS regulation of void reflexes (e.g., Minipress 1 mgm hs and/or Valium 5 m mgm b.i.d.)." & "¶" & Neurotoxin approaches (Capsaicin or Botox instillations) can be considered as well as sacral nerve stimulation to stabilize the bladder. A cystoscopy and/or a VCUG (voiding cystourethrogram) should be performed to document any SIGNIFICANT cystocole." & "¶" & As the primary problem lies with dysfunctional storage behavior, the emphasis of therapy should be on conservation therapies.", " ")

C. Detrusor Urge with Sphincter Weakness Incontinence (Female)

Diagnosis:

If(Sex="F",If(Stress Leak Risk>10, If(Neurogenic_Status_Sx="Non-Neurogenic", If(Presenting_Sx="Incontinence" or Presenting_Sx="Urinary Frequency", If(Compliance_at_Capacity≧5 or Bladder Vol 1>1, "¶Urge and Stress Urinary Incontinence", " "), " "), " "), " "), " ")

Recommended Treatment:

If(C_Dx_DetrUrge_SphStress_F="¶Urge and Stress Urinary Incontinence", "¶Often the urge component is the predominant problem and efforts should be made to decrease the urge sensation before resorting to surgery. If there is a clear stress component, anatomical correction may be necessary. However, there is often intrinsic weakness of the sphincter that does not improve with bladder suspension surgery. Modulation approaches (e.g., anticholinergics/neurotoxin therapy or sacral nerve stimulation) are therefore often required, alone or in combination with suspension or bulking surgery. The patient should also understand the need to empty frequently the detrusor overactivity.", " ")

D. Sphincter Urge Incontinence and Recommended Treatment

Diagnosis and Recommended Treatment:

If(Stress Leak Risk≦20, If(Neurogenic_Status_Sx="Non-Neurogenic", If(Presenting_Sx="Incontinence" or Presenting_Sx="Urinary Frequency", If(Presenting Sx_2°≠"Pelvic Pain", If(Compliance_Signif="Normal or Acceptable", If(Bladder Vol 1<2, If(UPP Dysfunct'l Score>10, "Sphincteric Instability with Urge Incontinence." & "¶" & "Treatment should focus primarily on reducing excitability of the sphincter. Hence, somatic reflex activity should be treated with choices that include biofeedback, alpha blockers, and anti-anxiety meds." & "¶" & "The bladder can be intermittently overactive because of spontaneous relaxation of the sphincter and disinhibition of the bladder. An anticholinergic can therefore be tried along with the other meds mentioned. However, not uncommonly, the bladder does not respond to medication if overactivity is tied to a somatic trigger. In such cases, neuromodulation (i.e., pelvic floor e-stim or sacral foramen stimulation) is a good option to consider.", " "), " "), " "), " "), " "), " ")

E. Detrusor Urge/Sphincter Urge

Diagnosis & Recommended Treatment:

If(Presenting_Sx="Incontinence" or Presenting Sx_2°="Incontinence", If(Bladder Vol 1≧2, If(Stress Leak Risk≦10, If(UPP Dysfunct'l Score≧15, "¶Incontinence Secondary to Overactive Sphincter and related Overactivity of the Bladder." & "¶" & "Treatment should address both the heightened excitability of the sphincter and the bladder. Hence, somatic reflex activity should be treated with choices that include biofeedback, alpha blockers, and anti-anxiety meds." & "The bladder can be suppressed with an anticholinergic. Not uncommonly, the bladder does not respond to medication if overactivity is tied to a somatic trigger. In such cases, neuromodulation is a good option to consider.", " "), " "), " "), " ")

F. Detrusor and Sphincter Urge Incontinence with Sphincter Weakless Male

Diagnosis:

If(Type of Surgery≠"TURP—Post", If(Stress Leak Risk≧10, If(Age≧15, If(Presenting_Sx="Incontinence" or Presenting_Sx="Urinary Frequency", If(Presenting Sx_2°≠ "Pelvic pain", If(Obstr_Score_%_M≦5, If(UPP Dysfunct'l Score>5, If(Neurogenic_Status_Sx="Non-Neurogenic", If(Compliance_at_Capacity≧8 or Bladder Vol 1>5, "¶¶Urge and Stress Urinary Incontinence", " "), " "), " "), " "), " "), " "), " "), " ")

Recommended Treatment:

If(C_Dx_DetrSphUrge_Stress_M="¶¶Urge and Stress Urinary Incontinence", "¶Often the urge component is the predominant problem and efforts should be made to decrease the urge sensation before resorting to surgery. If there is a clear stress component, an artificial sphincter can be considered providing the patient understands the need to empty frequently and efforts are taken to control (e.g., Detrol or Ditropan) the detrusor overactivity.", " ")

G. Non Specific Sphincter Weakness

Diagnosis:

If(Stress Leak Risk≧5 and Obstr_Score_%_M<5, "¶" & "There is evidence of sphincteric weakness that may or may not be clinically relevant. Nevertheless, the finding is significant. It is evidence of a compromise in neuro-regulation of the pelvic floor and urethral sphincter." & "¶" & "The patient is at risk for eventual development of incontinence if indeed the problem is not already manifest.", " ")

III. Urethral Instability and Pelvic Pain

A. Spastic Urethra (Urge Without Pain)

Diagnosis:

If(Presenting_Sx≠"Pelvic Pain" and Presenting Sx_2°≠"Pelvic Pain", If(Compliance_Signif="Normal or Acceptable", If(Neurogenic_Status_Sx="Non-Neurogenic", If(Cap at Vd Attpt≧300, If(UPP Dysfunct'l Score≧10, If(Bladder Vol 1<2, If(Sensitivity="no pain", "¶Spastic Dysfunction of the External Urethral Sphincter.", " "), " "), " "), " "), " "), " ")

Recommended Treatment:

If(C_Dx_Spastic_Urethra="¶Spastic Dysfunction of the External Urethral Sphincter", & "¶" & "This Dx implies instability of the external urethral sphincter. The problem is primarily motor as there was little to no significant sensitivity of the lower urinary tract tissues. The external urethral sphincter was found to have been behaviorally overactive during filling, dynamically hyperreflexic, or dyssnergic during the void effort." & "¶" & "There can be a spectrum of symptoms that include urinary frequency, incontinence, or urinary retention, all arising from dyscoordinate or precipitate sphincter relaxation of the urethral sphincter and/or the pelvic floor. Bowel dysfunction is commonly present and should be addressed as part of the management approach. There is a high probability of poor voluntary regulation of the levator muscles." & "¶" & "Treatment should be aimed at improving the contraction—relaxation dynamics of the pelvic floor, and decreasing overfacilitated, inefficient CNS circuits. Hence, a medication cocktail of Elavil, Minipress, and Xanax, or related drugs, is useful when combined with an intensive biofeedback effort. If this is unsuccessful then other more direct modulation approaches can be tried (e.g. pelvic floor e-stim or foramen stimulation)." & "¶" & "For severe anxiety personalities, professional counseling is a useful supportive measure.", " ")

B. Spastic Hypersensitve Urethra

Diagnosis:

If(Presenting_Sx≠"Pelvic Pain" or Presenting Sx_2°≠"Pelvic Pain", If(Compliance_Signif="Normal or Acceptable", If(Cap at Vd Attpt≧300, If(Neurogenic_Status_Sx="Non-Neurogenic", If(UPP Dysfunct'l Score≧5, If(Bladder Vol 1<2, If(Sensitivity="marked" or Sensitivity="minimal", "¶Hyperactive, Hypersensitive External Urethral Sphincter.", " "), " "), " ") " "), " "), " "), " ")

Recommended Treatment:

If(C_Dx_Spastic_Urethra2="¶Hyperactive, Hypersensitive External Urethral Sphincter.", & "¶" & "This Dx implies a diffuse breakdown in reflex regulation of the pelvic floor and external urethral sphincter. The external urethral sphincter was found to have been behaviorally overactive during filling, dynamically hyperreflexic, or dyssnergic during the void effort. The problem is both motor and sensory, as there was significant sensitivity of the sphincter zone to movements of the urodynamic catheter." & "¶" & "There can be a spectrum of symptoms that include urinary frequency, incontinence, urinary retention, or pain, all arising from dyscoordinate or precipitate sphincter relaxation of the urethral sphincter and/or the pelvic floor. There is a high probability of poor voluntary regulation of the levator muscles." & "¶" & "Treatment should be aimed at improving the contraction—relaxation dynamics of the pelvic floor, and decreasing overfacilitated, inefficient CNS circuits. Hence, a medication cocktail of Elavil, Minipress, and Xanax, or related drugs, is useful when combined with an intensive biofeedback effort. If this is unsuccessful then other more direct modulation approaches can be tried (e.g., pelvic floor e-stim or foramen stimulation)." & "¶" & "For severe anxiety personalities, professional counseling is a useful supportive measure.", " ")

C. Pain and Sphincter Weakness

Diagnosis:

If(Presenting_Sx="Incontinence" or Presenting Sx_2°="Incontinence", If(Presenting_Sx="Pelvic Pain" or Presenting Sx_2°="Pelvic Pain", If(UPP Dysfunct'l Score≧10, If(Bladder Vol 1≦2, If(Cap at Vd Attpt≦200, If(Neurogenic_Status_Sx="Non-Neurogenic", If(Stress Leak Risk≧10, "¶Pelvic Pain with Increased Pelvic Sensitivity and Sphincter Weakness.", " "), " "), " "), " "), " "), " "), " ")

Recommended Treatment:

If(C_Dx_Pain_Stress="¶Pelvic Pain with Increased Pelvic Sensitivity and Sphincter Weakness.", "¶The presence of pain suggests a significant neural disturbance that should be treated aggressively with medication or neuromodulation. Biofeedback programs can be applied or the patient considered for sacral nerve stimulation." & "¶" & "Urethral bulking agents may be considered for the sphincter weakness and bladder suspensions reserved for only significant descensus problems. Local blocks or spinal anesthesia should be used for surgical approaches because of the significant risk of wind-up and aggravation of pain.", " ")

D. Pain and Sphincter Urgency

Diagnosis:

If(Presenting_Sx="Pelvic Pain" or Presenting Sx_2°="Pelvic Pain", If(Neurogenic_Status_Sx="Non-Neurogenic", If(Bladder Vol 1≦2, If(Cap at Vd Attpt≧200, If(Stress Leak Risk≦10, If(UPP Dysfunct'l Score≧10, "¶Pelvic Pain with Significant Urethral Hyperexciteability and Sensitivity.", " "), " "), " "), " "), " "), " ")

Recommended Treatment:

If(C_Dx_Pain_SphUrge="¶Pelvic Pain with Significant Urethral Hyperexciteability and Sensitivity.", "¶The sensitivity and hyperactivity of the urethral striated sphincter is consistent with the symptom of pain and inefficiency in central synaptic signaling. There is no obvious neurological deficiency to explain the urinary frequency, or occasional incontinence. Most always this problem is tied to long standing inefficiency in pelvic floor relaxation." & "¶" & "Treatment should be aimed at improving the contraction—relaxation dynamics of the pelvic floor, and decreasing overfacilitated, inefficient CNS circuits. Hence, a medication cocktail of Elavil, Minipress, and Xanax, or related drugs, is useful when combined with an intensive biofeedback effort. If this is unsuccessful then other more direct modulation approaches can be tried (e.g., pelvic floor e-stim or foramen stimulation)." & "¶" & "For severe anxiety personalities, professional counseling is a useful supportive measure.", " ")

E. Pain and Urinary Retention

Diagnosis:

If(Presenting_Sx="Urinary Retention" or Presenting Sx_2°="Urinary Retention", If(Presenting_Sx="Pelvic Pain" or Presenting Sx_2°="Pelvic Pain", If(Bladder Vol 1≦2, If(Cap at Vd Attpt≦300, If(Neurogenic_Status_Sx="Non-Neurogenic", If(Stress Leak Risk≦20, If(UPP Dysfunct'l Score≧25, "¶Urethral Hyperexciteability and Sensitivity Contributing to Pelvic Pain and Urinary Retention.", " "), " "), " "), " "), " "), " "), " ")

Recommended Treatment:

If(C_Dx_Pain_Retention="¶Urethral Hyperexciteability and Sensitivity Contributing to Pelvic Pain and Urinary Retention.", "¶There is no obvious neurological deficiency to explain the urinary retention. The sensitivity and hyperactivity of the urethral striated sphincter is consistent with a symptom of pain, and an underlying inefficiency in central synaptic signaling." & "¶" & "The explanation for the retention lies in the inability of this compromised CNS circuitry to trigger a void reflex. Most always this problem is tied to long standing inefficiency in pelvic floor relaxation." & "¶" & "Treatment should be aimed at improving the contraction—relaxation dynamics of the pelvic floor, and decreasing overfacilitated, inefficient CNS circuits. Hence, a medication cocktail of Elavil, Minipress, and Xanax, or related drugs, is useful when combined with an intensive biofeedback effort." & "¶" & "If this is unsuccessful then other more direct modulation approaches can be tried (e.g., intravesical stimulation or foramen stimulation). The patient should be maintained on self catheterization with optional antibiotic prophylaxis (e.g., Macrodantin 50 mgm/d) while rehabilitation of the void is being tried." & "¶" & "For severe anxiety personalities, professional counseling is a useful supportive measure.", " ")

F. Pain and Retention and Sphincter Weakness

Diagnosis and Recommended Treatment:

If(Presenting_Sx="Urinary Retention" or Presenting Sx_2°="Urinary Retention", If(Presenting_Sx="Pelvic Pain" or Presenting Sx_2°="Pelvic Pain", If(Bladder Vol 1≦2, If(Cap at Vd Attpt≧200, If(Neurogenic_Status_Sx="Non-Neurogenic", If(Stress Leak Risk>20, If(UPP Dysfunct'l Score≧15, "¶Urethral Hyper Sensitivity Contributing to Pelvic Pain and Inhibition of Void Reflex. & "¶" & "Urethral weakness is present, but insufficient to cause incontinence at this point in time. However, further deterioration in sphincter competence is likely if neurodysregulation is not stabilized.", " "), " "), " "), " "), " "), " ")

G. Pain and Detrusor Urgency/Sphincter Weakness

Diagnosis:

If(Presenting_Sx="Pelvic Pain" and Presenting Sx_2°="Urinary Frequency" or Presenting_Sx="Urinary Frequency" and Presenting Sx_2°="Pelvic Pain" or Presenting_Sx="Pelvic Pain" and Presenting Sx_2°="Incontinence" or Presenting_Sx="Incontinence" and Presenting Sx_2°="Pelvic Pain", If(Neurogenic_Status_Sx="Non-Neurogenic", If(Bladder Vol 1≧5, If(Stress Leak Risk≧10, If(UPP Dysfunct'l Score≧5, "¶Pelvic Pain with an Overactive Bladder and Urethral Weakness.", " "), " "), " "), " "), " ")

Recommended Treatment:

If(C_Dx_Pain_DetrUrgeStress="¶Pelvic Pain with an Overactive Bladder and Urethral Weakness.", "¶The overactivity of the bladder distinguishes this neurologic entity from classic interstitial cystitis." & "¶" & "A cystoscopy and/or a VCUG (voiding cystourethrogram) could be performed to document any SIGNIFICANT cystocole." & "¶" & "This patient requires pharmacologic and/or neuro modulation. Initially an anticholinergic (e.g., Oxybutynin 5-10 mgm b.i.d. or Detrol 1-4 mgm qd) along with other medications (e.g., Minipress 1-2 mgm hs and/or Valium 5 m mgm b.i.d.) may be tried to help stabilize void reflexes." & "¶" & "Subsequently, neurotoxin approaches (Capsaicin or Botox instillations) can be considered, or sacral nerve stimulation to stabilize void reflexes. Surgical options can be considered, but with careful protection against wind-up. However, modulation treatment of overfacilitated lower urinary tract behavior should be pursued prior to more traditional surgery.", " ")

H. Pain and Classic Interstitial Cystitis

Diagnosis:

If(Cap at Vd Attpt≦300, If(Neurogenic_Status_Sx="Non-Neurogenic", If(Presenting Sx="Pelvic Pain" or Presenting_Sx="Urinary frequency", If(Presenting Sx_2°="Urinary frequency" or Presenting Sx_2°="Pelvic Pain" or Presenting Sx_2°=" ", If(Bladder Vol 1≦2, If(UPP Dysfunct'l Score≧10, If(Compliance_at_Capacity>5 or Sens'n_B1_at_Cap="increased", "¶Pelvic Pain Syndrome with an Up-Regulated Sensorium.", " "), " "), " "), " "), " ")

Recommended Treatment:

If(C_Dx_PainIC_Classic="¶Pelvic Pain Syndrome with an Up-Regulated Sensorium.", "¶The pelvic pain experienced by this patient is tied to inefficiency in the reflex regulation of voiding. There is increased sensitivity of the pelvic floor and bladder. CNS control over the lower urinary tract has become diffusely up-regulated with overfacilitated behavior and/or sensitization of the viscera and pelvic floor." & "¶" & "The prognosis for symptom control is greatly improved if the patient can optimize controlled relaxation of the pelvic muscles. Any decrease in pain is often reflected in improved stream quality.", " ")

I. Pain and Detrusor Urgency

Diagnosis and Recommended Treatment:

If(Presenting_Sx="Pelvic Pain" or Presenting_Sx="Urinary Frequency", If(Bladder Vol 1>1 and Bladder Vol 1≦350, If(Neurogenic_Status_Sx="Non-Neurogenic", If(Stress Leak Risk≦10, If(UPP Dysfunct'l Score≧5, "¶Pelvic Pain tied to an Overactive Bladder and Urethral Sphincter Hyperactivity and Hypersensitivity." & "¶" & "The overactivity of the bladder distinguishes this neurologic entity from classic interstitial cystitis. This patient requires pharmacologic and/or neuro modulation. An anticholinergic (e.g., Oxybutynin 5-10 mgm b.i.d. or Detrol 1-2 mgm qd), along with an alpha blocker (e.g., Minipress 1 mgm hs), can be used to help stabilize void reflexes. An antispasmodic (e.g., Valium 5 m mgm b.i.d.) can be added if necessary. Lifestyle adjustments that reduce stress, anxiety and fatigue are helpful, indeed, almost a necessity." & "¶" & "Subsequently, neurotoxin approaches (Capsaicin or Botox instillations) can be considered or sacral nerve stimulation to stabilize the bladder." & "¶" & "Augmentation cystoplasty should be used only as a last resort.", " "), " "), " "), " "), " ")

IV. Neurogenic

A. Neurogenic Disease

Diagnosis:

If(Neurogenic_Status_Sx="Neurogenic", "¶Bladder and Sphincter dysfunction evident in this study is associated with the Patient's Neurogenic Diagnosis.", " ")

B. Spastic Detrusor

Diagnosis and Recommended Treatment:

If(Bladder Vol 1≧5, If(Neurogenic_Status_Sx="Neurogenic", "¶The Cystometrogram is consistent with an overfacilitated bladder. The recommended initial approach for the problem would be use of an anticholinergic (Oxybutynin or Detrol) in doses appropriate for side effects and patient's age." & "¶" & "Neurotoxin therapy can also be considered (i.e., capsaicin, resinoferotoxin, or botox), alone or in combination with the anticholinergic meds. The advantage would be a lowering of side effects associated with higher doses of anticholinergics.", " "), " ")

C. Neurogenic Obstruction

Diagnosis and Recommended Treatment:

If(Obstr_Score_%_M≧5, If(Neurogenic_Status_Sx="Neurogenic", "¶Obstruction of the bladder outlet is evident on the urethral pressure profile. This observation should be confirmed on cystoscopy, preferably under general anaesthesia." & "¶" & "A crede flow rate can be performed at that time, with curare, to differentiate meaningful anatomic obstruction from sphincter/pelvic floor spasm. If indeed there is a significant outlet obstruction, surgical correction could also be undertaken at the time.", " "), " ")

V. Recommended Diagnostic Tests

A. Standard Studies

C_Eval'n_Std•txt="A voiding cystourethrogram (VCUG) and a cystoscopy should be performed to complete this patient's evaluation."

B. Neurologic Testing

C_Eval'n_Stim•txt="Sacral evoked potential studies followed by either a diagnostic sacral nerve block or a sacral root stimulation trial."

C. Prostatic Studies

If(C_Dx_BPH="Bladder Outlet Obstruction", C_Eval_Prostate•txt & C_Eval_Crede•Flow•txt, " ")

C_Eval_Prostate•txt="A voiding cystourethrogram (VCUG) and a cystoscopy should be performed to complete this patient's urodynamic evaluation. A rectal exam and a prostatic ultrasound are recommended to size the gland and rule out pathology other than BPH. The efficiency of prostatic compression, during voluntary pelvic striated muscle recruitment, should also be assessed during the ultrasound study."

D. Crede Flow Study

C_Eval_Crede•Flow•txt="Crede generated flow studies are recommended before and after bladder outlet surgery. This will quantify the degree of anatomical obstruction before and after surgical manipulation."

E. No Further Studies are Needed at this Time

If(C_Dx_BPH="Bladder Outlet Obstruction", C_Eval_BPH•Surg, If(Eval'n•Choice="Standard Studies", C_Eval'n_Std•txt, If(Eval'n•Choice="Neurologic Testing", C_Eval'n_Stim•txt, If(Eval'n•Choice="Prostatic Studies", C_Eval_Prostate•txt, If(Eval'n•Choice="Crede Flow Study", C_Eval_Crede•Flow•txt, "No Further Studies are needed at this time.")))))

Non Automated Menu of Diagnostic Choices

I. Specific Diagnosis
  Hypersensitive Urethra
  Hypersensitive Bladder
  Poor Pelvic Muscle Control
  Benign Prostatic Hyperplasia
  Ca Prostate
  Post RRP Anastomotic Stricture
  Post TUPR Incontinence
  Post RRP Incontinence
  Bladder Neck Hypertrophy
  Detrusor Spasticity
  Functional Sphincteric Weakness
  Dysfunctional Sphincter Spasticity
  Intrinsic Sphincter Weakness
  Radiation Injury
  Spastic Neurogenic Bladder
  Flaccid Bladder of Neurogenic Cause
  Acontractile Bladder of Aberrant Reflex Etiology
  Mixed Spastic/Flaccid Neurogenic Bladder
  Stress Incontinence
  Ideopathic/unknown factors
  Bulbar Urethra Stricture
  Membranous Urethra Stricture
  Bladder Neck Stricture
  Ideopathic Instability
  Other II. Descriptive (Functional Subclassification) Diagnosis
  Obstruction
  Incontinence
  Voiding Dysfunction III. Descriptive Category
  Anatomic, and not Behavioral
  Behavioral, and not Anatomical
  Neurologic
  Both Behavioral and Anatomical
  Behavioral, possibly Neurologic IV. Non Automated Treatment Choices
  A. Medications
  Not indicated at this time
  An Alpha-blocker, A Valium-type medication, and a tricyclic antidepressant—alone or in combination
  An Alpha-blocker (e.g., Minipress, Flomax, Clonidine Hytrin, or Cardura)
  A Valium-type medication (e.g., Ativan, Xanax, Lorazapam)
  A tricyclic antidepressant (e.g., Elavil, Paxil, Nortryptyline)
  Elavil, Minipress
  Elavil, Minipress, Valium
  Elavil 10-25 mgm
  Minipress 1 mgm
  Flomax 0.04 mgm qhs
  Hytrin 1 mgm
  Tofranil 25 mgm
  Ditropan 5 mgm B. Surgery
  Surgery not presently indicated
  TUPR
  TUI of BN
  DVIU
  Capsaicin Instillation
  Botox Sphincter Injection
  Cysto and possible bladder biopsy
  Augmentation Cystoplasty
  CystoUrethroplexy
  Modulation Trial (via S3 Stimulation)
  Foramen Electrode Implant
  Artificial Sphincter
  Collagen/Fat Injection
  Other—Add here C. Modulation
  Not Applicable
  Indicated in the Near Future
  Specific 1° Type:
    Biofeedback Reeducation of Pelvic Floor Muscle Control (Kegal Exercises)
    Acupuncture
    Psychotherapy
    a Sacral Foramen Trial
    Pelvic Floor Stimulation
  Specific 2° Type:
    and Biofeedback Reeducation of Pelvic Floor Muscle Control (Kegal Exercises)
    and Acupuncture
    and Psychotherapy
    and Sacral Foramen Trial
    and Pelvic Floor Stimulation V. Summary Reporting
  A. Prognosis
  Cure
  Improvement
  Stabilization
  B. Study Performed By
  List of Names by Title:
    Nurses
    Technicians
    Fellows
    Doctors
  C. Intro for Summary Letter
  List of Referring Sources
  D. Bladder Only Letter (CMG Letter)
  "¶" & "The overall efficiency of bladder storage/evacuation was rated as being" & Abn_Bladder %_score_Lay & "("& Int(Round(Abn_Bladder_%_score, 5)) & "%" &")"& "abnormal." & "¶¶" & "• Storage—The maximum tolerated Capacity with filling was "& Storage_B1_Cap & " cc's (N=4-500)." & "¶¶" & "• Sensation—First sensation of filling occurred at "& Sens'n_Frst_Vol & " cc's and a bladder pressure of" & Sens'n_Max_Press_Detr & "cmH2O." & "¶" & "There was "& Sens'n_B1_at_Cap & " appreciation of bladder distension on filling the bladder." & "¶¶" & "• Compliance—The Bladder pressure was "& Compliance_at_Capacity &" cmH2O (N=0), prior to the void attempt." & "¶" & "The Compliance calculation was" & Compl_Tot_Score_PerC & "% abnormal. The significance of this value is therefore—" & Compliance_Signif & "." & "¶¶" & "• Contractility—A maximum pressure of "& B1 Press on Vd Attpt &" cmH2O (N=<25) was obtained with the contraction lasting" & Det'r Dur'n & "sec." & "¶¶" & "• Reflex Integrety—Detrusor Reflex Behavior with the void attempt was "& Detr Contr'n &"." & "¶" & "Detrusor Reflex exciteability was found to be" & Detr Refl Rating & "% greater than accepted normal." & "¶" & "This degree of reflex excitability would be considered clinically to be "& Detr Reflex Signif & "."

E. Bladder/Outlet Letter (CMG+UDP Letter)

CMG Letter+"¶¶" & "The Urethral Pressure Profile was rated as being "& Abn_Profile_%_layman &" ("& Abn Profile % txt & " %) deviated from that of normal." & "¶¶" & "• Outlet Resistance—The full Profile Length measured "& UPP_Total &" cm's. The Obstructing Zone was" & Length of Obstructive Zone & "cm's. & "å" & "The Functional Sphincter zone was therefore—" & UPP_Sph_Length & "cm (N=3-3.5)." & "¶¶" & "•Average Peak Sphincter Pressure—This was measured at "& Aver Pk Press f & "cmH2O (N=60-80)." & "¶¶" & "• The Shape of the profile was consistent with a "& Profile Pattern & "posterior urethra." & "¶¶" & "• There was "& Sensitivity & "discomfort experienced by the patient to the insertion and movement of the catheter within the external urethral sphincter zone." & "¶¶" & "• Levator EMG "& Levator_EMG_1 &" " & Levator_EMG_2 & "¶¶" & "The following diagnostic impressions were suggested by the profile:" & "¶¶" & "a) There was "& Obstr_Score_%_M_Lay &" (" & Obstr_Score_%_M & " %) obstructive component." & "¶" & "b) There was "& UPP_Dysfunct'l_Score_Lay &" ("& UPP Dysfunct'l Score & "%) Spastic Dysfunction of the External Urethral Sphincter." & "¶" & "c) There was "& Stress_Leak_Risk_Lay &" ("& Stress Leak Risk & "%) risk of Stress Urinary Incontinence."

F. Bladder Outlet/Flow Rate Letter (CMG+UDP+Flow Rate)

CMG Letter+UDP Letter+"¶¶" & "The Pattern of Uroflow obtained was rated as being "& Flow_Abn Score %'age & " % deviation from normal." & "¶¶" & "The Flow Rate data obtained was as follows:" & "¶¶" & "• Peak Flow— "& Flow_Pk Flow Rate N° &" cc/sec (N=>25)." & "• Average Flow—"& Flow_Av_Rate_N° & " cc/sec (N=>12.5)." & "¶¶" & "•Post Void Residual—"& Flow_Residual & " cc (N=<15)." & "• The Volume Voided was—"& Flow_Vol Vd &" cc's (N=4-500)." & "¶¶" & "• The total Storage volume of the bladder was therefore "& Flow_StrCap &" cc (N=4-500)." & "¶¶" & "• The basic pattern of was that of a—"& Flow Curve & "." & "¶¶" & "• The main voided stream was—"& Flow Behavior MF & "." & "¶¶" & "• Termination of the stream was associated with—"& Flow Behavior PMF &"."

The provision of these calculated diagnoses and treatments could also be combined with a recognize shorthand classification system indicating the particular pattern of disability. One suggested shorthand is a "TRS" system. TRS stands for "Tone," "Reflex Excitability," and "Sensation." On physical examination, each of these factors may be rated, for example, on a scale of 0 to 3 for both the detrusor and the sphincter, respectively, the ratings corresponding to particular conditions of the respective muscles. By using the scale factors as subscripts to the TRS, a quick glance could tell a urologist or others knowledgeable in this field the nature and scope of the patient's pathology. An example of TRS classification could be: $D-T_3R_0S_1/S-T_0R_2S_2$, where the prefatory D and S stand for detrusor and sphincter, respectively. For objective clinical urodynamic testing as discussed herein, the TRS classification could be more refined, for example, using ratings on a scale of 0 to 4 or 5 to track finer nuances between conditions, provide more exacting diagnoses, and more closely matching the level of treatment necessary for the particular problem.

Patient diagnoses and recommended treatments according to the UPP diagnostic program may be provided in a summary report as shown in FIGS. 40A-G. Such a report may be automatically generated for presentation to the clinician or referring physician, to detail a course of treatment, for example, as shown in Section V: Summary Reporting above. The report may include both a narrative explanation as well as figures indicating the various UPP readings, such as flow patterns, obstruction patterns, sphincter excitability, and other graphic patterns indicating the relevant urinary tract dysfunction. The report may, for example, be displayed on a computer screen, printed on paper, transmitted by e-mail, generated in HTML as a web page, or provided in any comparable means over the Internet or any other communications network or system.

The report generation module may also link with a medical reference database to create a list of medical references and/or abstracts pertinent to the patient's condition. This reference listing may be included as part of the reporting functions of the program. In the case of reporting over a computer network, such as the Internet, the medical reference list may be in the form of hypertext links to allow the clinician or referring physician to immediately access the reference for review. The report generation module may also tie-in with the UPP diagnostic program provider's billing system to generate and include a statement of services and fees to the referring physician. The referring physician or technician may also include the patient's insurance information when entering the patient's history into the UPP diagnostic program. This insurance information may be transferred to the program provider's billing system to request payment directly from an insurer.

The method of diagnosis of urinary tract dysfunction disclosed herein provides significant advantages over the present state of the medical system. Today, appropriate diagnosis and treatment is wholly dependent upon the expertise of the treating physician. Such expertise is based upon the level of the physician's own study, research, and personal experience, which can be limited due to time, practice specialty (e.g., urologist vs. internist), geography (e.g., rural vs. urban), and other considerations. The UPP diagnostic program avoids these limitations by providing a consistent analytical framework and a thorough analysis of all relevant factors. The analysis is further based upon the application of clinically determined norms for both healthy and pathological conditions. Analysis through the UPP diagnostic program can also be based upon and compared to a database of patient groupings with similar conditions to evaluate the efficacy of treatments, experiments, or trials, for example, surgical correction, drug products, mechanical devices, implant electrical stimulation, biofeedback, drug delivery systems, bulking agents, and insertable devices. Further, the benefits of the program may be made available to anyone, practically anywhere, through the use of standard communications networks and interfaces with the program.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments and not limiting. Changes in detail or structure may be made without departing from the basic elements of the invention as defined in the following claims.

The invention claimed is:

1. A method for use in a computer system of diagnosing lower urinary system conditions of a patient, the method comprising:
   receiving urodynamic data concerning the patient;
   receiving subjective symptomatic impressions concerning the patient;
   assigning at least one weighted point value to at least one of the urodynamic data and the subjective symptomatic impressions;
   quantifying at least one norm for at least one part of lower urinary system function as at least one numeric score;
   quantifying at least one recognized pathology of lower urinary system conditions as a degree of departure from the at least one norm;
   determining a lower urinary system condition diagnosis of the patient, as a function of the degree of departure from the at least one norm, by invoking a set of rules to compare the at least one weighted point value assigned to the at least one numeric score quantified; and
   reporting the determined lower urinary system condition diagnosis.

2. The method as described in claim 1 wherein the urodynamic data comprises a urethral pressure profile of the patient.

3. The method as described in claim 2 wherein the urodynamic data further comprises sphincter dynamic data of the patient of a type of at least one the following: the internal anal sphincter, the external anal sphincter, the internal urethral sphincter, and the external urethral sphincter.

4. The method as described in claim 1 wherein the urodynamic data comprises data generated from at least one of the following diagnostic tools: radiology, ultrasound, motor sensory evoked response activity, electromyographic recordings, magnetic resonance tomography, computed tomography, and nuclear imaging.

5. The method as described in claim 1 wherein the urodynamic data comprises:
   urethra characteristics;
   bladder characteristics; and
   urinary system flow rates of the patient.

6. The method as described in claim 5 wherein the urethra characteristics and the bladder characteristics are measured in qualities of at least one of tone, reflex excitability, sensation, and structural change.

7. The method as described in claim 1 wherein the step of receiving urodynamic data further comprises:
   recognizing graphical urodynamic patterns; and
   converting the graphical urodynamic patterns into the urodynamic data.

8. The method as described in claim 1 further comprising:
   receiving a plurality of urodynamic datum and subjective symptomatic impressions concerning a plurality of patients, respectively;
   assigning a plurality of weighted point values to the plurality of urodynamic datum and subjective symptomatic impressions, respectively; and
   wherein the step of quantifying the at least one norm further comprises:
      determining the at least one numeric score as a functional average of the plurality of weighted point values; and
   wherein the step of quantifying the at least one recognized pathology further comprises:
      determining the degree of departure from the at least one norm as a functional average of the plurality of weighted point values.

9. The method as described in claim 8 further comprising:
   receiving a plurality of additional diagnostic datum concerning the plurality of patients, respectively;
   assigning a plurality of second weighted point values to the plurality of additional diagnostic datum, respectively; and
   wherein the step of quantifying the at least one norm further comprises:
      determining the at least one numeric score as a functional average of a combination of the plurality of weighted point values and the plurality of second weighted point values; and
   wherein the step of quantifying the at least one recognized pathology further comprises:
      determining the degree of departure from the at least one norm as a functional average of a combination of the plurality of weighted point values and the plurality of second weighted point values.

10. The method as described in claims 1, 8, or 9 further comprising:
   determining a treatment recommendation, as a function of the degree of departure from the at least one norm, by invoking the set of rules to compare the at least one weighted point value assigned to the at least one numeric score quantified; and
   reporting the treatment recommendation.

11. The method as described in claim 10 wherein the step of reporting further comprises:
   detailing a severity level of the lower urinary system condition diagnosis; and
   providing a treatment ladder in step with the severity level.

12. The method as described in claims 1, 8, or 9 further comprising:
   determining a recommendation for further diagnostic testing, as a function of the degree of departure from the at least one norm, by invoking the set of rules to compare the at least one weighted point value assigned to the at least one numeric score quantified; and
   reporting the recommendation for further diagnostic testing.

13. The method as described in claim 1 wherein the step of reporting further comprises generating a list of references related to the lower urinary system condition diagnosis.

14. The method as described in claim 1 further comprising generating a billing statement for a fee for using the method.

15. The method as described in claim 1 wherein the step of reporting further comprises generating a summarization letter to a medical care provider for the patient.

16. The method as described in claim 1 wherein the at least one part of lower urinary system function comprises overall lower urinary system function.

17. The method of claim 1 further comprising:
   representing the lower urinary system condition diagnosis as a level of each of a tone quality, a reflex excitability quality, and a sensation quality; and wherein the reporting operation further comprises reporting the levels of tone quality, reflex excitability quality, and sensation quality.

18. A system for diagnosing lower urinary system conditions of a patient, the system comprising:
   at least one system input that receives urodynamic data and subjective symptomatic impressions concerning the patient;
   a memory that stores
      at least one numeric score quantifying at least one norm for at least one part of lower urinary system function;
      at least one degree of departure from the at least one norm quantifying a recognized pathology of lower urinary system conditions; and
      a set of rules for processing the urodynamic data, the subjective symptomatic impressions, the at least one numeric score, and the at least one degree of departure;
   a processor that, using the set of rules, determines a lower urinary system condition diagnosis of the patient by:
      assigning at least one weighted point value to at least one of the urodynamic data and the subjective symptomatic impressions; and
      as a function of the at least one degree of departure from the at least one norm, comparing the at least one weighted point value assigned to the at least one numeric score quantified; and
   a system output that reports the lower urinary system condition diagnosis.

19. The system as described in claim 18 wherein the urodynamic data comprises a urethral pressure profile of the patient.

20. The system as described in claim 19 wherein the urodynamic data further comprises sphincter dynamic data of the patient of a type of at least one the following: the internal anal sphincter, the external anal sphincter, the internal urethral sphincter, and the external urethral sphincter.

21. The system as described in claim 18 wherein the urodynamic data comprises data generated from at least one of the following diagnostic tools: radiology, ultrasound, motor sensory evoked response activity, electromyographic recordings, magnetic resonance tomography, computed tomography, and nuclear imaging.

22. The system as described in claim 18 wherein the urodynamic data comprises:
   urethra characteristics;
   bladder characteristics; and
   urinary system flow rates of the patient.

23. The system as described in claim 22 wherein the urethra characteristics and the bladder characteristics are measured in qualities of at least one of tone, reflex excitability, sensation, and structural change.

24. The system as described in claim 18 wherein the at least one system input further comprises:
   a means for recognizing graphical urodynamic patterns and converting the graphical urodynamic patterns into the urodynamic data.

25. The system as described in claim 18 wherein the memory further comprises:
   a database that stores a plurality of urodynamic datum and subjective symptomatic impressions concerning a plurality of patients, respectively; and
   wherein the processor, using the set of rules:
      assigns a plurality of weighted point values to the plurality of urodynamic datum and subjective symptomatic impressions, respectively;
      determines the at least one numeric score as a functional average of the plurality of weighted point values; and
      determines the at least one degree of departure from the at least one norm as a functional average of the plurality of weighted point values.

26. The system as described in claim 25 wherein the database further stores a plurality of additional diagnostic datum concerning the plurality of patients, respectively; and
   wherein the processor, using the set of rules
      assigns a plurality of second weighted point values to the plurality of additional diagnostic datum, respectively;
      determines the at least one numeric score as a functional average of a combination of the plurality of weighted point values and the plurality of second weighted point values; and
      determines the at least one degree of departure from the at least one norm as a functional average of a combination of the plurality of weighted point values and the plurality of second weighted point values.

27. The system as described in claims 18, 25, or 26, wherein the processor, using the set of rules, further determines a treatment recommendation by, as a function of the at least one degree of departure from the at least one norm, comparing the at least one weighted point value assigned to the at least one numeric score quantified; and
   wherein the system output further reports the treatment recommendation.

28. The system as described in claim 27 wherein the system output further reports:
   a severity level of the urinary system condition diagnosis; and
   a treatment ladder in step with the severity level.

29. The system as described in claims 18, 25, or 26 wherein the processor, using the set of rules, further determines a recommendation for further diagnostic testing by, as a function of the at least one degree of departure from the at least one norm, comparing the at least one weighted point value assigned to the at least one numeric score quantified; and
   wherein the system output further reports the recommendation for further diagnostic testing.

30. The system as described in claim 18 wherein the at least one system input comprises a means for receiving a data transmission over a communications network.

31. The system as described in claim 18 wherein the system output comprises a means for transmitting a data transmission over a communications network.

32. The system as described in claim 18 wherein the system output further reports a list of references related to the lower urinary system condition diagnosis.

33. The system as described in claim 32 wherein the list of references further comprises links to access the references over a communication network.

34. The system as described in claims 30, 31, or 33 wherein the communications network comprises at least one of a local area network, a wide area network, a public network, a private network, an intranet, and the Internet.

35. The system as described in claim 18 wherein system output further reports a billing statement for a fee for using the system.

36. The system as described in claim 18 wherein system output further reports a summarization letter to a medical care provider for the patient.

37. The system as described in claim 18 wherein the at least one part of lower urinary system function comprises overall lower urinary system function.

38. A computer program product comprising:
a computer useable medium and computer readable code embodied on the computer useable medium for diagnosing lower urinary system conditions, the computer readable code comprising:
computer readable program code devices configured to cause a computer to accept input of urodynamic data and subjective symptomatic impressions concerning a patient over a communication network from a client machine;
computer readable program code devices configured to cause the computer to effect an assignment of at least one weighted point value to at least one of the urodynamic data and the subjective symptomatic impressions;
computer readable program code devices configured to cause the computer to effect a quantification of at least one norm for at least one part of lower urinary system function, the at least one norm being quantified as at least one numeric score;
computer readable program code devices configured to cause the computer to effect a quantification of at least one recognized pathology of lower urinary system conditions, as a degree of departure from the at least one norm; and
computer readable program code devices configured to cause the computer to effect a determination of a lower urinary system condition diagnosis of the patient, as a function of the degree of departure from the at least one norm, by invoking a set of rules to compare the at least one weighted point value to the at least one numeric score.

39. The computer program product as described in claim 38 wherein the computer readable code further comprises:
computer readable program code devices configured to cause the computer to effect a transmission of the lower urinary system condition diagnosis over the communication network to the client machine.

40. A computer program product comprising:
a computer useable medium and computer readable code embodied on the computer useable medium for diagnosing urinary system conditions, the computer readable code comprising:
computer readable program code devices configured to cause a computer to effect reception of urodynamic data and subjective symptomatic impressions concerning a patient from a computer input;
computer readable program code devices configured to cause the computer to effect an assignment of at least one weighted point value to at least one of the urodynamic data and the subjective symptomatic impressions;
computer readable program code devices configured to cause the computer to effect a quantification of at least one norm for at least one part of lower urinary system function, the at least one norm being quantified as at least one numeric score;
computer readable program code devices configured to cause the computer to effect a quantification of at least one recognized pathology of lower urinary system conditions, as a degree of departure from the at least one norm;
computer readable program code devices configured to cause the computer to effect a determination of a lower urinary system condition diagnosis of the patient, as a function of the degree of departure from the at least one norm, by invoking a set of rules to compare the at least one weighted point value to the at least one numeric score; and computer readable program code devices configured to cause the computer to effect a reporting of the lower urinary system condition diagnosis to a computer output.

41. A method for use in a computer system for determining an efficacy of a lower urinary system related treatment trial, the method comprising:
receiving first urodynamic data concerning at least one patient undergoing a treatment; receiving first subjective symptomatic impressions concerning the at least one patient;
assigning at least one first weighted point value to the first urodynamic data and the first subjective symptomatic impressions;
quantifying at least one norm for at least one part of lower urinary system function as at least one numeric score;
quantifying at least one recognized pathology of lower urinary system conditions as a degree of departure from the at least one norm;
receiving second urodynamic data concerning at least one control patient in the treatment trial;
receiving second subjective symptomatic impressions concerning the at least one control patient;
assigning at least one second weighted point value to the second urodynamic data and the second subjective symptomatic impressions;
determining a lower urinary system condition diagnosis of the at least one patient, as a function of the degree of departure from the at least one norm, by invoking a set of rules to compare the at least one first weighted point value assigned to the at least one numeric score quantified;
determining a lower urinary system condition diagnosis of the at least one control patient, as a function of the degree of departure from the at least one norm, by invoking the set of rules to compare the at least one second weighted point value assigned to the at least one numeric score quantified;
determining the efficacy of the treatment by invoking the set of rules to compare the lower urinary system condition diagnosis of the at least one patient with the lower urinary system condition diagnosis of the at least one control patient; and reporting the efficacy of the treatment.

42. The method as described in claim 41 wherein the treatment comprises at least one of a drug product, a mechanical device, implant electrical stimulation, biofeedback, reconstructive surgery, a drug delivery system, a bulking agent, and an insertable device.

43. The method as described in claim 41 wherein the treatment trial is limited to patients with a specific pathological condition.

44. A method for use in a computer system for determining an efficacy of a treatment for a lower urinary system condition of a patient, the method comprising:
receiving urodynamic data concerning the patient undergoing the treatment;
receiving subjective symptomatic impressions concerning the patient undergoing the treatment;
assigning at least one weighted point value to at least one of the urodynamic data and the subjective symptomatic impressions;
quantifying at least one norm for at least one part of lower urinary system function as at least one numeric score;
quantifying at least one recognized pathology of lower urinary system conditions as a degree of departure from the at least one norm;

determining a level of improvement of the patient, and thereby the efficacy of the treatment, as a function of the degree of departure from the at least one norm, by invoking a set of rules to compare the at least one weighted point value to the at least one numeric score; and reporting the efficacy of the treatment.

45. The method as described in claim 44 wherein the step of determining the level of improvement of the patient further comprises comparing the at least one weighted point value assigned to a previous at least one weighted point value assigned before the patient underwent the treatment.

46. The method as described in claim 44 wherein the step of determining the level of improvement of the patient further comprises comparing the at least one weighted point value assigned to a previous at least one weighted point value assigned at an earlier stage of the treatment.

47. The method as described in claim 44 wherein the step of quantifying the at least one norm is based upon a collection of urodynamic data and subjective symptomatic impressions of a plurality of patients with the lower urinary system condition.

* * * * *